(12) United States Patent
Betlach et al.

(10) Patent No.: US 6,902,913 B2
(45) Date of Patent: Jun. 7, 2005

(54) RECOMBINANT NARBONOLIDE POLYKETIDE SYNTHASE

(75) Inventors: Melanie C. Betlach, Burlingame, CA (US); Mary Betlach, San Francisco, CA (US); Robert McDaniel, Palo Alto, CA (US); Li Tang, Foster City, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 374 days.

(21) Appl. No.: 09/793,708

(22) Filed: Feb. 22, 2001

(65) Prior Publication Data

US 2003/0104597 A1 Jun. 5, 2003

Related U.S. Application Data

(63) Continuation-in-part of application No. 09/657,440, filed on Sep. 7, 2000, now Pat. No. 6,509,455, which is a division of application No. 09/320,878, filed on May 27, 1999, now Pat. No. 6,117,659, which is a continuation-in-part of application No. 09/141,908, filed on Aug. 28, 1998, now Pat. No. 6,503,741, which is a continuation-in-part of application No. 09/073,538, filed on May 6, 1998, now Pat. No. 6,558,942, which is a continuation-in-part of application No. 08/846,247, filed on Apr. 30, 1997, now Pat. No. 6,391,594.

(60) Provisional application No. 60/134,990, filed on May 20, 1999, provisional application No. 60/119,139, filed on Feb. 8, 1999, provisional application No. 60/100,880, filed on Sep. 22, 1998, and provisional application No. 60/087,080, filed on May 28, 1998.

(51) Int. Cl.[7] .......................... C12P 19/62; C07H 21/04; C12N 1/20

(52) U.S. Cl. .................. 435/72; 435/76; 435/252.3; 435/252.33; 435/252.35; 435/320.1; 536/23.2; 536/23.7

(58) Field of Search .................. 435/72, 76, 252.3, 435/252.33, 252.35, 320.1, 41, 200; 536/23.2, 23.7, 23.1

(56) References Cited

U.S. PATENT DOCUMENTS

| | | | |
|---|---|---|---|
| 4,551,433 A | 11/1985 | DeBoer | 435/253 |
| 4,874,748 A | 10/1989 | Katz et al. | 514/29 |
| 5,063,155 A | 11/1991 | Cox et al. | 435/26 |
| 5,098,837 A | 3/1992 | Beckmann et al. | 435/172.3 |
| 5,149,639 A | 9/1992 | Katz et al. | 435/76 |
| 5,168,052 A | 12/1992 | Cox et al. | 435/72 |
| 5,252,474 A | 10/1993 | Gewain et al. | 435/172.3 |
| 5,514,544 A | 5/1996 | Rao et al. | 435/6 |
| 5,672,491 A | 9/1997 | Khosla et al. | 435/148 |
| 5,712,146 A | 1/1998 | Khosla et al. | 435/252.35 |
| 5,712,496 A | 1/1998 | Takahashi et al. | 257/64 |
| 5,824,513 A | 10/1998 | Katz et al. | 453/76 |
| 5,998,194 A | 12/1999 | Summers, Jr. et al. | 435/252.33 |
| 6,200,813 B1 | 3/2001 | Katz et al. | 435/477 |
| 6,265,202 B1 | 7/2001 | Sherman et al. | 435/252.31 |

FOREIGN PATENT DOCUMENTS

| | | |
|---|---|---|
| EP | 0 238 323 | 9/1987 |
| EP | 0 791 655 | 8/1997 |
| EP | 0 791 656 | 8/1997 |
| WO | WO 93/13663 | 7/1993 |
| WO | WO 95/08548 | 3/1995 |
| WO | WO 96/40968 | 12/1996 |
| WO | WO 97/02358 | 1/1997 |
| WO | WO 97/13845 | 4/1997 |
| WO | WO 97/22711 | 6/1997 |
| WO | WO 97/23630 | 7/1997 |
| WO | WO 98/01546 | 1/1998 |
| WO | WO 98/01571 | 1/1998 |
| WO | WO 98/27203 | 6/1998 |
| WO | WO 00/00620 | 1/2000 |

OTHER PUBLICATIONS

Bartel, et al., "Biosynthesis of anthraquinones by interspecies cloning of actinorhodin biosynthesis genes in streptomycetes: Clarification of actinorhodin gene functions," *J Bacteriol* (1990) 172(9):4816–4826.

Beck, et al., "The multifunctional 6–methylsalicylic acid synthese gene of *Penicillium patulum* its gene structure relative ot that of other polyketide synthases," *Eur J Biochem* (1990) 192:487–498.

Betlach, M.C. et al., "Characterization of the Macrolide P–450 Hydroxylase from *Streptomyces venezuelae* which Converts Narbomycin t Picromycin," *Biochemistry* (1998) 37:14937–14942.

Bibb, et al., "Analysis of the nucleotide sequence of the *Streptomyces glaucescens* tcml genes provides key information about the enzymology of polyketide antibiotic biosynthesis," *EMBO J* (1989) 8(9):2727–2735.

Brown, M. J. B. et al., "A Mutant Generated by Expression of an Engineered DEBS1 Protein from the Erythromycin-Producing Polyketide Synthase (PKS) in Streptomyces Coelicolor Produces the Triketide as a Lactone, but the Major Product is the Nor–Analogue Derived from Acetate as Starter Acid," *Journal of the Chemical Society,* Chemical Communications, GB, Chemical Society, No. 15, 1995, pp. 1517–1518, XP002044729 ISSN: 0022–4936.

Caballero et al., "Organisation and functions of the actVA region of the actinorhodin biosynthetic gene cluster of *Streptomyces coelicolor,*" *Mol. Gen. Genet.* (1991) 230:401–412.

Caffrey et al., FEBS Lett. (1992), 304:225–228.

Cane, D.E. et al., J. Am. Chem. Soc. (1993), 115:522–526.

Cane, D.E. et al., J. Antibiotics (1995), 48:647–651.

(Continued)

*Primary Examiner*—Nashaat T. Nashed
(74) *Attorney, Agent, or Firm*—Morrison & Foerster LLP

(57) ABSTRACT

Recombinant DNA compounds that encode all or a portion of the narbonolide polyketide synthase are used to express recombinant polyketide synthase genes in host cells for the production of narbonolide, narbonolide derivatives, and polyketides that are useful as antibiotics and as intermediates in the synthesis of compounds with pharmaceutical value.

18 Claims, 6 Drawing Sheets

OTHER PUBLICATIONS

Cortes, J., et al., "An unusually large multifunctional polypeptide in the erythromycin–producing polyketide synthase of *Saccharopolyspora erythraea*," *Nature* (Nov. 8, 1990) 348:176–178.

Dalbie–McFarland et al., Proc Natl Acad Sci USA (1982), 79:6409.

Donadio et al., "Biosynthesis of the erythromycin macrolactone and a rational approach for producing hybrid macrolides," *Gene* 115:97–103.

Donadio et al., Industrial Microorganism, Basic and Applied Molecular Genetics 91993, R.H. Baltz, G.D. Hegeman and P1L. Skatrud (eds) (Amer. Soc. Microbial).

Donadio, S. et al., Proc Natl Acad Sci USA, (1993), 90:7119–7123.

Donadio, S., et al., "Modular Organization of Genes Required for Complex Polyketide Biosynthesis," *Science* (May 3, 1991) 252:675–679.

Evans, D.A. et al., J. Am. Chem. Soc. (1992), 114:9434–9453.

Fernandez–Moreno et al., "Nucleotide sequence and deduced functions of a set of cotranscribed genes of *Streptomyces coelicolor* A3(2): including the polyketide synthase for the antibiotic actinorhodin," *J Biol Chem* (1992) 267:19278–19290.

Fernandez–Moreno et al., "the act cluster contains regulatory and antibiotic export genes, direct targets for translational control by the bldA tRNA gene of Streptomyces," *Cell* (1991) 66:769–780.

Floss, "Genetic engineering of hybrid antibiotics—a progress report," *Tetrahydron* (1991) 47(31):6045–6058.

Fraley, R.T. et al. (1983). "Expression of Bacterial Genes in Plant Cells," *Proc. Natl. Acad. Sci. USA* 80:4803–4807.

Fu, "Engineered biosynthesis of novel polyketides: Stereochemical course of two reactions catalyzed by a polyketide synthase," *Biochemistry* (1994) 33(31):9321–9326.

Geisselsoder, J. et al. (1987). "Efficient Site–Directed in vitro Mutagenesis," *BioTechniques* 5:786–791.

Hallam (1988) "Nucleotide sequence, transcription and deduced function of a gene involved in polyketide antibiotic synthesis in *Streptomyces coelicolor*," *Gene* (1988) 74:305–320.

Hamilton et al., J. Bacteriol (1989), 171:4617.

Hopwood et al., "Product of 'hybrid' antibiotics by genetic engineering," *Nature* (1985) 314 (6012):642–644.

Ireland, R.E. et al., *J. Org. Chem*, (1980), 45:1868–1880.

Weber J.M. et al. (1985). "Genetic Analysis of Erythromycin Production in Streptomyces erythreus," *J. of Bacteriology* 164(1):425–433.

Weber J.M. et al. (1990). "Organization of a Cluster of Erythromycin Genes in *Saccharomyces erythraea*," *J. of Bacteriology* 172(5):2372–2383.

Jay, E. et al., J. Biol. Chem. (1984), 259:6311–6317.

Kao, C.M. et al., J. Am. Chem. Soc. (1994), 116:11612–11613.

Kao, C.M. et al., Science (1994), 265:509–512.

Katz et al. (1993). "Polyketide Synthesis: Prospects for Hybrid Antibiotics," *Ann. Review Microbiol* 47:875–912.

Khosla, C., et al., "Genetic construction and functional analysis of hybrid polyketide synthases containing heterologous acyl carrier proteins," *J. Bacteriol.* (1993), 175:2197–2204.

Khosla, Chaitan et al., "Generation of polyketide libraries via combinatorial biosynthesis," Tibtech Sep. 1996 (vol. 14) pp. 335–341.

Khosla, et al., "Targeted gene replacements in a Streptomyces polyketide synthase gene cluster: role for the acyl carrier protein," *Molec. Microbiol.* (1992) 6(21):3237–3249.

Kuhstoss, S. et al., *Gene* (1996) 183:231–236.

Kunkel, T.A., Proc Natl Acad Sci USA (1985), 82:448.

Lambalot, R.H. et al., J. Antibiotics (1992), 45:1981–1982.

Lehrer, R. et al., J. Immunol Meth (1991), 137:167–173.

MacNeil, D.J., J. Bacteriol (1988), 170:5607.

MacNeil, D.J., et al., "Complex organization of the *Streptomyces avermitilis* genes encoding the avermectin polyketide synthase," *Gene* 115:119–125.

Malpartida et al., "Homology between Streptomyces genes coding for synthesis of different polyketides used to clone antibiotic biosynthetic genes," *Nature* (1987) 325(6107):818–821.

Malpartida et al., "Physical and genetic characterisation of the gene cluster for the antibiotic actinorhodin in *Streptomyces coelicolor* A3(2)," *Mol. Gen. Genet.* (1986) 205:66–73.

Malpartida et al. (1984). "Molecular Cloning of the Whole Biosynthetic Pathway of a strptomyces Antibiotic and its Expression in a Heterologous Host," *Nature* 309:462–464.

Marsden, A.F.A., et al., "Engineering Broader Specificity into an Antibiotic–Producing Polyketide Synthase," *Science* (Jan. 9, 1998) 279:199–202.

Martin, S.F. et al., J. Am. Chem. Soc. (1997), 119:3193.

Masamune et al., J. Am. Chem. Soc. (1975), 97:3512–3513.

Masumoto, T. et al., Tetrohedron Lett.(1988), 29:3575.

McDaniel et al., 1993 "Engineered biosynthesis of novel polyketides," *Science* 262:1546–1550 (1993).

Oliynyk, M., et al., "A hybrid modular polyketide synthase obtained by domain swapping," *Chemistry & Biology* (Oct. 1996) 3:833–839.

Perun, T.J., Drug Action and Drug Resistance in Bacteria, vol. 1, S. Mitsuhashi (ed) Univ. Park Press, Baltimore, 1977.

Sherman et al., "Functional replacement of genes for individual polyketide synthase components in *Streptomyces coelicolor* A3(2) by hetergenous genes from a different polyketide pathway," *J. Bacteriol.* (1992) 174:6184–6190.

Sherman et al., "Structure and deduced function of the granaticin–producing polyketide synthase gene cluster of *Streptomyces violaceoruber* Tü22," *EMBO J.* (1989) 8:2717–2725.

Toshima, K. et al., J. Am. Chem. Soc. (1995), 117:3717.

Tuan et al., Gene (1990), 90:21–29.

Unpublished Manuscript, "The amino acid sequencing of the putative methymycin synthase from *Streptomyces venezuelae*." (Oct. 1997).

Vedejs, E. et al., *J Am Chem Soc* (1987), 109:5437–5446.

Vedejs, E. et al., *J Am Chem Soc* (1989), 111:8430–8438.

Woodward, R.B. et al., J. Am. Chem. Soc. (1981), 103:3215.

Xue, Y. et al., "A gene cluster for macrolide antibiotic biosynthesis in *Streptomyces venezuelae*: Architecture of metabolic diversity," *Proc. Natl. Acad. Sci. USA* (1998), 95:12111–12116.

Xue, Y. et al., "Hydroxylation of macrolactones YC–17 and narbomycin is mediated by the pikc–encoded cytochrome P450 in *Streptomyces venezuelae*," *Chemistry & Biology* (1998), 5:661–667.

Zoller, et al., Methods in Enzymology (1983), 100:468.

RECOMBINANT NARBONOLIDE POLYKETIDE SYNTHASE

CROSS-REFERENCE TO RELATED APPLICATIONS

This application claims priority under 35 U.S.C. §120 to and is a continuation-in-part of U.S. Ser. No. 09/657,440, filed 7 Sep. 2000, now U.S. Pat. No. 6,509,455, which is a division of U.S. Ser. No. 09/320,878 filed May 27, 1999, now U.S. Pat. No. 6,117,659, issued 12 Sep. 2000, which is a continuation-in-part of U.S. Ser. No. 09/141,908, filed 28 Aug. 1998, now U.S. Pat. No. 6,503,741, which is a continuation-in-part of U.S. Ser. No. 09/073,538, filed 6 May 1998 now U.S. Pat. No. 6,558,942, which is a continuation-in-part of U.S. Ser. No. 08/846,247, filed 30 Apr. 1997 now U.S. Pat. No. 6,391,594. This application also claims priority under 35 U.S.C. §119(e) to U.S. provisional application Ser. Nos. 60/134,990, filed 20 May 1999; 60/119,139, filed 8 Feb. 1999; 60/100,880, filed 22 Sep. 1998; and 60/087,080, filed 28 May 1998. Each of the above patents and patent applications is incorporated herein by reference.

REFERENCE TO GOVERNMENT FUNDING

This invention was supported in part by SBIR grant 1R43-CA75792-01. The U.S. government has certain rights in this invention.

The contents of the following submission on compact discs are incorporated herein by reference in its entirety: A compact disc copy of the Sequence Listing (COPY 1) (file name: 3006220021.txt, date recorded: Jul. 24, 2001, size: 357 KB); a duplicate compact disc copy of Sequence Listing (COPY 2) (file name: 3006220021.txt, date recorded: Jul. 24, 2001, size: 357 KB); a computer readable form copy of the Sequence Listing (CRF COPY) (file name: 3006220021.txt, date recorded: Jul. 24, 2001 size: 357 KB).

FIELD OF THE INVENTION

The present invention provides recombinant methods and materials for producing polyketides by recombinant DNA technology. The invention relates to the fields of agriculture, animal husbandry, chemistry, medicinal chemistry, medicine, molecular biology, pharmacology, and veterinary technology.

BACKGROUND OF THE INVENTION

Polyketides represent a large family of diverse compounds synthesized from 2-carbon units through a series of condensations and subsequent modifications. Polyketides occur in many types of organisms, including fungi and mycelial bacteria, in particular, the actinomycetes. There are a wide variety of polyketide structures, and the class of polyketides encompasses numerous compounds with diverse activities. Tetracycline, erythromycin, FK506, FK520, narbomycin, picromycin, rapamycin, spinocyn, and tylosin, are examples of such compounds. Given the difficulty in producing polyketide compounds by traditional chemical methodology, and the typically low production of polyketides in wild-type cells, there has been considerable interest in finding improved or alternate means to produce polyketide compounds. See PCT publication Nos. WO 93/13663; WO 95/08548; WO 96/40968; 97/02358; and 98/27203; U.S. Pat. Nos. 4,874,748; 5,063,155; 5,098,837; 5,149,639; 5,672,491; and 5,712,146; Fu et al., 1994, *Biochemistry* 33: 9321–9326; McDaniel et al., 1993, *Science* 262: 1546–1550; and Rohr, 1995, *Angew. Chem. Int. Ed. Engl.* 34(8): 881–888, each of which is incorporated herein by reference.

Polyketides are synthesized in nature by polyketide synthase (PKS) enzymes. These enzymes, which are complexes of multiple large proteins, are similar to the synthases that catalyze condensation of 2-carbon units in the biosynthesis of fatty acids. PKS enzymes are encoded by PKS genes that usually consist of three or more open reading frames (ORFs). Each ORF typically comprises two or more "modules" of ketosynthase activity, each module of which consists of at least two (if a loading module) and more typically three or more enzymatic activities or "domains." Two major types of PKS enzymes are known; these differ in their composition and mode of synthesis. These two major types of PKS enzymes are commonly referred to as Type I or "modular" and Type II "iterative" PKS enzymes.

Modular PKSs are responsible for producing a large number of 12, 14, and 16-membered macrolide antibiotics including methymycin, erythromycin, narbomycin, picromycin, and tylosin. These large multifunctional enzymes (>300,000 kDa) catalyze the biosynthesis of polyketide macrolactones through multistep pathways involving decarboxylative condensations between acyl thioesters followed by cycles of varying β-carbon processing activities (see O'Hagan, D. *The polyketide metabolites*; E. Horwood: New York, 1991, incorporated herein by reference).

During the past half decade, the study of modular PKS function and specificity has been greatly facilitated by the plasmid-based *Streptomyces coelicolor* expression system developed with the 6-deoxyerythronolide B (6-dEB) synthase (DEBS) genes (see Kao et al., 1994, *Science*, 265: 509–512, McDaniel et al., 1993, *Science* 262: 1546–1557, and U.S. Pat. Nos. 5,672,491 and 5,712,146, each of which is incorporated herein by reference). The advantages to this plasmid-based genetic system for DEBS were that it overcame the tedious and limited techniques for manipulating the natural DEBS host organism, *Saccharopolyspora erythaea*, allowed more facile construction of recombinant PKSs, and reduced the complexity of PKS analysis by providing a "clean" host background. This system also expedited construction of the first combinatorial modular polyketide library in *Streptomyces* (see PCT publication No. WO 98/43315, incorporated herein by reference).

The ability to control aspects of polyketide biosynthesis, such as monomer selection and degree of β-carbon processing, by genetic manipulation of PKSs has stimulated great interest in the combinatorial engineering of novel antibiotics (see Hutchinson, 1998, *Curr. Opin. Microbiol.* 1: 319–329; Carreras and Santi, 1998, *Curr. Opin. Biotech.* 9: 403–411; and U.S. Pat. Nos. 5,712,146 and 5,672,491, each of which is incorporated herein by reference). This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters.

The present invention provides methods and reagents relating to the PKS gene cluster for the polyketide antibiotics known as narbomycin and picromycin. Narbomycin is produced in *Streptomyces narbonensis*, and both narbomycin and picromycin are produced in *S. venezuelae*. These species are unique among macrolide producing organisms in that they produce, in addition to the 14-membered macrolides narbomycin and picromycin (picromycin is shown in FIG. 1, compound 1), the 12-membered macrolides neomethymycin and methymycin (methymycin is shown in FIG. 1, compound 2). Based on the structural similarities between picromycin and methymycin, it was speculated that methymycin would result from premature cyclization of a hexaketide intermediate in the picromycin pathway.

Glycosylation of the C5 hydroxyl group of the polyketide precursor, narbonolide, is achieved through an endogenous desosaminyl transferase to produce narbomycin. In *Streptomyces venezuelae*, narbomycin is then converted to picromycin by the endogenously produced narbomycin hydroxylase. Thus, as in the case of other macrolide antibiotics, the macrolide product of the narbonolide PKS is further modified by hydroxylation and glycosylation.

Picromycin (FIG. 1, compound 1) is of particular interest because of its close structural relationship to ketolide compounds (e.g. HMR 3004, FIG. 1, compound 3). The ketolides are a new class of semi-synthetic macrolides with activity against pathogens resistant to erythromycin (see Agouridas et al., 1998, *J. Med. Chem.* 41: 4080–4100, incorporated herein by reference). Thus, genetic systems that allow rapid engineering of the narbonolide PKS would be valuable for creating novel ketolide analogs for pharmaceutical applications. Furthermore, the production of picromycin as well as novel compounds with useful activity could be accomplished if the heterologous expression of the narbonolide PKS in *Streptomyces lividans* and other host cells were possible. The present invention meets these and other needs.

SUMMARY OF THE INVENTION

The present invention provides recombinant methods and materials for expressing PKSs derived in whole and in part from the narbonolide PKS and other genes involved in narbomycin and picromycin biosynthesis in recombinant host cells. The invention also provides the polyketides derived from the narbonolide PKS. The invention provides the complete PKS gene cluster that ultimately results, in *Streptomyces venezuelae*, in the production of picromycin. The ketolide product of this PKS is narbonolide. Narbonolide is glycosylated to obtain narbomycin and then hydroxylated at C12 to obtain picromycin. The enzymes responsible for the glycosylation and hydroxylation are also provided in recombinant form by the invention.

Thus, in one embodiment, the invention is directed to recombinant materials that contain nucleotide sequences encoding at least one domain, module, or protein encoded by a narbonolide PKS gene. The invention also provides recombinant materials useful for conversion of ketolides to antibiotics. These materials include recombinant DNA compounds that encode the C12 hydroxylase (the picK gene), the desosamine biosynthesis and desosaminyl transferase enzymes, and the beta-glucosidase enzyme involved in picromycin biosynthesis in *S. venezuelae* and the recombinant proteins that can be produced from these nucleic acids in the recombinant host cells of the invention.

In one embodiment, the invention provides a recombinant expression vector that comprises a heterologous promoter positioned to drive expression of the narbonolide PKS. In a preferred embodiment, the promoter is derived from a PKS gene. In a related embodiment, the invention provides recombinant host cells comprising the vector that produces narbonolide. In a preferred embodiment, the host cell is *Streptomyces lividans* or *S. coelicolor*.

In another embodiment, the invention provides a recombinant expression vector that comprises the desosamine biosynthetic genes as well as the desosaminyl transferase gene. In a related embodiment, the invention provides recombinant host cells comprising the vector that produces the desosamine biosynthetic gene products and desosaminyl transferase gene product. In a preferred embodiment, the host cell is *Streptomyces lividans* or *S. coelicolor*.

In another embodiment, the invention provides a method for desosaminylating polyketide compounds in recombinant host cells, which method comprises expressing the PKS for the polyketide and the desosaminyl transferase and desosamine biosynthetic genes in a host cell. In a preferred embodiment, the host cell expresses a beta-glucosidase gene as well. This preferred method is especially advantageous when producing desosaminylated polyketides in *Streptomyces* host cells, because such host cells typically glucosylate desosamine residues of polyketides, which can decrease desired activity, such as antibiotic activity. By coexpression of beta-glucosidase, the glucose residue is removed from the polyketide.

In another embodiment, the invention provides the picK hydroxylase gene in recombinant form and methods for hydroxylating polyketides with the recombinant gene product. The invention also provides polyketides thus produced and the antibiotics or other useful compounds derived therefrom.

In another embodiment, the invention provides a recombinant expression vector that comprises a promoter positioned to drive expression of a hybrid PKS comprising all or part of the narbonolide PKS and at least a part of a second PKS. In a related embodiment, the invention provides recombinant host cells comprising the vector that produces the hybrid PKS and its corresponding polyketide. In a preferred embodiment, the host cell is *Streptomyces lividans* or *S. coelicolor*.

In a related embodiment, the invention provides recombinant materials for the production of libraries of polyketides wherein the polyketide members of the library are synthesized by hybrid PKS enzymes of the invention. The resulting polyketides can be further modified to convert them to other useful compounds, such as antibiotics, typically through hydroxylation and/or glycosylation. Modified macrolides provided by the invention that are useful intermediates in the preparation of antibiotics are of particular benefit.

In another related embodiment, the invention provides a method to prepare a nucleic acid that encodes a modified PKS, which method comprises using the narbonolide PKS encoding sequence as a scaffold and modifying the portions of the nucleotide sequence that encode enzymatic activities, either by mutagenesis, inactivation, insertion, or replacement. The thus modified narbonolide PKS encoding nucleotide sequence can then be expressed in a suitable host cell and the cell employed to produce a polyketide different from that produced by the narbonolide PKS. In addition, portions of the narbonolide PKS coding sequence can be inserted into other PKS coding sequences to modify the products thereof. The narbonolide PKS can itself be manipulated, for example, by fusing two or more of its open reading frames, particularly those for extender modules 5 and 6, to make more efficient the production of 14-membered as opposed to 12-membered macrolides.

In another related embodiment, the invention is directed to a multiplicity of cell colonies, constituting a library of colonies, wherein each colony of the library contains an expression vector for the production of a modular PKS derived in whole or in part from the narbonolide PKS. Thus, at least a portion of the modular PKS is identical to that found in the PKS that produces narbonolide and is identifiable as such. The derived portion can be prepared synthetically or directly from DNA derived from organisms that produce narbonolide. In addition, the invention provides methods to screen the resulting polyketide and antibiotic libraries.

The invention also provides novel polyketides and antibiotics or other useful compounds derived therefrom. The compounds of the invention can be used in the manufacture of another compound. In a preferred embodiment, the antibiotic compounds of the invention are formulated in a mixture or solution for administration to an animal or human.

These and other embodiments of the invention are described in more detail in the following description, the examples, and claims set forth below.

DETAILED DESCRIPTION OF THE INVENTION

Figure 1:
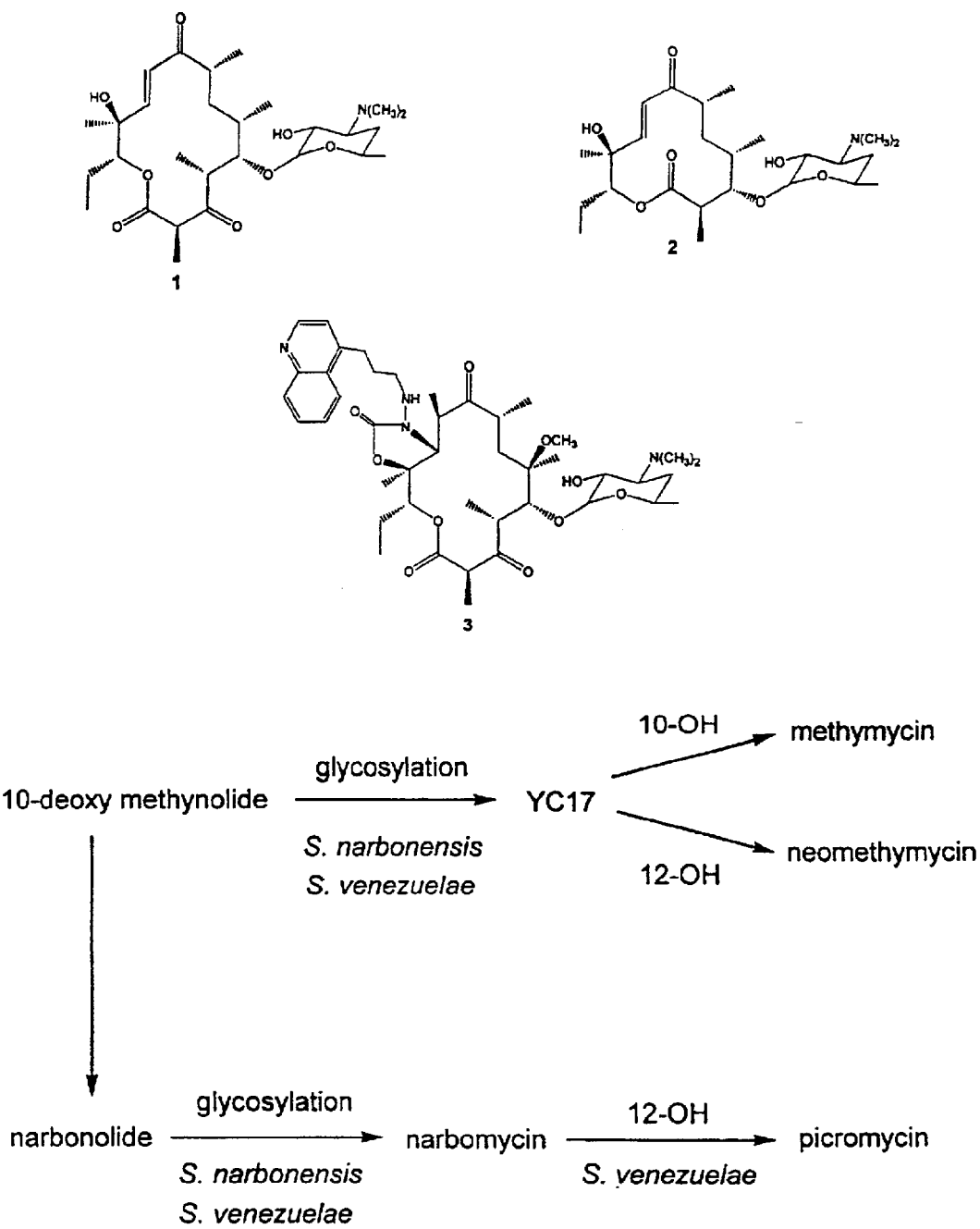
FIG. 1 shows the structures of picromycin (compound 1), methymycin (compound 2), and the ketolide HMR 3004 (compound 3).

The present invention provides useful compounds and methods for producing polyketides in recombinant host cells. As used herein, the term recombinant refers to a compound or composition produced by human intervention. The invention provides recombinant DNA compounds encoding all or a portion of the narbonolide PKS. The invention also provides recombinant DNA compounds encoding the enzymes that catalyze the further modification of the ketolides produced by the narbonolide PKS. The invention provides recombinant expression vectors useful in producing the narbonolide PKS and hybrid PKSs composed of a portion of the narbonolide PKS in recombinant host cells. Thus, the invention also provides the narbonolide PKS, hybrid PKss, and polyketide modification enzymes in recombinant form. The invention provides the polyketides produced by the recombinant PKS and polyketide modification enzymes. In particular, the invention provides methods for producing the polyketides 10-deoxymethynolide, narbonolide, YC17, narbomycin, methymycin, neomethymycin, and picromycin in recombinant host cells.

To appreciate the many and diverse benefits and applications of the invention, the description of the invention below is organized as follows. First, a general description of polyketide biosynthesis and an overview of the synthesis of narbonolide and compounds derived therefrom in *Streptomyces venezuelae* are provided. This general description and overview are followed by a detailed description of the invention in six sections. In Section I, the recombinant narbonolide PKS provided by the invention is described. In Section II, the recombinant desosamine biosynthesis genes, the desosaminyl transferase gene, and the beta-glucosidase gene provided by the invention are described. In Section III, the recombinant picK hydroxylase gene provided by the invention is described. In Section IV, methods for heterologous expression of the narbonolide PKS and narbonolide modification enzymes provided by the invention are described. In Section V, the hybrid PKS genes provided by the invention and the polyketides produced thereby are described. In Section VI, the polyketide compounds provided by the invention and pharmaceutical compositions of those compounds are described. The detailed description is followed by a variety of working examples illustrating the invention.

The narbonolide synthase gene, like other PKS genes, is composed of coding sequences organized in a loading module, a number of extender modules, and a thioesterase domain. As described more fully below, each of these domains and modules is a polypeptide with one or more specific functions. Generally, the loading module is responsible for binding the first building block used to synthesize the polyketide and transferring it to the first extender module. The building blocks used to form complex polyketides are typically acylthioesters, most commonly acetyl, propionyl, malonyl, methylmalonyl, and ethylmalonyl CoA. Other building blocks include amino acid like acylthioesters. PKSs catalyze the biosynthesis of polyketides through repeated, decarboxylative Claisen condensations between the acylthioester building blocks. Each module is responsible for binding a building block, performing one or more functions on that building block, and transferring the resulting compound to the next module. The next module, in turn, is responsible for attaching the next building block and transferring the growing compound to the next module until synthesis is complete. At that point, an enzymatic thioesterase activity cleaves the polyketide from the PKS.

Such modular organization is characteristic of the class of PKS enzymes that synthesize complex polyketides and is well known in the art. The polyketide known as 6-deoxyerythronolide B is a classic example of this type of complex polyketide. The genes, known as eryAI, eryAII, and eryAIII (also referred to herein as the DEBS genes, for the proteins, known as DEBS1, DEBS2, and DEBS3, that comprise the 6-dEB synthase), that code for the multi-subunit protein known as DEBS that synthesizes 6-dEB are described in U.S. Pat. No. 5,824,513, incorporated herein by reference. Recombinant methods for manipulating modular PKS genes are described in U.S. Pat. Nos. 5,672,491; 5,843,718; 5,830,750; and 5,712,146; and in PCT publication Nos. 98/49315 and 97/02358, each of which is incorporated herein by reference.

The loading module of DEBS consists of two domains, an acyl-transferase (AT) domain and an acyl carrier protein (ACP) domain. Each extender module of DEBS, like those of other modular PKS enzymes, contains a ketosynthase (KS), AT, and ACP domains, and zero, one, two, or three domains for enzymatic activities that modify the beta-carbon of the growing polyketide chain. A module can also contain domains for other enzymatic activities, such as, for example, a methyltransferase or dimethyltransferase activity. Finally, the releasing domain contains a thioesterase and, often, a cyclase activity.

The AT domain of the loading module recognizes a particular acyl-CoA (usually acetyl or propionyl but sometimes butyryl) and transfers it as a thiol ester to the ACP of the loading module. Concurrently, the AT on each of the extender modules recognizes a particular extender-CoA (malonyl or alpha-substituted malonyl, i.e., methylmalonyl, ethylmalonyl, and carboxylglycolyl) and transfers it to the ACP of that module to form a thioester. Once the PKS is primed with acyl- and malonyl-ACPs, the acyl group of the loading module migrates to form a thiol ester (trans-esterification) at the KS of the first extender module; at this stage, extender module 1 possesses an acyl-KS adjacent to a malonyl (or substituted malonyl) ACP. The acyl group derived from the loading module is then covalently attached to the alpha-carbon of the malonyl group to form a carbon-carbon bond, driven by concomitant decarboxylation, and generating a new acyl-ACP that has a backbone two carbons longer than the loading unit (elongation or extension). The growing polyketide chain is transferred from the ACP to the KS of the next module, and the process continues.

The polyketide chain, growing by two carbons each module, is sequentially passed as covalently bound thiol esters from module to module, in an assembly line-like process. The carbon chain produced by this process alone would possess a ketone at every other carbon atom, producing a polyketone, from which the name polyketide arises. Most commonly, however, additional enzymatic activities modify the beta keto group of each two-carbon unit just after it has been added to the growing polyketide chain but before it is transferred to the next module. Thus, in addition to the minimal module containing KS, AT, and ACP domains necessary to form the carbon-carbon bond, modules may contain a ketoreductase (KR) that reduces the keto group to an alcohol. Modules may also contain a KR plus a dehydratase (DH) that dehydrates the alcohol to a double bond. Modules may also contain a KR, a DH, and an enoylreductase (ER) that converts the double bond to a saturated single bond using the beta carbon as a methylene function. As noted above, modules may contain additional enzymatic activities as well.

Once a polyketide chain traverses the final extender module of a PKS, it encounters the releasing domain or thioesterase found at the carboxyl end of most PKSs. Here, the polyketide is cleaved from the enzyme and cyclyzed. The resulting polyketide can be modified further by tailoring enzymes; these enzymes add carbohydrate groups or methyl groups, or make other modifications, i.e., oxidation or reduction, on the polyketide core molecule.

While the above description applies generally to modular PKS enzymes, there are a number of variations that exist in nature. For example, some polyketides, such as epothilone, incorporate a building block that is derived from an amino acid. PKS enzymes for such polyketides include an activity that functions as an amino acid ligase or as a non-ribosomal peptide synthetase (NRPS). Another example of a variation, which is actually found more often than the two domain loading module construct found in DEBS, occurs when the loading module of the PKS is not composed of an AT and an ACP but instead utilizes an inactivated KS, an AT, and an ACP. This inactivated KS is in most instances called $KS^Q$, where the superscript letter is the abbreviation for the amino acid, glutamine, that is present instead of the active site cysteine required for activity. For example, the narbonolide PKS loading module contains a $KS^Q$. Yet another example of a variation has been mentioned above in the context of modules that include a methyltransferase or dimethyltransferase activity; modules can also include an epimerase activity. These variations will be described further below in specific reference to the narbonolide PKS and the various recombinant and hybrid PKSs provided by the invention.

With this general description of polyketide biosynthesis, one can better appreciate the biosynthesis of narbonolide related polyketides in *Streptomyces venezuelae* and *S. narbonensis*. The narbonolide PKS produces two polyketide products, narbonolide and 10-deoxymethynolide. Narbonolide is the polyketide product of all six extender modules of the narbonolide PKS. 10-deoxymethynolide is the polyketide product of only the first five extender modules of the narbonolide PKS. These two polyketides are desosaminylated to yield narbomycin and YC17, respectively. These two glycosylated polyketides are the final products produced in *S. narbonensis*. In *S. venezuelae*, these products are hydroxylated by the picK gene product to yield picromycin and either methymycin (hydroxylation at the C10 position of YC17) or neomethymycin (hydroxylation at the C12 position of YC17). The present invention provides the genes required for the biosynthesis of all of these polyketides in recombinant form.

Section I: The Narbonolide PKS

Figure 4:
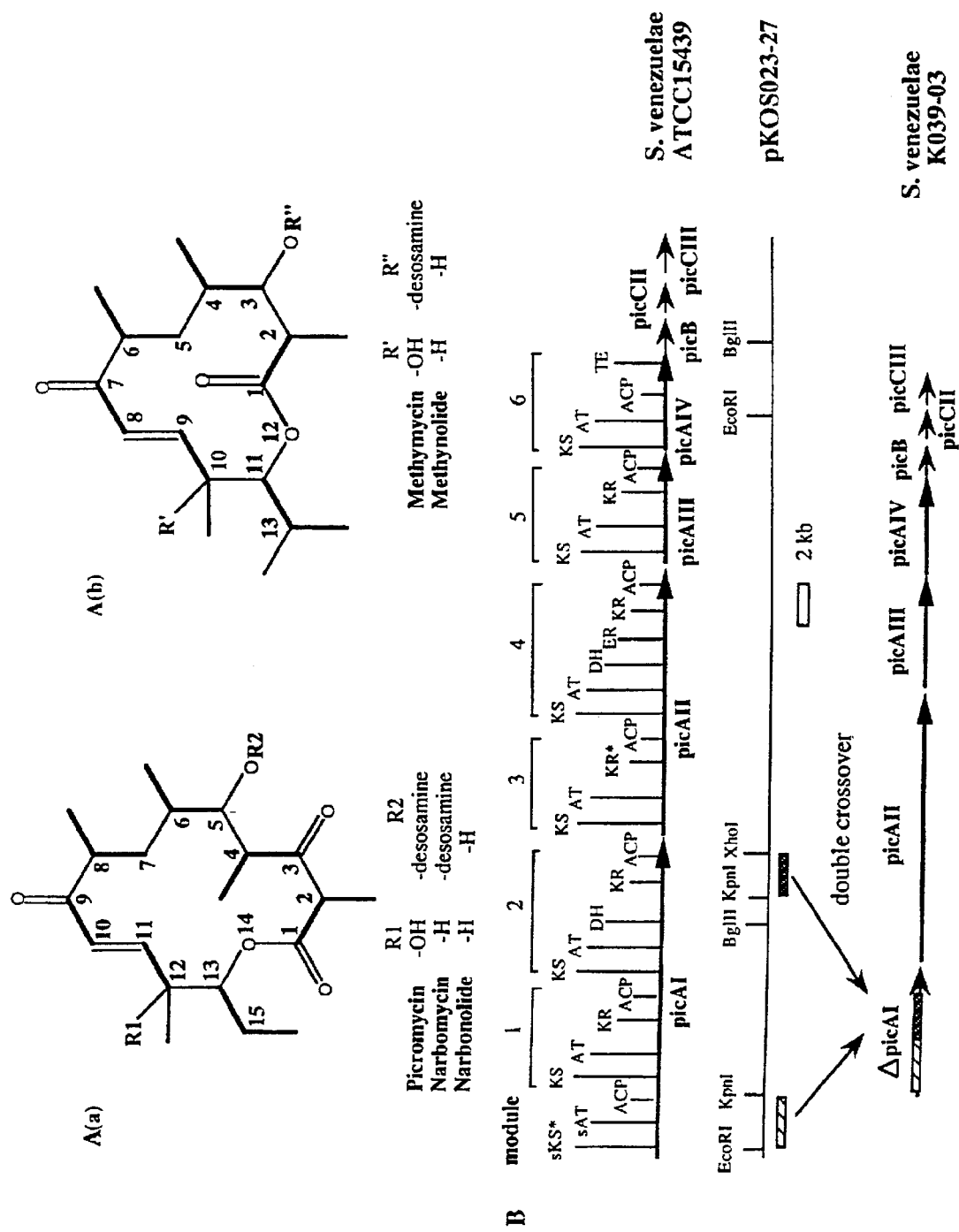
FIG. 4 has three parts. In Part A, the structures of picromycin (A(a)) and methymycin (A(b)) are shown, as well as the related structures of narbomycin, narbonolide, and methynolide. In the structures, the bolded lines indicate the two or three carbon chains produced by each module (loading and extender) of the narbonolide PKS. Part B shows the organization of the narbonolide PKS genes on the chromosome of *Streptomyces venezuelae*, including the location of the various module encoding sequences (the loading module domains are identified as sKS*, sAT, and sACP), as well as the picB thioesterase gene and two desosamine biosynthesis genes (picCII and picCIII). Part C shows the engineering of the *S. venezuelae* host of the invention in which the picAI gene has been deleted. In the Figure, ACP is acyl carrier protein; AT is acyltransferase; DH is dehydratase; ER is enoylreductase; KR is ketoreductase; KS is ketosynthase; and TE is thioesterase.

The narbonolide PKS is composed of a loading module, six extender modules, and a thioesterase domain. FIG. 4, part B, shows the organization of the narbonolide PKS genes on the *Streptomyces venezuelae* chromosome, as well as the location of the module encoding sequences in those genes, and the various domains within those modules. In the Figure, the loading module is not numbered, and its domains are indicated as sKS*, sAT, and ACP. Also shown in the Figure, part A, are the structures of picromycin and methymycin.

The loading and six extender modules and the thioesterase domain of the narbonolide PKS reside on four proteins, designated PICAI, PICAII, PICAIII, and PICAIV. PICAI includes the loading module and extender modules 1 and 2 of the PKS. PICAII includes extender modules 3 and 4. PICAIII includes extender module 5. PICAIV includes extender module 6 and a thioesterase domain. There is a second thioesterase domain (TEII) on a separate protein, designated PICB. The amino acid sequences of these proteins are shown below.

Amino acid sequence of narbonolide synthase subunit 1, PICAI (SEQ ID NO:1).

Amino acid sequence of narbonolide synthase subunit 1, PICAI (SEQ ID NO: 1).

```
   1 MSTVSKSESE EFVSVSNDAG SAHGTAEPVA VVGISCRVPG ARDPREFWEL LAAGGQAVTD
  61 VPADRWNAGD FYDPDRSAPG RSNSRWGGFI EDVDRFDAAF FGISPREAAE MDPQQRLALE
 121 LGWEALERAG IDPSSLTGTR TGVFAGAIWD DYATLKHRQG GAAITPHTVT GLHRGIIANR
 181 LSYTLGLRGP SMVVDSGQSS SLVAVHLACE SLRRGESELA LAGGVSLNLV PDSIIGASKF
 241 GGLSPDGRAY TFDARANGYV RGEGGGFVVL KRLSRAVADG DPVLAVIRGS AVNNGGAAQG
 301 MTTPDAQAQE AVLREAHERA GTAPADVRYV ELHGTGTPVG DPIEAAALGA ALGTGRPAGQ
 361 PLLVGSVKTN IGHLEGAAGI AGLIKAVLAV RGRALPASLN YETPNPAIPF EELNLRVNTE
 421 YLPWEPEHDG QRMVVGVSSF GMGGTNAHVV LEEAPGVVEG ASVVESTVGG SAVGGGVVPW
 481 VVSAKSAAAL DAQIERLAAF ASRDRTDGVD AGAVDAGAVD AGAVARVLAG GRAQFEHRAV
 541 VVGSGPDDLA AALAAPEGLV RGVASGVGRV AFVFPGQGTQ WAGMGAELLD SSAVFAAAMA
 601 ECEAALSPYV DWSLEAVVRQ APGAPTLERV DVVQPVTFAV MVSLARVWQH HGVTPQAVVG
 661 HSQGEIAAAY VAGALSLDDA ARVVTLRSKS IAAHLAGKGG MLSLALSEDA VLERLAGFDG
 721 LSVAAVNGPT ATVVSGDPVQ IEELARACEA DGVRARVIPV DYASHSRQVE IIESELAEVL
 781 AGLSPQAPRV PFFSTLEGAW ITEPVLDGGY WYRNLRHRVG FAPAVETLAT DEGFTHFVEV
 841 SAHPVLTMAL PGTVTGLATL RRDNGGQDRL VASLAEAWAN GLAVDWSPLL PSATGHHSDL
 901 PTYAFQTERH WLGEIEALAP AGEPAVQPAV LRTEAAEPAE LDRDEQLRVI LDKVRAQTAQ
 961 VLGYATGGQI EVDRTFREAG CTSLTGVDLR NRINAAFGVR MAPSMIFDFP TPEALAEQLL
1021 LVVHGEAAAN PAGAEPAPVA AAGAVDEPVA IVGMACRLPG GVASPEDLWR LVAGGGDAIS
1081 EFPQDRGWDV EGLYHPDPEH PGTSYVRQGG FIENVAGFDA AFFGISPREA LAMDPQQRLL
1141 LETSWEAVED AGIDPTSLRG RQVGVFTGAM THEYGPSLRD GGEGLDGYLL TGNTASVMSG
1201 RVSYTLGLEG PALTVDTACS SSLVALHLAV QALRKGEVDM ALAGGVAVMP TPGMFVEFSR
1261 QRGLAGDGRS KAFAASADGT SWSEGVGVLL VERLSDARRN GHQVLAVVRG SAVNQDGASN
1321 GLTAPNGPSQ QRVIRRALAD ARLTTSDVDV VEAHGTGTRL GDPIEAQALI ATYGQGRDDE
1381 QPLRLGSLKS NIGHTQAAAG VSGVIKMVQA MRHGLLPKTL HVDEPSDQID WSAGAVELLT
1441 EAVDWPEKQD GGLRRAAVSS FGISGTNAHV VLEEAPVVVE GASVVEPSVG GSAVGGGVTP
1501 WVVSAKSAAA LDAQIERLAA FASRDRTDDA DAGAVDAGAV AHVLADGRAQ FEHRAVALGA
1561 GADDLVQALA DPDGLIRGTA SGVGRVAFVF PGQGTQWAGM GAELLDSSAV FAAAMAECEA
1621 ALSPYVDWSL EAVVRQAPGA PTLERVDVVQ PVTFAVMVSL ARVWQHHGVT PQAVVGHSQG
1681 EIAAAYVAGA LPLDDAARVV TLRSKSIAAH LAGKGGMLSL ALNEDAVLER LSDFDGLSVA
1741 AVNGPTATVV SGDPVQIEEL AQACKADGFR ARIIPVDYAS HSRQVEIIES ELAQVLAGLS
1801 PQAPRVPFFS TLEGTWITEP VLDGTYWYRN LRHRVGFAPA IETLAVDEGF THFVEVSAHP
1861 VLTMTLPETV TGLGTLRREQ GGQERLVTSL AEAWVNGLPV AWTSLLPATA SRPGLPTYAF
1921 QAERYWLENT PAALATGDDW RYRIDWKRLP AAEGSERTGL SGRWLAVTPE DHSAQAAAVL
1981 TALVDAGAKV EVLTAGADDD REALAARLTA LTTGDGFTGV VSLLDGLVPQ VAWVQALGDA
2041 GIKAPLWSVT QGAVSVGRLD TPADPDRAML WGLGRVVALE HPERWAGLVD LPAQPDAAAL
2101 AHLVTALSGA TGEDQIAIRT TGLHARRLAR APLHGRRPTR DWQPHGTVLI TGGTGALGSH
2161 AARWMAHHGA EHLLLVSRSG EQAPGATQLT AELTASGARV TIAACDVADP HAMRTLLDAI
2221 PAETPLTAVV HTAGALDDGI VDTLTAEQVR RAHRAKAVGA SVLDELTRDL DLDAFVLFSS
2281 VSSTLGIPGQ GNYAPHNAYL DALAARRRAT GRSAVSVAWG PWDGGGMAAG DGVAERLRNH
```

-continued

```
2341 GVPGMDPELA LAALESALGR DETAITVADI DWDRFYLAYS DGRPQPLVEE LPEVRRIIDA

2401 RDSATSGQGG SSAQGANPLA ERLAAAAPGE RTEILLGLVR AQAAAVLRMR SPEDVAADRA

2461 FKDIGFDSLA GVELRNRLTR ATGLQLPATL VFDHPTPLAL VSLLRSEFLG DEETADARRS

2521 AALPATVGAG AGAGAGTDAD DDPIAIVAMS CRYPGDIRSP EDLWRMLSEG GEGITPFPTD

2581 RGWDLDGLYD ADPDALGRAY VREGGFLHDA AEFDAEFFGV SPREALAMDP QQRMLLTTSW

2641 EAFERAGIEP ASLRGSSTGV FIGLSYODYA ARVPNAPRGV EGYLLTGSTP SVASGRIAYT

2701 FGLEGPATTV DTACSSSLTA LHLAVRALRS GECTMALAGG VAMMATPHMF VEFSRQRALA

2761 PDGRSKAFSA DADGFGAAEG VGLLLVERLS DARRNGHPVL AVVRGTAVNQ DGASNGLTAP

2821 NGPSQQRVIR QALADARLAP GDIDAVETHG TGTSLGDPIE AQGLQATYGK ERPAERPLAI

2881 GSVKSNIGHT QAAAGAAGII KMVLAMRHGT LPKTLHADEP SPHVDWANSG LALVTEPIDW

2941 PAGTGPRRAA VSSFGISGTN AHVVLEQAPD AAGEVLGADE VPEVSETVAM AGTAGTSEVA

3001 EGSEASEAPA APGSREASLP GHLPWVLSAK DEQSLRGQAA ALHAWLSEPA ADLSDADGPA

3061 RLRDVGYTLA TSRTAFAHRA AVTAADRDGF LDGLATLAQG GTSAHVHLDT ARDGTTAFLF

3121 TGQGSQRPGA GRELYDRHPV FARALDEICA HLDGHLELPL LDVMFAAEGS AEAALLDETR

3181 TYQCALFALE VALFRLVESW GMRPAALLGH SVGEIAAAHV AGVFSLADAA RLVAARGRLM

3241 QELPAGGAML AVQAAEDEIR VWLETEERYA GRLDVAAVNG PEAAVLSGDA DAAREAEAYW

3301 SGLGRRTRAL RVSHAFHSAH MDGMLDGFRA VLETVEFRRP SLTVVSNVTG LAAGPDDLCD

3361 PEYWVRHVRG TVRFLDGVRV LRDLGVRTCL ELGPDGVLTA MAADGLADTP ADSAAGSPVG

3421 SPAGSPADSA AGALRPRPLL VALLRRKRSE TETVADALGR AHAHGTGPDW HAWFAGSGAH

3481 RVDLPTYSFR RDRYWLDAPA ADTAVDTAGL GLGTADHPLL GAVVSLPDRD GLLLTGRLSL

3541 RTHPWLADHA VLGSVLLPGA AMVELAAHAA ESAGLRDVRE LTLLEPLVLP EHGGVELRVT

3601 VGAPAGEPGG ESAGDGARPV SLHSRLADAP AGTAWSCHAT GLLATDRPEL PVAPDRAAMW

3661 PPQGAEEVPL DGLYERLDGN GLAFGPLFQG LNAVWRYEGE VFADIALPAT TNATAPATAN

3721 GGGSAAAAPY GIHPALLDAS LHAIAVGGLV DEPELVRVPF HWSGVTVHAA GAAAARVRLA

3781 SAGTDAVSLS LTDGEGRPLV SVERLTLRPV TADQAAASRV GGLMHRVAWR PYALASSGEQ

3841 DPHATSYGPT AVLGKDELKV AAALESAGVE VGLYPDLAAL SQDVAAGAPA PRTVLAPLPA

3901 GPADGGAEGV RGTVARTLEL LQAWLADEHL AGTRLLLVTR GAVRDPEGSG ADDGGEDLSH

3961 AAAWGLVRTA QTENPGRFGL LDLADDASSY RTLPSVLSDA GLRDEPQLAL HDGTIRLARL

4021 ASVRPETGTA APALAPEGTV LLTGGTGGLG GLVARHVVGE WGVRRLLLVS RRGTDAPGAD

4081 ELVHELEALG ADVSVAACDV ADREALTAVL DAIPAEHPLT AVVHTAGVLS DGTLPSMTTE

4141 DVEHVLRPKV DAAFLLDELT STPAYDLAAF VMFSSAAAVF GGAGQGAYAA ANATLDALAW

4201 RRRAAGLPAL SLGWGLWAET SGMTGELGQA DLRRMSRAGI GGISDAEGIA LLDAALRDDR

4261 HPVLLPLRLD AAGLRDAAGN DPAGIPALFR DVVGARTVRA RPSAASASTT AGTAGTPGTA

4321 DGAAETAAVT LADRAATVDG PARQRLLLEF VVGEVAEVLG HARGHRIDAE RGFLDLGFDS

4381 LTAVELRNRL NSAGGLALPA TLVFDHPSPA ALASHLDAEL PRGASDQDGA GNRNGNENGT

4441 TASRSTAETD ALLAQLTRLE GALVLTGLSD APGSEEVLEH LRSLRSMVTG ETGTGTASGA

4501 PDGAGSGAED RPWAAGDGAG GGSEDGAGVP DFMNASAEEL FGLLDQDPST D
```

Amino acid sequence of narbonolide synthase subunit 2, PICAII (SEQ ID NO: 2).

```
   1 VSTVNEEKYL DYLRRATADL HEARGRLREL EAKAGEPVAI VGMACRLPGG VASPEDLWRL

61 VAGGEDAISE FPQDRGWDVE GLYDPNPEAT GKSYAREAGF LYEAGEFDAD FFGISPREAL
```

-continued

```
 121 AMDPQQRLLL EASWEAFEHA GIPAATARGT SVGVFTGVMY HDYATRLTDV PEGIEGYLGT

181 GNSGSVASGR VAYTLGLEGP AVTVDTACSS SLVALHLAVQ ALRKGEVDMA LAGGVTVMST

241 PSTFVEFSRQ RGLAPDGRSK SFSSTADGTS WSEGVGVLLV ERLSDARRKG HRILAVVRGT

301 AVNQDGASSG LTAPNGPSQQ RVIRRALADA RLTTSDVDVV EAHGTGTRLG DPIEAQAVIA

361 TYGQGRDGEQ PLRLGSLKSN IGHTQAAAGV SGVIKMVQAM RHGVLPKTLH VEKPTDQVDW

421 SAGAVELLTE AMDWPDKGDG GLRRAAVSSF GVSGTNAHVV LEEAPAAEET PASEATPAVE

481 PSVGAGLVPW LVSAKTPAAL DAQIGRLAAF ASQGRTDAAD PGAVARVLAG GRAEFEHRAV

541 VLGTGQDDFA QALTAPEGLI RGTPSDVGRV AFVFPGQGTQ WAGMGAELLD VSKEFAAAMA

601 ECESALSRYV DWSLEAVVRQ APGAPTLERV DVVQPVTFAV MVSLAKVWQH HGVTPQAVVG

661 HSQGEIAAAY VAGALTLDDA ARVVTLRSKS IAAHLAGKGG MISLALSEEA TRQRIENLHG

721 LSIAAVNGPT ATVVSGDPTQ IQELAQACEA DGVRARIIPV DYASHSAHVE TIESELAEVL

781 AGLSPRTPEV PFFSTLEGAW ITEPVLDGTY WYRNLRHRVG FAPAVELLAT DEGFTHFIEV

841 SAHPVLTMTL PETVTGLGTL RREQGGQERL VTSLAEAWTN GLTIDWAPVL PTATGHHPEL

901 PTYAFQRRHY WLHDSPAVQG SVQDSWRYRI DWKRLAVADA SERAGLSGRW LVVVPEDRSA

961 EAAPVLAALS GAGADPVQLD VSPLGDRQRL AATLGEALAA AGGAVDGVLS LLAWDESAHP

1021 GHPAPFTRGT GATLTLVQAL EDAGVAAPLW CVTHGAVSVG RADHVTSPAQ AMVWGMGRVA

1081 ALEHPERWGG LIDLPSDADR AALDRMTTVL AGGTGEDQVA VRASGLLARR LVRASLPAHG

1141 TASPWWQADG TVLVTGAEEP AAAEAARRLA RDGAGHLLLH TPPSGSEGAE GTSGAAEDSG

1201 LAGLVAELAD LGATATVVTC DLTDAEAAAR LLAGVSDAHP LSAVLHLPPT VDSEPLAATD

1261 ADALARVVTA KATAALHLDR LLREAAAAGG RPPVLVLFSS VAAIWGGAGQ GAYAAGTAFL

1321 DALAGQHRAD GPTVTSVAWS PWEGSRVTEG ATGERLRRLG LRPLAPATAL TALDTALGHG

1381 DTAVTIADVD WSSFAPGFTT ARPGTLLADL PEARRLDEQ QSTTAADDTV LSRELGALTG

1441 AEQQRRMQEL VREHLAVVLN HPSPEAVDTG RAFRDLGFDS LTAVELRNRL KNATGLALPA

1501 TLVFDYPTPR TLAEFLLAEI LGEQAGAGEQ LPVDGGVDDE PVAIVGMACR LPGGVASPED

1561 LWRLVAGGED AISGFPQDRG WDVEGLYDPD PDASGRTYCR AGGFLDEAGE FDADFFGISP

1621 REALAMDPQQ RLLLETSWEA VEDAGIDPTS LQGQQVGVFA GTNGPHYEPL LRNTAEDLEG

1681 YVGTGNAASI MSGRVSYTLG LEGPAVTVDT ACSSSLVALH LAVQALRKGE CGLALAGGVT

1741 VMSTPTTFVE FSRQRGLAED GRSKAFAASA DGFGPAEGVG MLLVERLSDA RRNGHRVLAV

1801 VRGSAVNQDG ASNGLTAPNG PSQQRVIRRA LADARLTTAD VDVVEAHGTG TRLGDPIEAQ

1861 ALIATYGQGR DTEQPLRLGS LKSNIGHTQA AAGVSGIIKM VQAMRHGVLP KTLHVDRPSD

1921 QIDWSAGTVE LLTEAMDWPR KQEGGLRRAA VSSFGISGTN AHIVLEEAPV DEDAPADEPS

1981 VGGVVPWLVS AKTPAALDAQ IGRLAAFASQ GRTDAADPGA VARVLAGGRA QFEHRAVALG

2041 TGQDDLAAAL AAPEGLVRGV ASGVGRVAFV FPGQGTQWAG MGAELLDVSK EFAAAMAECE

2101 AALAPYVDWS LEAVVRQAPG APTLERVDVV QPVTFAVMVS LAKVWQHHGV TPQAVVGHSQ

2161 GEIAAAYVAG ALSLDDAARV VTLRSKSIGA HLAGQGGMLS LALSEAAVVE FLAGFDGLSV

2221 AAVNGPTATV VSGDPTQIQE LAQACEADGV RARIIPVDYA SHSAHVETIE SELADVLAGL

2281 SPQTPQVPFF STLEGAWITE PALDGGYWYR NLRHRVGFAP AVETLATDEG FTHFVEVSAH

2341 PVLTMALPET VTGLGTLRRD NGGQHRLTTS LAEAWANGLT VDWASLLPTT TTHPDLPTYA

2401 FQTERYWPQP DLSAAGDITS AGLGAAEHPL LGAAVLADS DGCLLTGSLS LRTHPWALDH

2461 AVAGTVLLPG TAFVELAFRA GDQVGCDLVE ELTLDAPLVL PRRGAVRVQL SVGASDESGR
```

-continued

```
2521 RTFGLYAHPE DAPGEAEWTR HATGVLAARA DRTAPVADPE AWPPPGAEPV DVDGLYERFA

2581 ANGYGYGPLF QGVRGVWRRG DEVFADVALP AEVAGAEGAR FGLHPALLDA AVQAAGAGGA

2641 FGAGTRLPFA WSGISLYAVG ATALRVRLAP AGPDTVSVSA ADSSGQPVFA ADSLTVLPVD

2701 PAQLAAFSDP TLDALHLLEW TAWDGAAQAL PGAVVLGGDA DGLAAALRAG GTEVLSFPDL

2761 TDLVEAVDRG ETPAPATVLV ACPAAGPGGP EHVREALHGS LALMQAWLAD ERFTDGRLVL

2821 VTRDAVAARS GDGLRSTGQA AVWGLGRSAQ TESPGRFVLL DLAGEARTAG DATAGDGLTT

2881 GDATVGGTSG DAALGSALAT ALGSGEPQLA LRDGALLVPR LARAAAPAAA DGLAAADGLA

2941 ALPLPAAPAL WRLEPGTDGS LESLTAAPGD AETLAPEPLG PGQVRIAIRA TGLNFRDVLI

3001 ALGMYPDPAL MGTEGAGVVT ATGPGVTHLA PGDRVMGLLS GAYAPVVVAD ARTVARMPEG

3061 WTFAQGASVP VVFLTAVYAL RDLADVKPGE RLLVHSAAGG VGMAAVQLAR HMGVEVHGTA

3121 SHGKWDALRA LGLDDAHIAS SRTLDFESAF RAASGGAGMD VVLNSLAREF VDASLRLLGP

3181 GGRFVEMGKT DVRDAERVAA DHPGVGYRAF DLGAEGPERI GEMLAEVIAL FEDGVLRHLP

3241 VTTWDVRRAR DAFRHVSQAR HTGKVVLTMP SGLDPEGTVL LTGGTGALGG IVARHVVGEW

3301 GVRRLLLVSR RGTDAPGAGE LVHELEALGA DVSVAACDVA DREALTAVLD SIPAEHPLTA

3361 VVHTAGVLSD GTLPSMTAED VEHVLRPKVD AAFLLDELTS TPGYDLAAFV MFSSAAAVFG

3421 GAGQGAYAAA NATLDALAWR RRTAGLPALS LGWGLWAETS GMTGGLSDTD RSRLARSGAT

3481 PMDSELTLSL LDAAMRRDDP ALVPIALDVA ALRAQQRDGM LAPLLSGLTR GSRVGGAPVN

3541 QRRAAAGGAG EADTDLGGRL AAMTPDDRVA HLRDLVRTHV ATVLGHGTPS RVDLERAFRD

3601 TGFDSLTAVE LRNRLNAATG LRLPATLVFD HPTPGELAGH LLDELATAAG GSWAEGTGSG

3661 DTASATDRQT TAALAELDRL EGVLASLAPA AGGRPELAAR LRALAAALGD DGDDATDLDE

3721 ASDDDLFSFI DKELGDSDF
```

Amino acid sequence of narbonolide synthase subunit 3, PICAIII (SEQ ID NO: 3).

```
   1 MANNEDKLRD YLKRVTAELQ QNTRRLREIE GRTHEPVAIV GMACRLPGGV ASPEDLWQLV

61 AGDGDAISEF PQDRGWDVEG LYDPDPDASG RTYCRSGGFL HDAGEFDADF FGISPREALA

121 MDPQQRLSLT TAWEAIESAG IDPTALKGSG LGVFVGGWHT GYTSGQTTAV QSPELEGHLV

181 SGAALGFLSG RIAYVLGTDG PALTVDTACS SSLVALHLAV QALRKGECDM ALAGGVTVMP

241 NADLFVQFSR QRGLAADGRS KAFATSADGF GPAEGAGVLL VERLSDARRN GHRILAVVRG

301 SAVNQDGASN GLTAPHGPSQ QRVIRRALAD ARLAPGDVDV VEAHGTGTRL GDPIEAQALI

361 ATYGQEKSSE QPLRLGALKS NIGHTQAAAG VAGVIKMVQA MRHGLLPKTL HVDEPSDQID

421 WSAGTVELLT EAVDWPEKQD GGLRRAAVSS FGISGTNAHV VLEEAPAVED SPAVEPPAGG

481 GVVPWPVSAK TPAALDAQIG QLAAYADGRT DVDPAVAARA LVDSRTAMEH RAVAVGDSRE

541 ALRDALRMPE GLVRGTSSDV GRVAFVFPGQ GTQWAGMGAE LLDSSPEFAA SMAECETALS

601 RYVDWSLEAV VRQEPGAPTL DRVDVVQPVT FAVMVSLAKV WQHHGITPQA VVGHSQGEIA

661 AAYVAGALTL DDAARVVTLR SKSIAAHLAG KGGMISLALD EAAVLKRLSD FDGLSVAAVN

721 GPTATVVSGD PTQIEELART CEADGVRARI IPVDYASHSR QVEIIEKELA EVLAGLAPQA

781 PHVPFFSTLE GTWITEPVLD GTYWYRNLRH RVGFAPAVET LAVDGFTHFI EVSAHPVLTM

841 TLPETVTGLG TLRREQGGQE RLVTSLAEAW ANGLTIDWAP ILPTATGHHP ELPTYAFQTE

901 RFWLQSSAPT SAADDWRYRV EWKPLTASGQ ADLSGRWIVA VGSEPEAELL GALKAAGAEV

961 DVLEAGADDD REALAARLTA LTTGDGFTGV VSLLDDLVPQ VAWVQALGDA GIKAPLWSVT

1021 QGAVSVGRLD TPADPDRAML WGLGRVVALE HPERWAGLVD LPAQPDAAAL AHLVTALSGA
```

-continued

```
1081 TGEDQIAIRT TGLHARRLAR APLHGRRPTR DWQPHGTVLI TGGTGALGSH AARWMAHHGA
1141 EHLLLVSRSG EQAPGATQLT AELTASGARV TIAACDVADP HAMRTLLDAI PAETPTLAVV
1201 HTAGAPGGDP LDVTGPEDIA RILGAKTSGA EVLDDLLRGT PLDAFVLYSS NAGVWGSGSQ
1261 GVYAAANAHL DALAARRRAR GETATSVAWG LWAGDGMGRG ADDAYWQRRG IRPMSPDRAL
1321 DELAKALSHD ETFVAVADVD WERFAPAFTV SRPSLLLDGV PEARQALAAP VGAPAPGDAA
1381 VAPTGQSSAL AAITALPEPE RRPALLTLVR THAAAVLGHS SPDRVAPGRA FTELGFDSLT
1441 AVQLRNQLST VVGNRLPATT VFDHPTPAAL AAHLHEAYLA PAEPAPTDWE GRVRRALAEL
1501 PLDRLRDAGV LDTVLRLTGI EPEPGSGGSD GGAADPGAEP EASIDDLDAE ALIRMALGPR
1561 NT
```

Amino acid sequence of narbonolide synthase subunit 4, PICAIV (SEQ ID NO: 4).

```
   1 MTSSNEQLVD ALRASLKENE ELRKESRRRA DRRQEPMAIV GMSCRFAGGI RSPEDLWDAV
  61 AAGKDLVSEV PEERGWDIDS LYDPVPGRKG TTYVRNAAFL DDAAGFDAAF FGISPREALA
 121 MDPQQRQLLE ASWEVFERAG IDPASVRGTD VGVYVGCGYQ DYAPDIRVAP EGTGGYVVTG
 181 NSSAVASGRI AYSLGLEGPA VTVDTACSSS LVALHLALKG LRNGDCSTAL VGGVAVLATP
 241 GAFIEFSSQQ AMAADGRTKG FASAADGLAW GEGVAVLLLE RLSDARRKGH RVLAVVRGSA
 301 INQDGASNGL TAPHGPSQQR LIRQALADAR LTSSDVDVVE GHGTGTRLGD PIEAQALLAT
 361 YGQGRAPGQP LRLGTLKSNI GHTQAASGVA GVIKMVQALR HGVLPKTLHV DEPTDQVDWS
 421 AGSVELLTEA VDWPERPGRL RRAGVSAFGV GGTNAHVVLE EAPAVEESPA VEPPAGGGVV
 481 PWPVSAKTSA ALDAQIGQLA AYAEDRTDVD PAVAARALVD SRTAMEHRAV AVGDSREALR
 541 DALRMPEGLV RGTVTDPGRV AFVFPGQGTQ WAGMGAELLD SSPEFAAAMA ECETALSPYV
 601 DWSLEAVVRQ APSAPTLDRV DVVQPVTFAV MVSLAKVWQH HGITPEAVIG HSQGEIAAAY
 661 VAGALTLDDA ARVVTLRSKS IAAHLAGKGG MISLALSEEA TRQRIENLHG LSIAAVNGPT
 721 ATVVSGDPTQ IQELAQACEA DGIRARIIPV DYASHSAHVE TIENELADVL AGLSPQTPQV
 781 PFFSTLEGTW ITEPALDGGY WYRNLRHRVG FAPAVETLAT DEGFTHFIEV SAHPVLTMTL
 841 PDKVTGLATL RREDGGQHRL TTSLAEAWAN GLALDWASLL PATGALSPAV PDLPTYAFQH
 901 RSYWISPAGP GEAPAHTASG REAVAETGLA WGPGAEDLDE EGRRSAVLAM VMRQAASVLR
 961 CDSPEEVPVD RPLREIGFDS LTAVDFRNRV NRLTGLQLPP TVVFEHPTPV ALAERISDEL
1021 AERNWAVAEP SDHEQAEEEK AAAPAGARSG ADTGAGAGMF RALFRQAVED DRYGEFLDVL
1081 AEASAFRPQF ASPEACSERL DPVLLAGGPT DRAEGRAVLV GCTGTAANGG PHEFLRLSTS
1141 FQEERDFLAV PLPGYGTGTG TGTALLPADL DTALDAQARA ILRAAGDAPV VLLGHSGGAL
1201 LAHELAFRLE RAHGAPPAGI VLVDPYPPGH QEPIEVWSRQ LGEGLFAGEL EPMSDARLLA
1261 MGRYARFLAG PRPGRSSAPV LLVRASEPLG DWQEERGDWR AHWDLPHTVA DVPGDHFTMM
1321 RDHAPAVAEA VLSWLDAIEG IEGAGK
```

Amino acid sequence of typeII thioesterase, PICB (SEQ ID NO: 5).

```
   1 VTDRPLNVDS GLWIRRFHPA PNSAVRLVCL PHAGGSASYF FRFSEELHPS VEALSVQYPG
  61 RQDRRAEPCL ESVEELAEHV VAATEPWWQE GRLAFFGHSL GASVAFETAR ILEQRHGVRP
 121 EGLYVSGRRA PSLAPDRLVH QLDDRAFLAE IRRLSGTDER FLQDDELLRI VLPALRSDYK
 181 AAETYLHRPS AKLTCPVMAL AGDRDPKAPL NEVAEWRRHT SGPFCLRAYS GGHFYLNDQW
 241 HEICNDISDH LLVTRGAPDA RVVQPPTSLI EGAAKRWQNP R
```

Amino acid sequence of narbonolide synthase subunit 2, PICAII (SEQ ID NO:2).

Amino acid sequence of narbonolide synthase subunit 3, PICAIII (SEQ ID NO:3).

Amino acid sequence of narbonolide synthase subunit 4, PICAIV (SEQ ID NO:4).

Amino acid sequence of typeII thioesterase, PICB (SEQ ID NO:5).

Figure 2:
FIG. 2 shows a restriction site and function map of cosmid pKOS023-27.

The DNA encoding the above proteins can be isolated in recombinant form from the recombinant cosmid pKOS023-27 of the invention, which was deposited with the American Type Culture Collection under the terms of the Budapest Treaty on 20 Aug. 1998 and is available under accession number ATCC 203141. Cosmid pKOS023-27 contains an insert of *Streptomyces venezuelae* DNA of ~38506 nucleotides. The complete sequence of the insert from cosmid pKOS023-27 is shown below. The location of the various ORFs in the insert, as well as the boundaries of the sequences that encode the various domains of the multiple modules of the PKS, are summarized in the Table below. FIG. 2 shows a restriction site and function map of pKOS023-27, which contains the complete coding sequence for the four proteins that constitute narbonolide PKS and four additional ORFs. One of these additional ORFs encodes the picB gene product, the type II thioesterase mentioned above. PICB shows a high degree of similarity to other type II thioesterases, with an identity of 51%, 49%, 45% and 40% as compared to those of *Amycolatopsis mediterranae, S. griseus, S. fradiae* and *Saccharopolyspora erythraea*, respectively. The three additional ORFs in the cosmid pKOS023-27 insert DNA sequence, from the picCII, picCIII, and picCVI, genes, are involved in desosamine biosynthesis and transfer and described in the following section.

| From Nucleotide | To Nucleotide | Description |
| --- | --- | --- |
| 70 | 13725 | picAI |
| 70 | 13725 | narbonolide synthase 1 (PICAI) |
| 148 | 3141 | loading module |
| 148 | 1434 | KS loading module |
| 1780 | 2802 | AT loading module |
| 2869 | 3141 | ACP loading module |
| 3208 | 7593 | extender module 1 |
| 3208 | 4497 | KS1 |
| 4828 | 5847 | AT1 |
| 6499 | 7257 | KR1 |
| 7336 | 7593 | ACP1 |
| 7693 | 13332 | extender module 2 |
| 7693 | 8974 | KS2 |
| 9418 | 10554 | AT2 |
| 10594 | 11160 | DH2 |
| 12175 | 12960 | KR2 |
| 13063 | 13332 | ACP2 |
| 13830 | 25049 | picAII |
| 13830 | 25049 | narbonolide synthase 2 (PICAII) |
| 13935 | 18392 | extender module 3 |
| 13935 | 15224 | KS3 |
| 15540 | 16562 | AT3 |
| 17271 | 18071 | KR3 (inactive) |
| 18123 | 18392 | ACP3 |
| 18447 | 24767 | extender module 4 |
| 18447 | 19736 | KS4 |
| 20031 | 21050 | AT4 |
| 21093 | 21626 | DH4 |
| 22620 | 23588 | ER4 |
| 23652 | 24423 | KR4 |
| 24498 | 24765 | ACP4 |
| 25133 | 29821 | picAIII |
| 25133 | 29821 | narbonolide synthase 3 (PICAIII) |
| 25235 | 29567 | extender module 5 |
| 25235 | 26530 | KS5 |
| 26822 | 27841 | AT5 |
| 28474 | 29227 | KR5 |
| 29302 | 29569 | ACP5 |
| 29924 | 33964 | picAIV |
| 29924 | 33964 | narbonolide synthase 4 (PICAIV) |
| 30026 | 32986 | extender module 6 |
| 30026 | 31312 | KS6 |
| 31604 | 32635 | AT6 |
| 32708 | 32986 | ACP6 |
| 33068 | 33961 | PKS thioesterase domain |
| 33961 | 34806 | picB |
| 33961 | 34806 | type II thioesterase homolog |
| 34863 | 36011 | picCII |
| 34863 | 36011 | 4-keto-6-deoxyglucose isomerase |
| 36159 | 37439 | picCIII |
| 36159 | 37439 | desosaminyl transferase |
| 37529 | 38242 | picCVI |
| 37529 | 38242 | 3-amino dimethyltransferase |

DNA Sequence of the Insert DNA in Cosmid pKOS023-27 (SEQ ID NO:19).

| DNA Sequence of the Insert DNA in Cosmid pKOS023-27 (SEQ ID 19). | | | | | |
| --- | --- | --- | --- | --- | --- |
| 1 | GATCATGCGG | AGCACTCCTT | CTCTCGTGCT | CCTACCGGTG | ATGTGCGCGC CGAATTGATT |
| 61 | CGTGGAGAGA | TGTCGACAGT | GTCCAAGAGT | GAGTCCGAGG | AATTCGTGTC CGTGTCGAAC |
| 121 | GACGCCGGTT | CCGCGCACGG | CACAGCGGAA | CCCGTCGCCG | TCGTCGGCAT CTCCTGCCGG |
| 181 | GTGCCCGGCG | CCCGGGACCC | GAGAGAGTTC | TGGGAACTCC | TGGCGGCAGG CGGCCAGGCC |
| 241 | GTCACCGACG | TCCCCGCGGA | CCGCTGGAAC | GCCGGCGACT | TCTACGACCC GGACCGCTCC |
| 301 | GCCCCCGGCC | GCTCGAACAG | CCGGTGGGGC | GGGTTCATCG | AGGACGTCGA CCGGTTCGAC |
| 361 | GCCGCCTTCT | TCGGCATCTC | GCCCCGCGAG | GCCGCGGAGA | TGGACCCGCA GCAGCGGCTC |
| 421 | GCCCTGGAGC | TGGGCTGGGA | GGCCCTGGAG | CGCGCCGGGA | TCGACCCGTC CTCGCTCACC |
| 481 | GGCACCCGCA | CCGGCGTCTT | CGCCGGCGCC | ATCTGGGACG | ACTACGCCAC CCTGAAGCAC |

-continued

DNA Sequence of the Insert DNA in Cosmid pKOS023-27 (SEQ ID 19).

```
 541 CGCCAGGGCG GCGCCGCGAT CACCCCGCAC ACCGTCACCG GCCTCCACCG CGGCATCATC
 601 GCGAACCGAC TCTCGTACAC GCTCGGGCTC CGCGGCCCCA GCATGGTCGT CGACTCCGGC
 661 CAGTCCTCGT CGCTCGTCGC CGTCCACCTC GCGTGCGAGA GCCTGCGGCG CGGCGAGTCC
 721 GAGCTCGCCC TCGCCGGCGG CGTCTCGCTC AACCTGGTGC CGGACAGCAT CATCGGGGCG
 781 AGCAAGTTCG GCGGCCTCTC CCCCGACGGC CGCGCCTACA CCTTCGACGC GCGCGCCAAC
 841 GGCTACGTAC GCGGCGAGGG CGGCGGTTTC GTCGTCCTGA AGCGCCTCTC CCGGGCCGTC
 901 GCCGACGGCG ACCCGGTGCT CGCCGTGATC CGGGGCAGCG CCGTCAACAA CGGCGGCGCC
 961 GCCCAGGGCA TGACGACCCC CGACGCGCAG GCGCAGGAGG CCGTGCTCCG CGAGGCCCAC
1021 GAGCGGGCCG GGACCGCGCC GGCCGACGTG CGGTACGTCG AGCTGCACGG CACCGGCACC
1081 CCCGTGGGCG ACCCGATCGA GGCCGCTGCG CTCGGCGCCG CCCTCGGCAC CGGCCGCCCG
1141 GCCGGACAGC CGCTCCTGGT CGGCTCGGTC AAGACGAACA TCGGCCACCT GGAGGGCGCG
1201 GCCGGCATCG CCGGCCTCAT CAAGGCCGTC CTGGCGGTCC GCGGTCGCGC GCTGCCCGCC
1261 AGCCTGAACT ACGAGACCCC GAACCCGGCG ATCCCGTTCG AGGAACTGAA CCTCCGGGTG
1321 AACACGGAGT ACCTGCCGTG GGAGCCGGAG CACGACGGGC AGCGGATGGT CGTCGGCGTG
1381 TCCTCGTTCG GCATGGGCGG CACGAACGCG CATGTCGTGC TCGAAGAGGC CCCGGGGGTT
1441 GTCGAGGGTG CTTCGGTCGT GGAGTCGACG GTCGGCGGGT CGGCGGTCGG CGGCGGTGTG
1501 GTGCCGTGGG TGGTGTCGGC GAAGTCCGCT GCCGCGCTGG ACGCGCAGAT CGAGCGGCTT
1561 GCCGCGTTCG CCTCGCGGGA TCGTACGGAT GGTGTCGACG CGGGCGCTGT CGATGCGGGT
1621 GCTGTCGATG CGGGTGCTGT CGCTCGCGTA CTGGCCGGCG GGCGTGCTCA GTTCGAGCAC
1681 CGGGCCGTCG TCGTCGGCAG CGGGCCGGAC GATCTGGCGG CAGCGCTGGC CGCGCCTGAG
1741 GGTCTGGTCC GGGGCGTGGC TTCCGGTGTC GGGCGAGTGG CGTTCGTGTT CCCCGGGCAG
1801 GGCACGCAGT GGGCCGGCAT GGGTGCCGAA CTGCTGGACT CTTCCGCGGT GTTCGCGGCG
1861 GCCATGGCCG AATGCGAGGC CGCACTCTCC CCGTACGTCG ACTGGTCGCT GGAGGCCGTC
1921 GTACGGCAGG CCCCCGGTGC GCCCACGCTG GAGCGGGTCG ATGTCGTGCA GCCTGTGACG
1981 TTCGCCGTCA TGGTCTCGCT GGCTCGCGTG TGGCAGCACC ACGGGGTGAC GCCCCAGGCG
2041 GTCGTCGGCC ACTCGCAGGG CGAGATCGCC GCCGCGTACG TCGCCGGTGC CCTGAGCCTG
2101 GACGACGCCG CTCGTGTCGT GACCCTGCGC AGCAAGTCCA TCGCCGCCCA CCTCGCCGGC
2161 AAGGGCGGCA TGCTGTCCCT CGCGCTGAGC GAGGACGCCG TCCTGGAGCG ACTGGCCGGG
2221 TTCGACGGGC TGTCCGTCGC CGCTGTGAAC GGGCCCACCG CCACCGTGGT CTCCGGTGAC
2281 CCCGTACAGA TCGAAGAGCT TGCTCGGGCG TGTGAGGCCG ATGGGGTCCG TGCGCGGGTC
2341 ATTCCCGTCG ACTACGCGTC CCACAGCCGG CAGGTCGAGA TCATCGAGAG CGAGCTCGCC
2401 GAGGTCCTCG CCGGGCTCAG CCCGCAGGCT CCGCGCGTGC CGTTCTTCTC GACACTCGAA
2461 GGCGCCTGGA TCACCGAGCC CGTGCTCGAC GGCGGCTACT GGTACCGCAA CCTGCGCCAT
2521 CGTGTGGGCT TCGCCCCGGC CGTCGAGACC CTGGCCACCG ACGAGGGCTT CACCCACTTC
2581 GTCGAGGTCA GCGCCCACCC CGTCCTCACC ATGGCCCTCC CCGGGACCGT CACCGGTCTG
2641 GCGACCCTGC GTCGCGACAA CGGCGGTCAG GACCGCCTCG TCGCCTCCCT CGCCGAAGCA
2701 TGGGCCAACG GACTCGCGGT CGACTGGAGC CCGCTCCTCC CCTCCGCGAC CGGCCACCAC
2761 TCCGACCTCC CCACCTACGC GTTCCAGACC GAGCGCCACT GGCTGGGCGA GATCGAGGCG
2821 CTCGCCCCGG CGGGCGAGCC GGCGGTGCAG CCCGCCGTCC TCCGCACGGA GGCGGCCGAG
```

DNA Sequence of the Insert DNA in Cosmid pKOS023-27 (SEQ ID 19).

```
2881  CCGGCGGAGC TCGACCGGGA CGAGCAGCTG CGCGTGATCC TGGACAAGGT CCGGGCGCAG

2941  ACGGCCCAGG TGCTGGGGTA CGCGACAGGC GGGCAGATCG AGGTCGACCG GACCTTCCGT

3001  GAGGCCGGTT GCACCTCCCT GACCGGCGTG GACCTGCGCA ACCGGATCAA CGCCGCCTTC

3061  GGCGTACGGA TGGCGCCGTC CATGATCTTC GACTTCCCCA CCCCCGAGGC TCTCGCGGAG

3121  CAGCTGCTCC TCGTCGTGCA CGGGGAGGCG GCGGCGAACC CGGCCGGTGC GGAGCCGGCT

3181  CCGGTGGCGG CGGCCGGTGC CGTCGACGAG CCGGTGGCGA TCGTCGGCAT GGCCTGCCGC

3241  CTGCCCGGTG GGGTCGCCTC GCCGGAGGAC CTGTGGCGGC TGGTGGCCGG CGGCGGGGAC

3301  GCGATCTCGG AGTTCCCGCA GGACCGCGGC TGGGACGTGG AGGGGCTGTA CCACCCGGAT

3361  CCCGAGCAAC CCGGCACGTC GTACGTCCGC CAGGGCGGTT TCATCGAGAA CGTCGCCGGC

3421  TTCGACGCGG CCTTCTTCGG GATCTCGCCG CGCGAGGCCC TCGCCATGGA CCCGCAGCAG

3481  CGGCTCCTCC TCGAAACCTC CTGGGAGGCC GTCGAGGACG CCGGGATCGA CCCGACCTCC

3541  CTGCGGGGAC GGCAGGTCGG CGTCTTCACT GGGGCGATGA CCCACGAGTA CGGGCCGAGC

3601  CTGCGGGACG GCGGGGAAGG CCTCGACGGC TACCTGCTGA CCGGCAACAC GGCCAGCGTG

3661  ATGTCGGGCC GCGTCTCGTA CACACTCGGC CTTGAGGGCC CCGCCCTGAC GGTGGACACG

3721  GCCTGCTCGT CGTCGCTGGT CGCCCTGCAC CTCGCCGTGC AGGCCCTGCG CAAGGGCGAG

3781  GTCGACATGG CGCTCGCCGG CGGCGTGGCC GTGATGCCCA CGCCCGGGAT GTTCGTCGAG

3841  TTCAGCCGGC AGCGCGGGCT GGCCGGGGAC GGCCGGTCGA AGGCGTTCGC CGCGTCGGCG

3901  GACGGCACCA GCTGGTCCGA GGGCGTCGGC GTCCTCCTCG TCGAGCGCCT GTCGGACGCC

3961  CGCCGCAACG GACACCAGGT CCTCGCGGTC GTCCGCGGCA GCGCCGTGAA CCAGGACGGC

4021  GCGAGCAACG GCCTCACGGC TCCGAACGGG CCCTCGCAGC AGCGCGTCAT CCGGCGCGCG

4081  CTGGCGGACG CCCGGCTGAC GACCTCCGAC GTGGACGTCG TCGAGGCACA CGGCACGGGC

4141  ACGCGACTCG GCGACCCGAT CGAGGCGCAG GCCCTGATCG CCACCTACGG CCAGGGCCGT

4201  GACGACGAAC AGCCGCTGCG CCTCGGGTCG TTGAAGTCCA ACATCGGGCA CACCCAGGCC

4261  GCGGCCGGCG TCTCCGGTGT CATCAAGATG GTCCAGGCGA TGCGCCACGG ACTGCTGCCG

4321  AAGACGCTGC ACGTCGACGA GCCCTCGGAC CAGATCGACT GGTCGGCTGG CGCCGTGGAA

4381  CTCCTCACCG AGGCCGTCGA CTGGCCGGAG AAGCAGGACG GCGGGCTGCG CCGGGCCGCC

4441  GTCTCCTCCT TCGGGATCAG CGGCACCAAT GCGCATGTGG TGCTCGAAGA GGCCCCGGTG

4501  GTTGTCGAGG GTGCTTCGGT CGTCGAGCCG TCGGTTGGCG GGTCGGCGGT CGGCGGCGGT

4561  GTGACGCCTT GGGTGGTGTC GGCGAAGTCC GCTGCCGCGC TCGACGCGCA GATCGAGCGG

4621  CTTGCCGCAT TCGCCTCGCG GGATCGTACG GATGACGCCG ACGCCGGTGC TGTCGACGCG

4681  GGCGCTGTCG CTCACGTACT GGCTGACGGG CGTGCTCAGT TCGAGCACCG GGCCGTCGCG

4741  CTCGGCGCCG GGGCGGACGA CCTCGTACAG GCGCTGGCCG ATCCGGACGG GCTGATACGC

4801  GGAACGGCTT CCGGTGTCGG GCGAGTGGCG TTCGTGTTCC CCGGTCAGGG CACGCAGTGG

4861  GCTGGCATGG GTGCCGAACT GCTGGACTCT TCCGCGGTGT TCGCGGCGGC CATGGCCGAG

4921  TGTGAGGCCG CGCTGTCCCC GTACGTCGAC TGGTCGCTGG AGGCCGTCGT ACGGCAGGCC

4981  CCCGGTGCGC CCACGCTGGA GCGGGTCGAT GTCGTGCAGC CTGTGACGTT CGCCGTCATG

5041  GTCTCGCTGG CTCGCGTGTG GCAGCACCAC GGTGTGACGC CCAGGCGGT CGTCGGCCAC

5101  TCGCAGGGCG AGATCGCCGC CGCGTACGTC GCCGGAGCCC TGCCCCTGGA CGACGCCGCC
```

-continued

DNA Sequence of the Insert DNA in Cosmid pKOS023-27 (SEQ ID 19).

```
5161 CGCGTCGTCA CCCTGCGCAG CAAGTCCATC GCCGCCCACC TCGCCGGCAA GGGCGGCATG
5221 CTGTCCCTCG CGCTGAACGA GGACGCCGTC CTGGAGCGAC TGAGTGACTT CGACGGGCTG
5281 TCCGTCGCCG CCGTCAACGG GCCCACCGCC ACTGTCGTGT CGGGTGACCC CGTACAGATC
5341 GAAGAGCTTG CTCAGGCGTG CAAGGCGGAC GGATTCCGCG CGCGGATCAT TCCCGTCGAC
5401 TACGCGTCCC ACAGCCGGCA GGTCGAGATC ATCGAGAGCG AGCTCGCCCA GGTCCTCGCC
5461 GGTCTCAGCC CGCAGGCCCC GCGCGTGCCG TTCTTCTCGA CGCTCGAAGG CACCTGGATC
5521 ACCGAGCCCG TCCTCGACGG CACCTACTGG TACCGCAACC TCCGTCACCG CGTCGGCTTC
5581 GCCCCCGCCA TCGAGACCCT GGCCGTCGAC GAGGGCTTCA CGCACTTCGT CGAGGTCAGC
5641 GCCCACCCCG TCCTCACCAT GACCCTCCCC GAGACCGTCA CCGGCCTCGG CACCCTCCGT
5701 CGCGAACAGG GAGGCCAAGA GCGTCTGGTC ACCTCGCTCG CCGAGGCGTG GGTCAACGGG
5761 CTTCCCGTGG CATGGACTTC GCTCCTGCCC GCCACGGCCT CCCGCCCCGG TCTGCCCACC
5821 TACGCCTTCC AGGCCGAGCG CTACTGGCTC GAGAACACTC CCGCCGCCCT GGCCACCGGC
5881 GACGACTGGC GCTACCGCAT CGACTGGAAG CGCCTCCCGG CCGCCGAGGG GTCCGAGCGC
5941 ACCGGCCTGT CCGGCCGCTG GCTCGCCGTC ACGCCGGAGG ACCACTCCGC GCAGGCCGCC
6001 GCCGTGCTCA CCGCGCTGGT CGACGCCGGG GCGAAGGTCG AGGTGCTGAC GGCCGGGGCG
6061 GACGACGACC GTGAGGCCCT CGCCGCCCGG CTCACCGCAC TGACGACCGG TGACGGCTTC
6121 ACCGGCGTGG TCTCGCTCCT CGACGGACTC GTACCGCAGG TCGCCTGGGT CCAGGCGCTC
6181 GGCGACGCCG GAATCAAGGC GCCCCTGTGG TCCGTCACCC AGGGCGCGGT CTCCGTCGGA
6241 CGTCTCGACA CCCCCGCCGA CCCCGACCGG GCCATGCTCT GGGGCCTCGG CCGCGTCGTC
6301 GCCCTTGAGC ACCCCGAACG CTGGGCCGGC CTCGTCGACC TCCCCGCCCA GCCCGATGCC
6361 GCCGCCCTCG CCCACCTCGT CACCGCACTC TCCGGCGCCA CCGGCGAGGA CCAGATCGCC
6421 ATCCGCACCA CCGGACTCCA CGCCCGCCGC CTCGCCCGCG CACCCCTCCA CGGACGTCGG
6481 CCCACCCGCG ACTGGCAGCC CCACGGCACC GTCCTCATCA CCGGCGGCAC CGGAGCCCTC
6541 GGCAGCCACG CCGCACGCTG GATGGCCCAC CACGGAGCCG AACACCTCCT CCTCGTCAGC
6601 CGCAGCGGCG AACAAGCCCC CGGAGCCACC CAACTCACCG CCGAACTCAC CGCATCGGGC
6661 GCCCGCGTCA CCATCGCCGC CTGCGACGTC GCCGACCCCC ACGCCATGCG CACCCTCCTC
6721 GACGCCATCC CCGCCGAGAC GCCCCTCACC GCCGTCGTCC ACACCGCCGG CGCGCTCGAC
6781 GACGGCATCG TGGACACGCT GACCGCCGAG CAGGTCCGGC GGGCCCACCG TGCGAAGGCC
6841 GTCGGCGCCT CGGTGCTCGA CGAGCTGACC CGGGACCTCG ACCTCGACGC GTTCGTGCTC
6901 TTCTCGTCCG TGTCGAGCAC TCTGGGCATC CCCGGTCAGG GCAACTACGC CCCGCACAAC
6961 GCCTACCTCG ACGCCCTCGC GGCTCGCCGC CGGGCCACCG GCCGGTCCGC CGTCTCGGTG
7021 GCCTGGGGAC CGTGGGACGG TGGCGGCATG GCCGCCGGTG ACGGCGTGGC CGAGCGGCTG
7081 CGCAACCACG GCGTGCCCGG CATGGACCCG GAACTCGCCC TGGCCGCACT GGAGTCCGCG
7141 CTCGGCCGGG ACGAGACCGC GATCACCGTC GCGGACATCG ACTGGGACCG CTTCTACCTC
7201 GCGTACTCCT CCGGTCGCCC GCAGCCCCTC GTCGAGGAGC TGCCCGAGGT GCGGCGCATC
7261 ATCGACGCAC GGGACAGCGC CACGTCCGGA CAGGGCGGGA GCTCCGCCCA GGGCGCCAAC
7321 CCCCTGGCCG AGCGGCTGGC CGCCGCGGCT CCCGGCGAGC GTACGGAGAT CCTCCTCGGT
7381 CTCGTACGGG CGCAGGCCGC CGCCGTGCTC CGGATGCGTT CGCCGGAGGA CGTCGCCGCC
7441 GACCGCGCCT TCAAGGACAT CGGCTTCGAC TCGCTCGCCG GTGTCGAGCT GCGCAACAGG
```

-continued

DNA Sequence of the Insert DNA in Cosmid pKOS023-27 (SEQ ID 19).

```
7501 CTGACCCGGG CGACCGGGCT CCAGCTGCCC GCGACGCTCG TCTTCGACCA CCCGACGCCG
7561 CTGGCCCTCG TGTCGCTGCT CCGCAGCGAG TTCCTCGGTG ACGAGGAGAC GGCGGACGCC
7621 CGGCGGTCCG CGGCGCTGCC CGCGACTGTC GGTGCCGGTG CCGGCGCCGG CGCCGGCACC
7681 GATGCCGACG ACGATCCGAT CGCGATCGTC GCGATGAGCT GCCGCTACCC CGGTGACATC
7741 CGCAGCCCGG AGGACCTGTG GCGGATGCTG TCCGAGGGCG GCGAGGGCAT CACGCCGTTC
7801 CCCACCGACC GCGGCTGGGA CCTCGACGGC CTGTACGACG CCGACCCGGA CGCGCTCGGC
7861 AGGGCGTACG TCCGCGAGGG CGGGTTCCTG CACGACGCGG CCGAGTTCGA CGCGGAGTTC
7921 TTCGGCGTCT CGCCGCGCGA GGCGCTGGCC ATGGACCCGC AGCAGCGGAT GCTCCTGACG
7981 ACGTCCTGGG AGGCCTTCGA GCGGGCCGGC ATCGAGCCGG CATCGCTGCG CGGCAGCAGC
8041 ACCGGTGTCT TCATCGGCCT CTCCTACCAG GACTACGCGG CCCGCGTCCC GAACGCCCCG
8101 CGTGGCGTGG AGGGTTACCT GCTGACCGGC AGCACGCCGA GCGTCGCGTC GGGCCGTATC
8161 GCGTACACCT TCGGTCTCGA AGGGCCCGCG ACGACCGTCG ACACCGCCTC CTCGTCGTCG
8221 CTGACCGCCC TGCACCTGGC GGTGCGGGCG CTGCGCAGCG GCGAGTGCAC GATGGCGCTC
8281 GCCGGTGGCG TGGCGATGAT GGCGACCCCG CACATGTTCG TGGAGTTCAG CCGTCAGCGG
8341 GCGCTCGCCC CGGACGGCCG CAGCAAGGCC TTCTCGGCGG ACGCCGACGG GTTCGGCGCC
8401 GCGGAGGGCG TCGGCCTGCT GCTCGTGGAG CGGCTCTCGG ACGCGCGGCG CAACGGTCAC
8461 CCGGTGCTCG CCGTGGTCCG CGGTACCGCC GTCAACCAGG ACGGCGCCAG CAACGGGCTG
8521 ACCGCGCCCA ACGGACCCTC GCAGCAGCGG GTGATCCGGC AGGCGCTCGC CGACGCCCGG
8581 CTGGCACCCG GCGACATCGA CGCCGTCGAG ACGCACGGCA CGGGAACCTC GCTGGGCGAC
8641 CCCATCGAGG CCCAGGGCCT CCAGGCCACG TACGGCAAGG AGCGGCCCGC GGAACGGCCG
8701 CTCGCCATCG GCTCCGTGAA GTCCAACATC GGACACACCC AGGCCGCGGC CGGTGCGGCG
8761 GGCATCATCA AGATGGTCCT CGCGATGCGC CACGGCACCC TGCCGAAGAC CCTCCACGCC
8821 GACGAGCCGA GCCCGCACGT CGACTGGGCG AACAGCGGCC TGGCCCTCGT CACCGAGCCG
8881 ATCGACTGGC CGGCCGGCAC CGGTCCGCGC CGCGCCGCCG TCTCCTCCTT CGGCATCAGC
8941 GGGACGAACG CGCACGTCGT GCTGGAGCAG GCGCCGGATG CTGCTGGTGA GGTGCTTGGG
9001 GCCGATGAGG TGCCTGAGGT GTCTGAGACG GTAGCGATGG CTGGGACGGC TGGGACCTCC
9061 GAGGTCGCTG AGGGCTCTGA GGCCTCCGAG GCCCCGCGG CCCCCGGCAG CCGTGAGGCG
9121 TCCCTCCCCG GCACCTGCC CTGGGTGCTG TCCGCCAAGG ACGAGCAGTC GCTGCGCGGC
9181 CAGGCCGCCG CCCTGCACGC GTGGCTGTCC GAGCCCGCC CCGACCTGTC GGACGCGGAC
9241 GGACCGGCCC GCCTGCGGGA CGTCGGGTAC ACGCTCGCCA CGAGCCGTAC CGCCTTCGCG
9301 CACCGCGCCG CCGTGACCGC CGCCGACCGG GACGGGTTCC TGGACGGGCT GGCCACGCTG
9361 GCCCAGGGCG GCACCTCGGC CCACGTCCAC CTGGACACCG CCCGGGACGG CACCACCGCG
9421 TTCCTCTTCA CCGGCCAGGG CAGTCAGCGC CCCGGCGCCG GCCGTGAGCT GTACGACCGG
9481 CACCCCGTCT TCGCCCGGGC GCTCGACGAG ATCTGCGCCC ACCTCGACGG TCACCTCGAA
9541 CTGCCCCTGC TCGACGTGAT GTTCGCGGCC GAGGGCAGCG CGGAGGCCGC GCTGCTCGAC
9601 GAGACGCGGT ACACGCAGTG CGCGCTGTTC GCCCTGGAGG TCGCGCTCTT CCGGCTCGTC
9661 GAGAGCTGGG GCATGCGGCC GGCCGCACTG CTCGGTCACT CGGTCGGCGA GATCGCCGCC
9721 GCGCACGTCG CCGGTGTGTT CTCGCTCGCC GACGCCGCCC GCCTGGTCGC CGCGCGCGGC
```

-continued

DNA Sequence of the Insert DNA in Cosmid pKOS023-27 (SEQ ID 19).

```
 9781 CGGCTCATGC AGGAGCTGCC CGCCGGTGGC GCGATGCTCG CCGTCCAGGC CGCGGAGGAC
 9841 GAGATCCGCG TGTGGCTGGA GACGGAGGAG CGGTACGCGG GACGTCTGGA CGTCGCCGCC
 9901 GTCAACGGCC CCGAGGCCGC CGTCCTGTCC GGCGACGCGG ACGCGGCGCG GGAGGCGGAG
 9961 GCGTACTGGT CCGGGCTCGG CCGCAGGACC CGCGCGCTGC GGGTCAGCCA CGCCTTCCAC
10021 TCCGCGCACA TGGACGGCAT GCTCGACGGG TTCCGCGCCG TCCTGGAGAC GGTGGAGTTC
10081 CGGCGCCCCT CCCTGACCGT GGTCTCGAAC GTCACCGCC TGGCCGCCGG CCCCGGACGAC
10141 CTGTGCGACC CCGAGTACTG GGTCCGGCAC GTCCGCGGCA CCGTCCGCTT CCTCGACGGC
10201 GTCCGTGTCC TGCGCGACCT CGGCGTGCGG ACCTGCCTGG AGCTGGGCCC CGACGGGGTC
10261 CTCACCGCCA TGGCGGCCGA CGGCCTCGCG GACACCCCCG CGGATTCCGC TGCCGGCTCC
10321 CCCGTCGGCT CTCCCGCCGG CTCTCCCGCC GACTCCGCCG CCGGCGCGCT CCGGCCCCGG
10381 CCGCTGCTCG TGGCGCTGCT GCGCCGCAAG CGGTCGGAGA CCGAGACCGT CGCGGACGCC
10441 CTCGGCAGGG CGCACGCCCA CGGCACCGGA CCCGACTGGC ACGCCTGGTT CGCCGGCTCC
10501 GGGGCGCACC GCGTGGACCT GCCCACGTAC TCCTTCCGGC GCGACCGCTA CTGGCTGGAC
10561 GCCCCGGCGG CCGACACCGC GGTGGACACC GCCGGCCTCG GTCTCGGCAC CGCCGACCAC
10621 CCGCTGCTCG GCGCCGTGGT CAGCCTTCCG GACCGGGACG GCCTGCTGCT CACCGGCCGC
10681 CTCTCCCTGC GCACCCACCC GTGGCTCGCG GACCACGCCG TCCTGGGGAG CGTCCTGCTC
10741 CCCGGCGCCG CGATGGTCGA ACTCGCCGCG CACGCTGCGG AGTCCGCCGG TCTGCGTGAC
10801 GTGCGGGAGC TGACCCTCCT TGAACCGCTG GTACTGCCCG AGCACGGTGG CGTCGAGCTG
10861 CGCGTGACGG TCGGGGCGCC GGCCGGAGAG CCCGGTGGCG AGTCGGCCGG GGACGGCGCA
10921 CGGCCCGTCT CCCTCCACTC GCGGCTCGCC GACGCGCCCG CCGGTACCGC CTGGTCCTGC
10981 CACGCGACCG GTCTGCTGGC CACCGACCGG CCCGAGCTTC CCGTCGCGCC CGACCGTGCG
11041 GCCATGTGGC CGCCGCAGGG CGCCGAGGAG GTGCCGCTCG ACGGTCTCTA CGAGCGGCTC
11101 GACGGGAACG GCCTCGCCTT CGGTCCGCTG TTCCAGGGGC TGAACGCGGT GTGGCGGTAC
11161 GAGGGTGAGG TCTTCGCCGA CATCGCGCTC CCCGCCACCA CGAATGCGAC CGCGCCCGCG
11221 ACCGCGAACG GCGGCGGGAG TGCGGCGGCG GCCCCCTACG GCATCCACCC CGCCCTGCTC
11281 GACGCTTCGC TGCACGCCAT CGCGGTCGGC GGTCTCGTCG ACGAGCCCGA GCTCGTCCGC
11341 GTCCCCTTCC ACTGGAGCGG TGTCACCGTG CACGCGGCCG GTGCCGCGGC GGCCCGGGTC
11401 CGTCTCGCCT CCGCGGGGAC GGACGCCGTC TCGCTGTCCC TGACGGACGG CGAGGGACGC
11461 CCGCTGGTCT CCGTGGAACG GCTCACGCTG CGCCCGGTCA CCGCCGATCA GGCGGCGGCG
11521 AGCCGCGTCG GCGGGCTGAT GCACCGGGTG GCCTGGCGTC CGTACGCCCT CGCCTCGTCC
11581 GGCGAACAGG ACCCGCACGC CACTTCGTAC GGGCCGACCG CCGTCCTCGG CAAGGACGAG
11641 CTGAAGGTCG CCGCCGCCCT GGAGTCCGCG GGCGTCGAAG TCGGGCTCTA CCCCGACCTG
11701 GCCGCGCTGT CCCAGGACGT GGCGGCCGGC GCCCCGGCGC CCGTACCGT CCTTGCGCCG
11761 CTGCCCGCGG GTCCCGCCGA CGGCGGCGCG GAGGGTGTAC GGGGCACGGT GGCCCCGGACG
11821 CTGGAGCTGC TCCAGGCCTG GCTGGCCGAC GAGCACCTCG CGGGCACCCG CCTGCTCCTG
11881 GTCACCCGCG GTGCGGTGCG GGACCCCGAG GGGTCCGGCG CCGACGATGC GGCGAGGAC
11941 CTGTCGCACG CGGCCGCCTG GGGTCTCGTA CGGACCGCGC AGACCGAGAA CCCCGGCCGC
12001 TTCGGCCTTC TCGACCTGGC CGACGACGCC TCGTCGTACC GGACCCTGCC GTCGGTGCTC
12061 TCCGACGCGG GCCTGCGCGA CGAACCGCAG CTCGCCCTGC ACGACGGCAC CATCAGGCTG
```

-continued

DNA Sequence of the Insert DNA in Cosmid pKOS023-27 (SEQ ID 19).

```
12121  GCCCGCCTGG CCTCCGTCCG GCCCGAGACC GGCACCGCCG CACCGGCGCT CGCCCCGGAG
12181  GGCACGGTCC TGCTGACCGG CGGCACCGGC GGCCTGGGCG GACTGGTCGC CCGGCACGTG
12241  GTGGGCGAGT GGGGCGTACG ACGCCTGCTG CTGGTGAGCC GGCGGGCAC GGACGCCCCG
12301  GGCGCCGACG AGCTCGTGCA CGAGCTGGAG GCCCTGGGAG CCGACGTCTC GGTGGCCGCG
12361  TGCGACGTCG CCGACCGCGA AGCCCTCACC GCCGTACTCG ACGCCATCCC CGCCGAACAC
12421  CCGCTCACCG CGGTCGTCCA CACGGCAGGC GTCCTCTCCG ACGGCACCCT CCCGTCCATG
12481  ACGACGGAGG ACGTGGAACA CGTACTGCGG CCCAAGGTCG ACGCCGCGTT CCTCCTCGAC
12541  GAACTCACCT CGACGCCCGC ATACGACCTG GCAGCGTTCG TCATGTTCTC CTCCGCCGCC
12601  GCCGTCTTCG GTGGCGCGGG GCAGGGCGCC TACGCCGCCG CCAACGCCAC CCTCGACGCC
12661  CTCGCCTGGC GCCGCCGGGC AGCCGGACTC CCCGCCCTCT CCCTCGGCTG GGGCCTCTGG
12721  GCCGAGACCA GCGGCATGAC CGGCGAGCTC GGCCAGGCGG ACCTGCGCCG GATGAGCCGC
12781  GCGGGCATCG GCGGGATCAG CGACGCCGAG GGCATCGCGC TCCTCGACGC CGCCCTCCGC
12841  GACGACCGCC ACCCGGTCCT GCTGCCCCTG CGGCTCGACG CCGCCGGGCT GCGGGACGCG
12901  GCCGGGAACG ACCCGGCCGG AATCCCGGCG CTCTTCCGGG ACGTCGTCGG CGCCAGGACC
12961  GTCCGGGCCC GGCCGTCCGC GGCCTCCGCC TCGACGACAG CCGGGACGGC CGGCACGCCG
13021  GGGACGGCGG ACGGCGCGGC GGAAACGGCG GCGGTCACGC TCGCCGACCG GGCCGCCACC
13081  GTGGACGGGC CCGCACGGCA GCGCCTGCTG CTCGAGTTCG TCGTCGGCGA GGTCGCCGAA
13141  GTACTCGGCC ACGCCCGCGG TCACCGGATC GACGCCGAAC GGGGCTTCCT CGACCTCGGC
13201  TTCGACTCCC TGACCGCCGT CGAACTCCGC AACCGGCTCA ACTCCGCCGG TGGCCTCGCC
13261  CTCCCGGCGA CCCTGGTCTT CGACCACCCA AGCCCGGCGG CACTCGCCTC CCACCTGGAC
13321  GCCGAGCTGC CGCGCGGCGC CTCGGACCAG GACGGAGCCG GAACCGGAA CGGGAACGAG
13381  AACGGGACGA CGGCGTCCCG GAGCACCGCC GAGACGGACG CGCTGCTGGC ACAACTGACC
13441  CGCCTGGAAG GCGCCTTGGT GCTGACGGGC CTCTCGGACG CCCCCGGGAG CGAAGAAGTC
13501  CTGGAGCACC TGCGGTCCCT GCGCTCGATG GTCACGGGCG AGACCGGGAC CGGGACCGCG
13561  TCCGGAGCCC CGGACGGCGC CGGGTCCGGC GCCGAGGACC GGCCCTGGGC GGCCGGGGAC
13621  GGAGCCGGGG GCGGGAGTGA GGACGGCGCG GGAGTGCCGG ACTTCATGAA CGCCTCGGCC
13681  GAGGAACTCT TCGGCCTCCT CGACCAGGAC CCCAGCACGG ACTGATCCCT GCCGCACGGT
13741  CGCCTCCCGC CCCGGACCCC GTCCCGGGCA CCTCGACTCG AATCACTTCA TGCGCGCCTC
13801  GGGCGCCTCC AGGAACTCAA GGGGACAGCG TGTCCACGGT GAACGAAGAG AAGTACCTCG
13861  ACTACCTGCG TCGTGCCACG GCGGACCTCC ACGAGGCCCG TGGCCGCCTC CGCGAGCTGG
13921  AGGCGAAGGC GGGCGAGCCG GTGGCGATCG TCGGCATGGC CTGCCGCCTG CCCGGCGGCG
13981  TCGCCTCGCC CGAGGACCTG TGGCGGCTGG TGGCCGGCGG CGAGGACGCG ATCTCGGAGT
14041  TCCCCCAGGA CCGCGGCTGG GACGTGGAGG GCCTGTACGA CCCGAACCCG GAGGCCACGG
14101  GCAAGAGTTA CGCCCGCGAG GCCGGATTCC TGTACGAGGC GGGCGAGTTC GACGCCGACT
14161  TCTTCGGGAT CTCGCCGCGC GAGGCCCTCG CCATGGACCC GCAGCAGCGT CTCCTCCTGG
14221  AGGCCTCCTG GGAGGCGTTC GAGCACGCCG GGATCCCGGC GGCCACCGCG CGCGGCACCT
14281  CGGTCGGCGT CTTCACCGGC GTGATGTACC ACGACTACGC CACCCGTCTC ACCGATGTCC
14341  CGGAGGGCAT CGAGGGCTAC CTGGGCACCG GCAACTCCGG CAGTGTCGCC TCGGGCCGCG
```

-continued

DNA Sequence of the Insert DNA in Cosmid pKOS023-27 (SEQ ID 19).

```
14401 TCGCGTACAC GCTTGGCCTG GAGGGGCCGG CCGTCACGGT CGACACCGCC TGCTCGTCCT
14461 CGCTGGTCGC CCTGCACCTC GCCGTGCAGG CCCTGCGCAA GGGCGAGGTC GACATGGCGC
14521 TCGCCGGCGG CGTGACGGTC ATGTCGACGC CCAGCACCTT CGTCGAGTTC AGCCGTCAGC
14581 GCGGGCTGGC GCCGGACGGC CGGTCGAAGT CCTTCTCGTC GACGGCCGAC GGCACCAGCT
14641 GGTCCGAGGG CGTCGGCGTC CTCCTCGTCG AGCGCCTGTC CGACGCGCGT CGCAAGGGCC
14701 ATCGGATCCT CGCCGTGGTC CGGGGCACCG CCGTCAACCA GGACGGCGCC AGCAGCGGCC
14761 TCACGGCTCC GAACGGGCCG TCGCAGCAGC GCGTCATCCG ACGTGCCCTG GCGGACGCCC
14821 GGCTCACGAC CTCCGACGTG GACGTCGTCG AGGCCCACGG CACGGGTACG CGACTCGGCG
14881 ACCCGATCGA GGCGCAGGCC GTCATCGCCA CGTACGGGCA GGGCCGTGAC GGCGAACAGC
14941 CGCTGCGCCT CGGGTCGTTG AAGTCCAACA TCGGACACAC CCAGGCCGCC GCCGGTGTCT
15001 CCGGCGTGAT CAAGATGGTC CAGGCGATGC GCCACGGCGT CCTGCCGAAG ACGCTCCACG
15061 TGGAGAAGCC GACGGACCAG GTGGACTGGT CCGCGGGCGC GGTCGAGCTG CTCACCGAGG
15121 CCATGGACTG GCCGGACAAG GGCGACGGCG GACTGCGCAG GCCGCGGTC TCCTCCTTCG
15181 GCGTCAGCGG GACGAACGCG CACGTCGTGC TCGAAGAGGC CCCGGCGGCC GAGGAGACCC
15241 CTGCCTCCGA GGCGACCCCG GCCGTCGAGC CGTCGGTCGG CGCCGGCCTG GTGCCGTGGC
15301 TGGTGTCGGC GAAGACTCCG GCCGCGCTGG ACGCCCAGAT CGGACGCCTC GCCGCGTTCG
15361 CCTCGCAGGG CCGTACGGAC GCCGCCGATC CGGGCGCGGT CGCTCGCGTA CTGGCCGGCG
15421 GGCGCGCCGA GTTCGAGCAC CGGGCCGTCG TGCTCGGCAC CGGACAGGAC GATTTCGCGC
15481 AGGCGCTGAC CGCTCCGGAA GGACTGATAC GCGGCACGCC CTCGGACGTG GGCCGGGTGG
15541 CGTTCGTGTT CCCCGGTCAG GGCACGCAGT GGGCCGGGAT GGGCGCCGAA CTCCTCGACG
15601 TGTCGAAGGA GTTCGCGGCG GCCATGGCCG AGTGCGAGAG CGCGCTCTCC CGCTATGTCG
15661 ACTGGTCGCT GGAGGCCGTC GTCCGGCAGG CGCCGGGCGC GCCCACGCTG GAGCGGGTCG
15721 ACGTCGTCCA GCCCGTGACC TTCGCTGTCA TGGTTTCGCT GGCGAAGGTC TGGCAGCACC
15781 ACGGCGTGAC GCCGCAGGCC GTCGTCGGCC ACTCGCAGGG CGAGATCGCC GCCGCGTACG
15841 TCGCCGGTGC CCTCACCCTC GACGACGCCG CCCGCGTCGT CACCCTGCGC AGCAAGTCCA
15901 TCGCCGCCCA CCTCGCCGGC AAGGGCGGCA TGATCTCCCT CGCCCTCAGC GAGGAAGCCA
15961 CCCGGCAGCG CATCGAGAAC CTCCACGGAC TGTCGATCGC CGCCGTCAAC GGCCCCACCG
16021 CCACCGTGGT TTCGGGCGAC CCCACCCAGA TCCAAGAGCT CGCTCAGGCG TGTGAGGCCG
16081 ACGGGGTCCG CGCACGGATC ATCCCCGTCG ACTACGCCTC CCACAGCGCC CACGTCGAGA
16141 CCATCGAGAG CGAACTCGCC GAGGTCCTCG CCGGGCTCAG CCCGCGGACA CCTGAGGTGC
16201 CGTTCTTCTC GACACTCGAA GGCGCCTGGA TCACCGAGCC GGTGCTCGAC GGCACCTACT
16261 GGTACCGCAA CCTCCGCCAC GCGTCGGCT TCGCCCCCGC CGTCGAGACC CTCGCCACCG
16321 ACGAAGGCTT CACCCACTTC ATCGAGGTCA GCGCCCACCC CGTCCTCACC ATGACCCTCC
16381 CCGAGACCGT CACCGGCCTC GGCACCCTCC GCCGCGAACA GGGAGGCCAG GAGCGTCTGG
16441 TCACCTCACT CGCCGAAGCC TGGACCAACG GCCTCACCAT CGACTGGGCG CCCGTCCTCC
16501 CCACCGCAAC CGGCCACCAC CCCGAGCTCC CCACCTACGC CTTCCAGCGC CGTCACTACT
16561 GGCTCCACGA CTCCCCCGCC GTCCAGGGCT CCGTGCAGGA CTCCTGGCGC TACCGCATCG
16621 ACTGGAAGCG CCTCGCGGTC GCCGACGCGT CCGAGCGCGC CGGGCTGTCC GGGCGCTGGC
16681 TCGTCGTCGT CCCCGAGGAC CGTTCCGCCG AGGCCGCCCC GGTGCTCGCC GCGCTGTCCG
```

-continued

DNA Sequence of the Insert DNA in Cosmid pKOS023-27 (SEQ ID 19).

```
16741 GCGCCGGCGC CGACCCCGTA CAGCTGGACG TGTCCCCGCT GGGCGACCGG CAGCGGCTCG
16801 CCGCGACGCT GGGCGAGGCC CTGGCGGCGG CCGGTGGAGC CGTCGACGGC GTCCTCTCGC
16861 TGCTCGCGTG GGACGAGAGC GCGCACCCCG GCCACCCCGC CCCCTTCACC CGGGGCACCG
16921 GCGCCACCCT CACCCTGGTG CAGGCGCTGG AGGACGCCGG CGTCGCCGCC CCGCTGTGGT
16981 GCGTGACCCA CGGCGCGGTG TCCGTCGGCC GGGCCGACCA CGTCACCTCC CCCGCCCAGG
17041 CCATGGTGTG GGGCATGGGC CGGGTCGCCG CCCTGGAGCA CCCCGAGCGG TGGGGCGGCC
17101 TGATCGACCT GCCCTCGGAC GCCGACCGGG CGGCCCTGGA CCGCATGACC ACGGTCCTCG
17161 CCGGCGGTAC GGGTGAGGAC CAGGTCGCGG TACGCGCCTC CGGGCTGCTC GCCCGCCGCC
17221 TCGTCCGCGC CTCCCTCCCG GCGCACGGCA CGGCTTCGCC GTGGTGGCAG GCCGACGGCA
17281 CGGTGCTCGT CACCGGTGCC GAGGAGCCTG CGGCCGCCGA GGCCGCACGC CGGCTGGCCC
17341 GCGACGGCGC CGGACACCTC CTCCTCCACA CCACCCCCTC CGGCAGCGAA GGCGCCGAAG
17401 GCACCTCCGG TGCCGCCGAG GACTCCGGCC TCGCCGGGCT CGTCGCCGAA CTCGCGGACC
17461 TGGGCGCGAC GGCCACCGTC GTGACCTGCG ACCTCACGGA CGCGGAGGCG CCGCCCGGC
17521 TGCTCGCCGG CGTCTCCGAC GCGCACCCGC TCAGCGCCGT CCTCCACCTG CCGCCCACCG
17581 TCGACTCCGA GCCGCTCGCC GCGACCGACG CGGACGCGCT CGCCCGTGTC GTGACCGCGA
17641 AGGCCACCGC CGCGCTCCAC CTGGACCGCC TCCTGCGGGA GGCCGCGGCT GCCGGAGGCC
17701 GTCCGCCCGT CCTGGTCCTC TTCTCCTCGG TCGCCGCGAT CTGGGCGGC GCCGGTCAGG
17761 GCGCGTACGC CGCCGGTACG GCCTTCCTCG ACGCCCTCGC CGGTCAGCAC CGGGCCGACG
17821 GCCCCACCGT GACCTCGGTG GCCTGGAGCC CCTGGGAGGG CAGCCGCGTC ACCGAGGGTG
17881 CGACCGGGGA GCGGCTGCGC CGCCTCGGCC TGCGCCCCCT CGCCCCCGCG ACGGCGCTCA
17941 CCGCCCTGGA CACCGCGCTC GGCCACGGCG ACACCGCCGT CACGATCGCC GACGTCGACT
18001 GGTCGAGCTT CGCCCCCGGC TTCACCACGG CCCGGCCGGG CACCCTCCTC GCCGATCTGC
18061 CCGAGGCGCG CCGCGCGCTC GACGAGCAGC AGTCGACGAC GGCCGCCGAC GACACCGTCC
18121 TGAGCCGCGA GCTCGGTGCG CTCACCGGCG CCGAACAGCA GCGCCGTATG CAGGAGTTGG
18181 TCCGCGAGCA CCTCGCCGTG GTCCTCAACC ACCCCTCCCC CGAGGCCGTC GACACGGGGC
18241 GGGCCTTCCG TGACCTCGGA TTCGACTCGC TGACGGCGGT CGAGCTCCGC AACCGCCTCA
18301 AGAACGCCAC CGGCCTGGCC CTCCCGGCCA CTCTGGTCTT CGACTACCCG ACCCCCCGGA
18361 CGCTGGCGGA GTTCCTCCTC GCGGAGATCC TGGGCGAGCA GGCCGGTGCC GGCGAGCAGC
18421 TTCCGGTGGA CGGCGGGGTC GACGACGAGC CCGTCGCGAT CGTCGGCATG GCGTGCCGCC
18481 TGCCGGGCGG TGTCGCCTCG CCGGAGGACC TGTGGCGGCT GGTGGCCGGC GGCGAGGACG
18541 CGATCTCCGG CTTCCCGCAG GACCGCGGCT GGGACGTGGA GGGGCTGTAC GACCCGGACC
18601 CGGACGCGTC CGGGCGGACG TACTGCCGTG CCGGTGGCTT CCTCGACGAG GCGGGCGAGT
18661 TCGACGCCGA CTTCTTCGGG ATCTCGCCGC GCGAGGCCCT CGCCATGGAC CCGCAGCAGC
18721 GGCTCCTCCT GGAGACCTCC TGGGAGGCCG TCGAGGACGC CGGGATCGAC CCGACCTCCC
18781 TTCAGGGGCA GCAGGTCGGC GTGTTCGCGG GCACCAACGG CCCCCACTAC GAGCCGCTGC
18841 TCCGCAACAC CGCCGAGGAT CTTGAGGGTT ACGTCGGGAC GGGCAACGCC GCCAGCATCA
18901 TGTCGGGCCG TGTCTCGTAC ACCCTCGGCC TGGAGGGCCC GGCCGTCACG GTCGACACCG
18961 CCTGCTCCTC CTCGCTGGTC GCCCTGCACC TCGCCGTGCA GGCCCTGCGC AAGGGCGAAT
```

-continued

DNA Sequence of the Insert DNA in Cosmid pKOS023-27 (SEQ ID 19).

```
19021 GCGGACTGGC GCTCGCGGGC GGTGTGACGG TCATGTCGAC GCCCACGACG TTCGTGGAGT
19081 TCAGCCGGCA GCGCGGGCTC GCGGAGGACG GCCGGTCGAA GGCGTTCGCC GCGTCGGCGG
19141 ACGGCTTCGG CCCGGCGGAG GGCGTCGGCA TGCTCCTCGT CGAGCGCCTG TCGGACGCCC
19201 GCCGCAACGG ACACCGTGTG CTGGCGGTCG TGCGCGGCAG CGCGGTCAAC CAGGACGGCG
19261 CGAGCAACGG CCTGACCGCC CCGAACGGGC CCTCGCAGCA GCGCGTCATC CGGCGCGCGC
19321 TCGCGGACGC CCGACTGACG ACCGCCGACG TGGACGTCGT CGAGGCCCAC GGCACGGGCA
19381 CGCGACTCGG CGACCCGATC GAGGCACAGG CCCTCATCGC CACCTACGGC CAGGGGCGCG
19441 ACACCGAACA GCCGCTGCGC CTGGGGTCGT TGAAGTCCAA CATCGGACAC ACCCAGGCCG
19501 CCGCCGGTGT CTCCGGCATC ATCAAGATGG TCCAGGCGAT GCGCCACGGC GTCCTGCCGA
19561 AGACGCTCCA CGTGGACCGG CCGTCGGACC AGATCGACTG GTCGGCGGGC ACGGTCGAGC
19621 TGCTCACCGA GGCCATGGAC TGGCCGAGGA AGCAGGAGGG CGGGCTGCGC CGCGCGGCCG
19681 TCTCCTCCTT CGGCATCAGC GGCACGAACG CGCACATCGT GCTCGAAGAA GCCCCGGTCG
19741 ACGAGGACGC CCCGGCGGAC GAGCCGTCGG TCGGCGGTGT GGTGCCGTGG CTCGTGTCCG
19801 CGAAGACTCC GGCCGCGCTG GACGCCCAGA TCGGACGCCT CGCCGCGTTC GCCTCGCAGG
19861 GCCGTACGGA CGCCGCCGAT CCGGGCGCGG TCGCTCGCGT ACTGGCCGGC GGGCGTGCGC
19921 AGTTCGAGCA CCGGGCCGTC GCGCTCGGCA CCGGACAGGA CGACCTGGCG GCCGCACTGG
19981 CCGCGCCTGA GGGTCTGGTC CGGGGTGTGG CCTCCGGTGT GGGTCGAGTG GCGTTCGTGT
20041 TCCCGGGACA GGGCACGCAG TGGGCCGGGA TGGGTGCCGA ACTCCTCGAC GTGTCGAAGG
20101 AGTTCGCGGC GGCCATGGCC GAGTGCGAGG CCGCGCTCGC TCCGTACGTG GACTGGTCGC
20161 TGGAGGCCGT CGTCCGACAG GCCCCCGGCG CGCCCACGCT GGAGCGGGTC GATGTCGTCC
20221 AGCCCGTGAC GTTCGCCGTC ATGGTCTCGC TGGCGAAGGT CTGGCAGCAC ACGGGGTGA
20281 CCCCGCAAGC CGTCGTCGGC CACTCGCAGG GCGAGATCGC CGCCGCGTAC GTCGCCGGTG
20341 CCCTGAGCCT GGACGACGCC GCTCGTGTCG TGACCCTGCG CAGCAAGTCC ATCGGCGCCC
20401 ACCTCGCGGG CCAGGGCGGC ATGCTGTCCC TCGCGCTGAG CGAGGCGGCC GTTGTGGAGC
20461 GACTGGCCGG GTTCGACGGG CTGTCCGTCG CCGCCGTCAA CGGGCCTACC GCCACCGTGG
20521 TTTCGGGCGA CCCGACCCAG ATCCAAGAGC TCGCTCAGGC GTGTGAGGCC GACGGGGTCC
20581 GCGCACGGAT CATCCCCGTC GACTACGCCT CCCACAGCGC CCACGTCGAG ACCATCGAGA
20641 GCGAACTCGC CGACGTCCTG GCGGGGTTGT CCCCCCAGAC ACCCCAGGTC CCCTTCTTCT
20701 CCACCCTCGA AGGCGCCTGG ATCACCGAAC CCGCCCTCGA CGGCGGCTAC TGGTACCGCA
20761 ACCTCCGCCA TCGTGTGGGC TTCGCCCCGG CCGTCGAAAC CCTGGCCACC GACGAAGGCT
20821 TCACCCACTT CGTCGAGGTC AGCGCCCACC CCGTCCTCAC CATGGCCCTG CCCGAGACCG
20881 TCACCGGCCT CGGCACCCTC CGCCGTGACA ACGGCGGACA GCACCGCCTC ACCACCTCCC
20941 TCGCCGAGGC CTGGGCCAAC GGCCTCACCG TCGACTGGGC CTCTCTCCTC CCCACCACGA
21001 CCACCCACCC CGATCTGCCC ACCTACGCCT TCCAGACCGA GCGCTACTGG CCGCAGCCCG
21061 ACCTCTCCGC CGCCGGTGAC ATCACCTCCG CCGGTCTCGG GCGGCCGAG CACCCGCTGC
21121 TCGGCGCGGC CGTGGCGCTC GCGGACTCCG ACGGCTGCCT GCTCACGGGG AGCCTCTCCC
21181 TCCGTACGCA CCCCTGGCTG GCGGACCACG CGGTGGCCGG CACCGTGCTG CTGCCGGGAA
21241 CGGCGTTCGT GGAGCTGGCG TTCCGAGCCG GGGACCAGGT CGGTTGCGAT CTGGTCGAGG
21301 AGCTCACCCT CGACGCGCCG CTCGTGCTGC CCCGTCGTGG CGCGGTCCGT GTGCAGCTGT
```

-continued

DNA Sequence of the Insert DNA in Cosmid pKOS023-27 (SEQ ID 19).

```
21361 CCGTCGGCGC GAGCGACGAG TCCGGGCGTC GTACCTTCGG GCTCTACGCG CACCCGGAGG

21421 ACGCGCCGGG CGAGGCGGAG TGGACGCGGC ACGCCACCGG TGTGCTGGCC GCCCGTGCGG

21481 ACCGCACCGC CCCCGTCGCC GACCCGGAGG CCTGGCCGCC GCCGGGCGCC GAGCCGGTGG

21541 ACGTGGACGG TCTGTACGAG CGCTTCGCGG CGAACGGCTA CGGCTACGGC CCCCTCTTCC

21601 AGGGCGTCCG TGGTGTCTGG CGGCGTGGCG ACGAGGTGTT CGCCGACGTG GCCCTGCCGG

21661 CCGAGGTCGC CGGTGCCGAG GGCGCGCGT TCGGCCTTCA CCCGGCGCTG CTCGACGCCG

21721 CCGTGCAGGC GGCCGGTGCG GGCGGGGCGT TCGGCGCGGG CACGCGGCTG CCGTTCGCCT

21781 GGAGCGGGAT CTCCCTGTAC GCGGTCGGCG CCACCGCCCT CCGCGTGCGG CTGGCCCCCG

21841 CCGGCCCGGA CACGGTGTCC GTGAGCGCCG CCGACTCCTC CGGGCAGCCG GTGTTCGCCG

21901 CGGACTCCCT CACGGTGCTG CCCGTCGACC CCGCGCAGCT GGCGGCCTTC AGCGACCCGA

21961 CTCTGGACGC GCTGCACCTG CTGGAGTGGA CCGCCTGGGA CGGTGCCGCG CAGGCCCTGC

22021 CCGGCGCGGT CGTGCTGGGC GGCGACGCCG ACGGTCTCGC CGCGGCGCTG CGCGCCGGTG

22081 GCACCGAGGT CCTGTCCTTC CCGGACCTTA CGGACCTGGT GGAGGCCGTC GACCGGGGCG

22141 AGACCCCGGC CCCGGCGACC GTCCTGGTGG CCTGCCCCGC CGCCGGCCCC GGTGGGCCGG

22201 AGCATGTCCG CGAGGCCCTG CACGGGTCGC TCGCGCTGAT GCAGGCCTGG CTGGCCGACG

22261 AGCGGTTCAC CGATGGGCGC CTGGTGCTCG TGACCCGCGA CGCGGTCGCC GCCCGTTCCG

22321 GCGACGGCCT GCGGTCCACG GGACAGGCCG CCGTCTGGGG CCTCGGCCGG TCCGCGCAGA

22381 CGGAGAGCCC GGGCCGGTTC GTCCTGCTCG ACCTCGCCGG GGAAGCCCGG ACGGCCGGGG

22441 ACGCCACCGC CGGGGACGGC CTGACGACCG GGACGCCAC CGTCGGCGG ACCTCTGGAG

22501 ACGCCGCCCT CGGCAGCGCC CTCGCGACCG CCCTCGGCTC GGGCGAGCCG CAGCTCGCCC

22561 TCCGGGACGG GGCGCTCCTC GTACCCCGCC TGGCGCGGGC CGCCGCGCCC GCCGCGGCCG

22621 ACGGCCTCGC CGCGGCCGAC GGCCTCGCCG CTCTGCCGCT GCCCGCCGCT CCGGCCCTCT

22681 GGCGTCTGGA GCCCGGTACG GACGGCAGCC TGGAGAGCCT CACGGCGGCG CCCGGCGACG

22741 CCGAGACCCT CGCCCCGGAG CCGCTCGGCC CGGGACAGGT CCGCATCGCG ATCCGGGCCA

22801 CCGGTCTCAA CTTCCGCGAC GTCCTGATCG CCCTCGGCAT GTACCCCGAT CCGGCGCTGA

22861 TGGGCACCGA GGGAGCCGGC GTGGTCACCG CGACCGGCCC CGGCGTCACG CACCTCGCCC

22921 CCGGCGACCG GGTCATGGGC CTGCTCTCCG GCGCGTACGC CCCGGTCGTC GTGGCGGACG

22981 CGCGGACCGT CGCGCGGATG CCCGAGGGGT GGACGTTCGC CCAGGGCGCC TCCGTGCCGG

23041 TGGTGTTCCT GACGGCCGTC TACGCCCTGC GCGACCTGGC GGACGTCAAG CCCGGCGAGC

23101 GCCTCCTGGT CCACTCCGCC GCCGGTGGCG TGGGCATGGC CGCCGTGCAG CTCGCCCGGC

23161 ACTGGGGCGT GGAGGTCCAC GGCACGGCGA GTCACGGGAA GTGGACGCC CTGCGCGCGC

23221 TCGGCCTGGA CGACGCGCAC ATCGCCTCCT CCCGCACCCT GGACTTCGAG TCCGCGTTCC

23281 GTGCCGCTTC CGGCGGGGCG GGCATGGACG TCGTACTGAA CTCGCTCGCC CGCGAGTTCG

23341 TCGACGCCTC GCTGCGCCTG CTCGGGCCGG GCGGCCGGTT CGTGGAGATG GGGAAGACCG

23401 ACGTCCGCGA CGCGGAGCGG GTCGCCGCCG ACCACCCGG TGTCGGCTAC CGCGCCTTCG

23461 ACCTGGGCGA GGCCGGGCCG GAGCGGATCG GCGAGATGCT CGCCGAGGTC ATCGCCCTCT

23521 TCGAGGACGG GGTGCTCCGG CACCTGCCCG TCACGACCTG GACGTGCGC CGGGCCCGCG

23581 ACGCCTTCCG GCACGTCAGC CAGGCCCGCC ACACGGGCAA GTCGTCCTC ACGATGCCGT
```

-continued

DNA Sequence of the Insert DNA in Cosmid pKOS023-27 (SEQ ID 19).

```
23641  CGGGCCTCGA CCCGGAGGGT ACGGTCCTGC TGACCGGCGG CACCGGTGCG CTGGGGGGCA
23701  TCGTGGCCCG GCACGTGGTG GGCGAGTGGG GCGTACGACG CCTGCTGCTC GTGAGCCGGC
23761  GGGGCACGGA CGCCCCGGGC GCCGGCGAGC TCGTGCACGA GCTGGAGGCC CTGGGAGCCG
23821  ACGTCTCGGT GGCCGCGTGC GACGTCGCCG ACCGCGAAGC CCTCACCGCC GTACTCGACT
23881  CGATCCCCGC CGAACACCCG CTCACCGCGG TCGTCCACAC GGCAGGCGTC CTCTCCGACG
23941  GCACCCTCCC CTCGATGACA GCGGAGGATG TGGAACACGT ACTGCGTCCC AAGGTCGACG
24001  CCGCGTTCCT CCTCGACGAA CTCACCTCGA CGCCCGGCTA CGACCTGGCA GCGTTCGTCA
24061  TGTTCTCCTC CGCCGCCGCC GTCTTCGGTG GCGCGGGGCA GGGCGCCTAC GCCGCCGCCA
24121  ACGCCACCCT CGACGCCCTC GCCTGGCGCC GCCGGACAGC CGGACTCCCC GCCCTCTCCC
24181  TCGGCTGGGG CCTCTGGGCC GAGACCAGCG GCATGACCGG CGGACTCAGC GACACCGACC
24241  GCTCGCGGCT GGCCCGTTCC GGGGCGACGC CCATGGACAG CGAGCTGACC CTGTCCCTCC
24031  TGGACGCGGC CATGCGCCGC GACGACCCGG CGCTCGTCCC GATCGCCCTG GACGTCGCCG
24361  CGCTCCGCGC CCAGCAGCGC GACGGCATGC TGGCGCCGCT GCTCAGCGGG CTCACCCGCG
24421  GATCGCGGGT CGGCGGCGCG CCGGTCAACC AGCGCAGGGC AGCCGCCGGA GGCGCGGGCG
24481  AGGCGGACAC GGACCTCGGC GGGCGGCTCG CCGCGATGAC ACCGGACGAC CGGGTCGCGC
24541  ACCTGCGGGA CCTCGTCCGT ACGCACGTGG CGACCGTCCT GGGACACGGC ACCCCGAGCC
24601  GGGTGGACCT GGAGCGGGCC TTCCGCGACA CCGGTTTCGA CTCGCTCACC GCCGTCGAAC
24661  TCCGCAACCG TCTCAACGCC GCGACCGGGC TGCGGCTGCC GGCCACGCTG GTCTTCGACC
24721  ACCCCACCCC GGGGGAGCTC GCCGGGCACC TGCTCGACGA ACTCGCCACG GCCGCGGGCG
24781  GGTCCTGGGC GGAAGGCACC GGGTCCGGAG ACACGGCCTC GGCGACCGAT CGGCAGACCA
24841  CGGCGGCCCT CGCCGAACTC GACCGGCTGG AAGGCGTGCT CGCCTCCCTC GCGCCCGCCG
24901  CCGGCGGCCG TCCGGAGCTC GCCGCCCGGC TCAGGGCGCT GGCCGCGGCC CTGGGGGACG
24961  ACGGCGACGA CGCCACCGAC CTGGACGAGG CGTCCGACGA CGACCTCTTC TCCTTCATCG
25021  ACAAGGAGCT GGGCGACTCC GACTTCTGAC CTGCCCGACA CCACCGGCAC CACCGGCACC
25081  ACCAGCCCCC CTCACACACG GAACACGGAA CGGACAGGCG AGAACGGGAG CCATGGCGAA
25141  CAACGAAGAC AAGCTCCGCG ACTACCTCAA GCGCGTCACC GCCGAGCTGC AGCAGAACAC
25201  CAGGCGTCTG CGCGAGATCG AGGGACGCAC GCACGAGCCG GTGGCGATCG TGGGCATGGC
25261  CTGCCGCCTG CCGGGCGGTG TCGCCTCGCC CGAGGACCTG TGGCAGCTGG TGGCCGGGGA
25321  CGGGGACGCG ATCTCGGAGT TCCCGCAGGA CCGCGGCTGG ACGTGGAGG GGCTGTACGA
25381  CCCCGACCCG GACGCGTCCG GCAGGACGTA CTGCCGGTCC GGCGGATTCC TGCACGACGC
25441  CGGCGAGTTC GACGCCGACT TCTTCGGGAT CTCGCCGCGC GAGGCCCTCG CCATGGACCC
25501  GCAGCAGCGA CTGTCCCTCA CCACCGCGTG GGAGGCGATC GAGAGCGCGG GCATCGACCC
25561  GACGGCCCTG AAGGGCAGCG GCCTCGGCGT CTTCGTCGGC GGCTGGCACA CCGGCTACAC
25621  CTCGGGGCAG ACCACCGCCG TGCAGTCGCC CGAGCTGGAG GGCCACCTGG TCAGCGGCGC
25681  GGCGCTGGGC TTCCTGTCCG GCCGTATCGC GTACGTCCTC GGTACGGACG GACCGGCCCT
25741  GACCGTGGAC ACGGCCTGCT CGTCCTCGCT GGTCGCCCTG CACCTCGCCG TGCAGGCCCT
25801  CCGCAAGGGC GAGTGCGACA TGGCCCTCGC CGGTGGTGTC ACGGTCATGC CCAACGCGGA
25861  CCTGTTCGTG CAGTTCAGCC GGCAGCGCGG GCTGGCCGCG GACGGCCGGT CGAAGGCGTT
25921  CGCCACCTCG GCGGACGGCT TCGGCCCCGC GGAGGGCGCC GGAGTCCTGC TGGTGGAGCG
```

-continued

DNA Sequence of the Insert DNA in Cosmid pKOS023-27 (SEQ ID 19).

```
25981  CCTGTCGGAC GCCCGCCGCA ACGGACACCG GATCCTCGCG GTCGTCCGCG GCAGCGCGGT
26041  CAACCAGGAC GGCGCCAGCA ACGGCCTCAC GGCTCCGCAC GGGCCCTCCC AGCAGCGCGT
26101  CATCCGACGG GCCCTGGCGG ACGCCCGGCT CGCGCCGGGT GACGTGGACG TCGTCGAGGC
26161  GCACGGCACG GGCACGCGGC TCGGCGACCC GATCGAGGCG CAGGCCCTCA TCGCCACCTA
26221  CGGCCAGGAG AAGAGCAGCG AACAGCCGCT GAGGCTGGGC GCGTTGAAGT CGAACATCGG
26281  GCACACGCAG GCCGCGGCCG GTGTCGCAGG TGTCATCAAG ATGGTCCAGG CGATGCGCCA
26341  CGGACTGCTG CCGAAGACGC TGCACGTCGA CGAGCCCTCG GACCAGATCG ACTGGTCGGC
26401  GGGCACGGTG GAACTCCTCA CCGAGGCCGT CGACTGGCCG GAGAAGCAGG ACGGCGGGCT
26461  GCGCCGCGCG GCTGTCTCCT CCTTCGGCAT CAGCGGGACG AACGCGCACG TCGTCCTGGA
26521  GGAGGCCCCG GCGGTCGAGG ACTCCCCGGC CGTCGAGCCG CCGGCCGGTG GCGGTGTGGT
26581  GCCGTGGCCG GTGTCCGCGA AGACTCCGGC CGCGCTGGAC GCCCAGATCG GGCAGCTCGC
26641  CGCGTACGCG GACGGTCGTA CGGACGTGGA TCCGGCGGTG GCCGCCCGCG CCCTGGTCGA
26701  CAGCCGTACG GCGATGGAGC ACCGCGCGGT CGCGGTCGGC GACAGCCGGG AGGCACTGCG
26761  GGACGCCCTG CGGATGCCGG AAGGACTGGT ACGCGGCACG TCCTCGGACG TGGGCCGGGT
26821  GGCGTTCGTC TTCCCCGGCC AGGGCACGCA GTGGGCCGGC ATGGGCGCCG AACTCCTTGA
26881  CAGCTCACCG GAGTTCGCTG CCTCGATGGC CGAATGCGAG ACCGCGCTCT CCCGCTACGT
26941  CGACTGGTCT CTTGAAGCCG TCGTCCGACA GGAACCCGGC GCACCCACGC TCGACCGCGT
27001  CGACGTCGTC CAGCCCGTGA CCTTCGCTGT CATGGTCTCG CTGGCGAAGG TCTGGCAGCA
27061  CCACGGCATC ACCCCCCAGG CCGTCGTCGG CCACTCGCAG GGCGAGATCG CCGCCGCGTA
27121  CGTCGCCGGT GCACTCACCC TCGACGACGC CGCCCGCGTC GTCACCCTGC GCAGCAAGTC
27181  CATCGCCGCC CACCTCGCCG GCAAGGGCGG CATGATCTCC CTCGCCCTCG ACGAGGCGGC
27241  CGTCCTGAAG CGACTGAGCG ACTTCGACGG ACTCTCCGTC GCCGCCGTCA ACGGCCCCAC
27301  CGCCACCGTC GTCTCCGGCG ACCCGACCCA GATCGAGGAA CTCGCCCGCA CCTGCGAGGC
27361  CGACGGCGTC CGTGCGCGGA TCATCCCGGT CGACTACGCC TCCCACAGCC GGCAGGTCGA
27421  GATCATCGAG AAGGAGCTGG CCGAGGTCCT CGCCGGACTC GCCCCGCAGG CTCCGCACGT
27481  GCCGTTCTTC TCCACCCTCG AAGGCACCTG GATCACCGAG CCGGTGCTCG ACGGCACCTA
27541  CTGGTACCGC AACCTGCGCC ATCGCGTGGG CTTCGCCCCC GCCGTGGAGA CCTTGGCGGT
27601  TGACGGCTTC ACCCACTTCA TCGAGGTCAG CGCCCACCCC GTCCTCACCA TGACCCTCCC
27661  CGAGACCGTC ACCGGCCTCG GCACCCTCCG CCGCGAACAG GGAGGCCAGG AGCGTCTGGT
27721  CACCTCACTC GCCGAAGCCT GGGCCAACGG CCTCACCATC GACTGGGCGC CCATCCTCCC
27781  CACCGCAACC GGCCACCACC CCGAGCTCCC CACCTACGCC TTCCAGACCG AGCGCTTCTG
27841  GCTGCAGAGC TCCGCGCCCA CCAGCGCCGC CGACGACTGG CGTTACCGCG TCGAGTGGAA
27901  GCCGCTGACG GCCTCCGGCC AGGCGGACCT GTCCGGGCGG TGGATCGTCG CCGTCGGGAG
27961  CGAGCCAGAA GCCGAGCTGC TGGGCGCGCT GAAGGCCGCG GGAGCGGAGG TCGACGTACT
28021  GGAAGCCGGG GCGGACGACG ACCGTGAGGC CCTCGCCGCC CGGCTCACCG CACTGACGAC
28081  CGGCGACGGC TTCACCGGCG TGGTCTCGCT CCTCGACGAC CTCGTGCCAC AGGTCGCCTG
28141  GGTGCAGGCA CTCGGCGACG CCGGAATCAA GGCGCCCCTG TGGTCCGTCA CCCAGGGCGC
28201  GGTCTCCGTC GGACGTCTCG ACACCCCCGC CGACCCCGAC CGGGCCATGC TCTGGGGCCT
```

-continued

DNA Sequence of the Insert DNA in Cosmid pKOS023-27 (SEQ ID 19).

```
28261 CGGCCGCGTC GTCGCCCTTG AGCACCCCGA ACGCTGGGCC GGCCTCGTCG ACCTCCCCGC
28321 CCAGCCCGAT GCCGCCGCCC TCGCCCACCT CGTCACCGCA CTCTCCGGCG CCACCGGCGA
28381 GGACCAGATC GCCATCCGCA CCACCGGACT CCACGCCCGC CGCCTCGCCC GCGCACCCCT
28441 CCACGGACGT CGGCCCACCC GCGACTGGCA GCCCCACGGC ACCGTCCTCA TCACCGGCGG
28501 CACCGGAGCC CTCGGCAGCC ACGCCGCACG CTGGATGGCC CACCACGGAG CCGAACACCT
28561 CCTCCTCGTC AGCCGCAGCG GCGAACAAGC CCCCGGAGCC ACCCAACTCA CCGCCGAACT
28621 CACCGCATCG GGCGCCCGCG TCACCATCGC CGCCTGCGAC GTCGCCGACC CCCACGCCAT
28681 GCGCACCCTC CTCGACGCCA TCCCCGCCGA GACGCCCCTC ACCGCCGTCG TCCACACCGC
28741 CGGCGCACCG GCGGCGATC CGCTGGACGT CACCGGCCCG GAGGACATCG CCCGCATCCT
28801 GGGCGCGAAG ACGAGCGGCG CCGAGGTCCT CGACGACCTG CTCCGCGGCA CTCCGCTGGA
28861 CGCCTTCGTC CTCTACTCCT CGAACGCCGG GGTCTGGGC AGCGGCAGCC AGGGCGTCTA
28921 CGCGGCGGCC AACGCCCACC TCGACGCGCT CGCCGCCCGG CGCCGCGCCC GGGGCGAGAC
28981 GGCGACCTCG GTCGCCTGGG GCCTCTGGGC CGGCGACGGC ATGGGCCGGG GCGCCGACGA
29041 CGCGTACTGG CAGCGTCGCG GCATCCGTCC GATGAGCCCC GACCGCGCCC TGGACGAACT
29101 GGCCAAGGCC CTGAGCCACG ACGAGACCTT CGTCGCCGTG GCCGATGTCG ACTGGGAGCG
29161 GTTCGCGCCC GCGTTCACGG TGTCCCGTCC CAGCCTTCTG CTCGACGGCG TCCCGGAGGC
29221 CCGGCAGGCG CTCGCCGCAC CCGTCGGTGC CCCGGCTCCC GGCGACGCCG CCGTGGCGCC
29281 GACCGGGCAG TCGTCGGCGC TGGCCGCGAT CACCGCGCTC CCCGAGCCCG AGCGCCGGCC
29341 GGCGCTCCTC ACCCTCGTCC GTACCCACGC GGCGGCCGTA CTCGGCCATT CCTCCCCCGA
29401 CCGGGTGGCC CCCGGCCGTG CCTTCACCGA GCTCGGCTTC GACTCGCTGA CGGCCGTGCA
29461 GCTCCGCAAC CAGCTCTCCA CGGTGGTCGG CAACAGGCTC CCCGCCACCA CGGTCTTCGA
29521 CCACCCGACG CCCGCCGCAC TCGCCGCGCA CCTCCACGAG GCGTACCTCG CACCGGCCGA
29581 GCCGGCCCCG ACGGACTGGG AGGGGCGGGT GCGCCGGGCC CTGGCCGAAC TGCCCCTCGA
29641 CCGGCTGCGG GACGCGGGGG TCCTCGACAC CGTCCTGCGC CTCACCGGCA TCGAGCCCGA
29701 GCCGGGTTCC GGCGGTTCGG ACGGCGGCGC CGCCGACCCT GGTGCGGAGC CGGAGGCGTC
29761 GATCGACGAC CTGGACGCCG AGGCCCTGAT CCGGATGGCT CTCGGCCCCC GTAACACCTG
29821 ACCCGACCGC GGTCCTGCCC CACGCGCCGC ACCCCGCGCA TCCCGCGCAC CACCCGCCCC
29881 CACACGCCCA CAACCCCATC CACGAGCGGA AGACCACACC CAGATGACGA GTTCCAACGA
29941 ACAGTTGGTG GACGCTCTGC GCGCCTCTCT CAAGGAGAAC GAAGAACTCC GGAAAGAGAG
30001 CCGTCGCCGG GCCGACCGTC GGCAGGAGCC CATGGCGATC GTCGGCATGA GCTGCCGGTT
30061 CGCGGGCGGA ATCCGGTCCC CCGAGGACCT CTGGGACGCC GTCGCCGCGG GCAAGGACCT
30121 GGTCTCCGAG GTACCGGAGG AGCGCGGCTG GGACATCGAC TCCCTCTACG ACCCGGTGCC
30181 CGGGCGCAAG GGCACGACGT ACGTCCGCAA CGCCGCGTTC CTCGACGACG CCGCCGGATT
30241 CGACGCGGCC TTCTTCGGGA TCTCGCCGCG CGAGGCCCTC GCCATGGACC CGCAGCAGCG
30301 GCAGCTCCTC GAAGCCTCCT GGGAGGTCTT CGAGCGGGCC GGCATCGACC CCGCGTCGGT
30361 CCGCGGCACC GACGTCGGCG TGTACGTGGG CTGTGGCTAC CAGGACTACG CGCCGGACAT
30421 CCGGGTCGCC CCCGAAGGCA CCGGCGGTTA CGTCGTCACC GGCAACTCCT CCGCCGTGGC
30481 CTCCGGGCGC ATCGCGTACT CCCTCGGCCT GGAGGGACCC GCCGTGACCG TGGACACGGC
30541 GTGCTCCTCT TCGCTCGTCG CCCTGCACCT CGCCCTGAAG GGCCTGCGGA ACGGCGACTG
```

-continued

DNA Sequence of the Insert DNA in Cosmid pKOS023-27 (SEQ ID 19).

```
30601 CTCGACGGCA CTCGTGGGCG GCGTGGCCGT CCTCGCGACG CCGGGCGCGT TCATCGAGTT
30661 CAGCAGCCAG CAGGCCATGG CCGCCGACGG CCGGACCAAG GGCTTCGCCT CGGCGGCGGA
30721 CGGCCTCGCC TGGGGCGAGG GCGTCGCCGT ACTCCTCCTC GAACGGCTCT CCGACGCGCG
30781 GCGCAAGGGC CACCGGGTCC TGGCCGTCGT GCGCGGCAGC GCCATCAACC AGGACGGCGC
30841 GAGCAACGGC CTCACGGCTC CGCACGGGCC CTCCCAGCAG CGCCTGATCC GCCAGGCCCT
30901 GGCCGACGCG CGGCTCACGT CGAGCGACGT GGACGTCGTG GAGGGCCACG GCACGGGGAC
30961 CCGTCTCGGC GACCCGATCG AGGCGCAGGC GCTGCTCGCC ACGTACGGGC AGGGGCGCGC
31021 CCCGGGGCAG CCGCTGCGGC TGGGGACGCT GAAGTCGAAC ATCGGGCACA CGCAGGCCGC
31081 TTCGGGTGTC GCCGGTGTCA TCAAGATGGT GCAGGCGCTG CGCCACGGGG TGCTGCCGAA
31141 GACCCTGCAC GTGGACGAGC CGACGGACCA GGTCGACTGG TCGGCCGGTT CGGTCGAGCT
31201 GCTCACCGAG GCCGTGGACT GGCCGGAGCG GCCGGGCCGG CTCCGCCGGG CGGGCGTCTC
31261 CGCGTTCGGC GTGGGCGGGA CGAACGCGCA CGTCGTCCTG GAGGAGGCCC CGGCGGTCGA
31321 GGAGTCCCCT GCCGTCGAGC CGCCGGCCGG TGGCGGCGTG GTGCCGTGGC CGGTGTCCGC
31381 GAAGACCTCG GCCGCACTGG ACGCCCAGAT CGGGCAGCTC GCCGCATACG CGGAAGACCG
31441 CACGGACGTG GATCCGGCGG TGGCCGCCCG CGCCCTGGTC GACAGCCGTA CGGCGATGGA
31501 GCACCGCGCG GTCGCGGTCG GCGACAGCCG GGAGGCACTG CGGGACGCCC TGCGGATGCC
31561 GGAAGGACTG GTACGGGGCA CGGTCACCGA TCCGGGCCGG GTGGCGTTCG TCTTCCCCGG
31621 CCAGGGCACG CAGTGGGCCG GCATGGGCGC CGAACTCCTC GACAGCTCAC CCGAATTCGC
31681 CGCCGCCATG GCCGAATGCG AGACCGCACT CTCCCCGTAC GTCGACTGGT CTCTCGAAGC
31741 CGTCGTCCGA CAGGCTCCCA GCGCACCGAC ACTCGACCGC GTCGACGTCG TCCAGCCCGT
31801 CACCTTCGCC GTCATGGTCT CCCTCGCCAA GGTCTGGCAG CACCACGGCA TCACCCCCGA
31861 GGCCGTCATC GGCCACTCCC AGGGCGAGAT CGCCGCCGCG TACGTCGCCG GTGCCCTCAC
31921 CCTCGACGAC GCCGCTCGTG TCGTGACCCT CCGCAGCAAG TCCATCGCCG CCCACCTCGC
31981 CGGCAAGGGC GGCATGATCT CCCTCGCCCT CAGCGAGGAA GCCACCCGGC AGCGCATCGA
32041 GAACCTCCAC GGACTGTCGA TCGCCGCCGT CAACGGGCCT ACCGCCACCG TGGTTTCGGG
32101 CGACCCCACC CAGATCCAAG AACTTGCTCA GGCGTGTGAG GCCGACGGCA TCCGCGCACG
32161 GATCATCCCC GTCGACTACG CCTCCCACAG CGCCCACGTC GAGACCATCG AGAACGAACT
32221 CGCCGACGTC CTGGCGGGGT TGTCCCCCCA GACACCCCAG GTCCCCTTCT TCTCCACCCT
32281 CGAAGGCACC TGGATCACCG AACCCGCCCT CGACGGCGGC TACTGGTACC GCAACCTCCG
32341 CCATCGTGTG GGCTTCGCCC CGGCCGTCGA GACCCTCGCC ACCGACGAAG CTTCACCCA
32401 CTTCATCGAG GTCAGCGCCC ACCCCGTCCT CACCATGACC CTCCCCGACA AGGTCACCGG
32461 CCTGGCCACC CTCCGACGCG AGGACGGCGG ACAGCACCGC CTCACCACCT CCCTTGCCGA
32521 GGCCTGGGCC AACGGCCTCG CCCTCGACTG GCCTCCCTC CTGCCCGCCA CGGGCGCCCT
32581 CAGCCCCGCC GTCCCCGACC TCCCGACGTA CGCCTTCCAG CACCGCTCGT ACTGGATCAG
32641 CCCCGCGGGT CCCGGCGAGG CGCCCGCGCA CACCGCTTCC GGGCGCGAGG CCGTCGCCGA
32701 GACGGGCTC GCGTGGGGCC CGGGTGCCGA GGACCTCGAC GAGGAGGGCC GGCGCAGCGC
32761 CGTACTCGCG ATGGTGATGC GGCAGGCGGC CTCCGTGCTC CGGTGCGACT CGCCCGAAGA
32821 GGTCCCCGTC GACCGCCCGC TGCGGGAGAT CGGCTTCGAC TCGCTGACCG CCGTCGACTT
```

-continued

DNA Sequence of the Insert DNA in Cosmid pKOS023-27 (SEQ ID 19).

```
32881  CCGCAACCGC GTCAACCGGC TGACCGGTCT CCAGCTGCCG CCCACCGTCG TGTTCGAGCA
32941  CCCGACGCCC GTCGCGCTCG CCGAGCGCAT CAGCGACGAG CTGGCCGAGC GGAACTGGGC
33001  CGTCGCCGAG CCGTCGGATC ACGAGCAGGC GGAGGAGGAG AAGGCCGCCG CTCCGGCGGG
33061  GGCCCGCTCC GGGGCCGACA CCGGCGCCGG CGCCGGGATG TTCCGCGCCC TGTTCCGGCA
33121  GGCCGTGGAG GACGACCGGT ACGGCGAGTT CCTCGACGTC CTCGCCGAAG CCTCCGCGTT
33181  CCGCCCGCAG TTCGCCTCGC CCGAGGCCTG CTCGGAGCGG CTCGACCCGT GCTGCTCGC
33241  CGGCGGTCCG ACGGACCGGG CGGAAGGCCG TGCCGTTCTC GTCGGCTGCA CCGGCACCGC
33301  GGCGAACGGC GGCCCGCACG AGTTCCTGCG GCTCAGCACC TCCTTCCAGG AGGAGCGGGA
33361  CTTCCTCGCC GTACCTCTCC CCGGCTACGG CACGGGTACG GGCACCGGCA CGGCCCTCCT
33421  CCCGGCCGAT CTCGACACCG CGCTCGACGC CCAGGCCCGG GCGATCCTCC GGGCCGCCGG
33481  GGACGCCCCG GTCGTCCTGC TCGGGCACTC CGGCGGCGCC CTGCTCGCGC ACGAGCTGGC
33541  CCTCCGCCTG GAGCGGGCGC ACGGCGCGCC GCCGGCCGGG ATCGTCCTGG TCGACCCCTA
33601  TCCGCCGGGC CATCAGGAGC CCATCGAGGT GTGGAGCAGG CAGCTGGGCG AGGGCCTGTT
33661  CGCGGGCGAG CTGGAGCCGA TGTCCGATGC GCGGCTGCTG GCCATGGGCC GGTACGCGCG
33721  GTTCCTCGCC GGCCCGCGGC CGGGCCGCAG CAGCGCGCCC GTGCTTCTGG TCCGTGCCTC
33781  CGAACCGCTG GGCGACTGGC AGGAGGAGCG GGGCGACTGG CGTGCCCACT GGGACCTTCC
33841  GCACACCGTC GCGGACGTGC CGGGCGACCA CTTCACGATG ATGCGGGACC ACGCGCCGGC
33901  CGTCGCCGAG CCGTCCTCT CCTGGCTCGA CGCCATCGAG GGCATCGAGG GGGCGGGCAA
33961  GTGACCGACA GACCTCTGAA CGTGGACAGC GGACTGTGGA TCCGGCGCTT CCACCCCGCG
34021  CCGAACAGCG CGGTGCGGCT GGTCTGCCTG CCGCACGCCG GCGGCTCCGC CAGCTACTTC
34081  TTCCGCTTCT CGGAGGAGCT GCACCCCTCC GTCGAGGCCC TGTCGGTGCA GTATCCGGGC
34141  CGCCAGGACC GGCGTGCCGA GCCGTGTCTG GAGAGCGTCG AGGAGCTCGC CGAGCATGTG
34201  GTCGCGGCCA CCGAACCCTG GTGGCAGGAG GGCCGGCTGG CCTTCTTCGG GCACAGCCTC
34261  GGCGCCTCCG TCGCCTTCGA GACGGCCCGC ATCCTGGAAC AGCGGCACGG GGTACGGCCC
34321  GAGGGCCTGT ACGTCTCCGG TCGGCGCGCC CCGTCGCTGG CGCCGGACCG GCTCGTCCAC
34381  CAGCTGGACG ACCGGGCGTT CCTGGCCGAG ATCCGGCGGC TCAGCGGCAC CGACGAGCGG
34441  TTCCTCCAGG ACGACGAGCT GCTGCGGCTG GTGCTGCCCG CGCTGCGCAG CGACTACAAG
34501  GCGGCGGAGA CGTACCTGCA CCGGCCGTCC GCCAAGCTCA CCTGCCCGGT GATGGCCCTG
34561  GCCGGCGACC GTGACCCGAA GGCGCCGCTG AACGAGGTGG CCGAGTGGCG TCGGCACACC
34621  AGCGGGCCGT TCTGCCTCCG GGCGTACTCC GGCGGCCACT TCTACCTCAA CGACCAGTGG
34681  CACGAGATCT GCAACGACAT CTCCGACCAC CTGCTCGTCA CCCGCGGCGC GCCCGATGCC
34741  CGCGTCGTGC AGCCCCCGAC CAGCCTTATC GAAGGAGCGG CGAAGAGATG CAGAACCCA
34801  CGGTGACCGA CGACCTGACG GGGGCCCTCA CGCAGCCCCC GCTGGGCCGC ACCGTCCGCG
34861  CGGTGGCCGA CCGTGAACTC GGCACCCACC TCCTGGAGAC CCGCGGCATC CACTGGATCC
34921  ACGCCGCGAA CGGCGACCCG TACGCCACCG TGCTGCGCGG CCAGGCGGAC GACCCGTATC
34981  CCGCGTACGA GCGGGTGCGT GCCCGCGGCG CGCTCTCCTT CAGCCCGACG GGCAGCTGGG
35041  TCACCGCCGA TCACGCCCTG GCGGCGAGCA TCCTCTGCTC GACGGACTTC GGGGTCTCCG
35101  GCGCCGACGG CGTCCCGGTG CCGCAGCAGG TCCTCTCGTA CGGGGAGGGC TGTCCGCTGG
35161  AGCGCGAGCA GGTGCTGCCG GCGGCCGGTG ACGTGCCGGA GGGCGGGCAG CGTGCCGTGG
```

-continued

DNA Sequence of the Insert DNA in Cosmid pKOS023-27 (SEQ ID 19).

```
35221 TCGAGGGGAT CCACCGGGAG ACGCTGGAGG GTCTCGCGCC GGACCCGTCG GCGTCGTACG
35281 CCTTCGAGCT GCTGGGCGGT TTCGTCCGCC CGGCGGTGAC GGCCGCTGCC GCCGCCGTGC
35341 TGGGTGTTCC CGCGGACCGG CGCGCGGACT TCGCGGATCT GCTGGAGCGG CTCCGGCCGC
35401 TGTCCGACAG CCTGCTGGCC CCGCAGTCCC TGCGGACGGT ACGGGCGGCG GACGGCGCGC
35461 TGGCCGAGCT CACGGCGCTG CTCGCCGATT CGGACGACTC CCCCGGGGCC CTGCTGTCGG
35521 CGCTCGGGGT CACCGCAGCC GTCCAGCTCA CCGGGAACGC GGTGCTCGCG CTCCTCGCGC
35581 ATCCCGAGCA GTGGCGGGAG CTGTGCGACC GGCCCGGGCT CGCGGCGGCC GCGGTGGAGG
35641 AGACCCTCCG CTACGACCCG CCGGTGCAGC TCGACGCCCG GGTGGTCCGG GGGGAGACGG
35701 AGCTGGCGGG CCGGCGGCTG CCGGCCGGGG CGCATGTCGT CGTCCTGACC GCCGCGACCG
35761 GCCGGGACCC GGAGGTCTTC ACGGACCCGG AGCGCTTCGA CCTCGCGCGC CCCGACGCCG
35821 CCGCGCACCT CGCGCTGCAC CCCGCCGGTC CGTACGGCCC GGTGGCGTCC CTGGTCCGGC
35881 TTCAGGCGGA GGTCGCGCTG CGGACCCTGG CCGGGCGTTT CCCCGGGCTG CGGCAGGCGG
35941 GGGACGTGCT CCGCCCCCGC CGCGCGCCTG TCGGCCGCGG GCCGCTGAGC GTCCCGGTCA
36001 GCAGCTCCTG AGACACCGGG GCCCCGGTCC GCCCGGCCCC CCTTCGGACG GACCGGACGG
36061 CTCGGACCAC GGGGACGGCT CAGACCGTCC CGTGTGTCCC CGTCCGGCTC CCGTCCGCCC
36121 CATCCCGCCC CTCCACCGGC AAGGAAGGAC ACGACGCCAT GCGCGTCCTG CTGACCTCGT
36181 TCGCACATCA CACGCACTAC TACGGCCTGG TGCCCCTGGC CTGGGCGCTG CTCGCCGCCG
36241 GCACGAGGT GCGGGTCGCC AGCCAGCCCG CGCTCACGGA CACCATCACC GGGTCCGGGC
36301 TCGCCGCGGT GCCGGTCGGC ACCGACCACC TCATCCACGA GTACCGGGTG CGGATGGCGG
36361 GCGAGCCGCG CCCGAACCAT CCGGCGATCG CCTTCGACGA GGCCCGTCCC GAGCCGCTGG
36421 ACTGGGACCA CGCCCTCGGC ATCGAGGCGA TCCTCGCCCC GTACTTCTAT CTGCTCGCCA
36481 ACAACGACTC GATGGTCGAC GACCTCGTCG ACTTCGCCCG GTCCTGGCAG CCGGACCTGG
36541 TGCTGTGGGA GCCGACGACC TACGCGGGCG CCGTCGCCGC CCAGGTCACC GGTGCCGCGC
36601 ACGCCCGGGT CCTGTGGGGG CCCGACGTGA TGGGCAGCGC CCGCCGCAAG TTCGTCGCGC
36661 TGCGGGACCG GCAGCCGCCC GAGCACCGCG AGGACCCCAC CGCGGAGTGG CTGACGTGGA
36721 CGCTCGACCG GTACGGCGCC TCCTTCGAAG AGGAGCTGCT CACCGGCCAG TTCACGATCG
36781 ACCCGACCCC GCCGAGCCTG CGCCTCGACA CGGGCCTGCC GACCGTCGGG ATGCGTTATG
36841 TTCCGTACAA CGGCACGTCG GTCGTGCCGG ACTGGCTGAG TGAGCCGCCC GCGCGGCCCC
36901 GGGTCTGCCT GACCCTCGGC GTCTCCGCGC GTGAGGTCCT CGGCGGCGAC GGCGTCTCGC
36961 AGGGCGACAT CCTGGAGGCG CTCGCCGACC TCGACATCGA GCTCGTCGCC ACGCTCGACG
37021 CGAGTCAGCG CGCCGAGATC CGCAACTACC GAAGCACAC CCGGTTCACG GACTTCGTGC
37081 CGATGCACGC GCTCCTGCCG AGCTGCTCGG CGATCATCCA CCACGGCGGG GCGGGCACCT
37141 ACGCGACCGC CGTGATCAAC GCGGTGCCGC AGGTCATGCT CGCCGAGCTG TGGGACGCGC
37201 CGGTCAAGGC GCGGGCCGTC GCCGAGCAGG GGGCGGGGTT CTTCCTGCCG CCGGCCGAGC
37261 TCACGCCGCA GGCCGTGCGG GACGCCGTCG TCCGCATCCT CGACGACCCC TCGGTCGCCA
37321 CCGCCGCGCA CCGGCTGCGC GAGGAGACCT TCGGCGACCC CACCCCGGCC GGGATCGTCC
37381 CCGAGCTGGA GCGGCTCGCC GCGCAGCACC GCCGCCCGCC GGCCGACGCC CGGCACTGAG
37441 CCGCACCCCT CGCCCCAGGC CTCACCCCTG TATCTGCGCC GGGGACGCC CCCGGCCCAC
```

-continued

DNA Sequence of the Insert DNA in Cosmid pKOS023-27 (SEQ ID 19).

```
37501 CCTCCGAAAG ACCGAAAGCA GGAGCACCGT GTACGAAGTC GACCACGCCG ACGTCTACGA
37561 CCTCTTCTAC CTGGGTCGCG GCAAGGACTA CGCCGCCGAG GCCTCCGACA TCGCCGACCT
37621 GGTGCGCTCC CGTACCCCCG AGGCCTCCTC GCTCCTGGAC GTGGCCTGCG GTACGGGCAC
37681 GCATCTGGAG CACTTCACCA AGGAGTTCGG CGACACCGCC GGCCTGGAGC TGTCCGAGGA
37741 CATGCTCACC CACGCCCGCA AGCGGCTGCC CGACGCCACG CTCCACCAGG GCGACATGCG
37801 GGACTTCCGG CTCGGCCGGA AGTTCTCCGC CGTGGTCAGC ATGTTCAGCT CCGTCGGCTA
37861 CCTGAAGACG ACCGAGGAAC TCGGCGCGGC CGTCGCCTCG TTCGCGGAGC ACCTGGAGCC
37921 CGGTGGCGTC GTCGTCGTCG AGCCGTGGTG GTTCCCGGAG ACCTTCGCCG ACGGCTGGGT
37981 CAGCGCCGAC GTCGTCCGCC GTGACGGGCG CACCGTGGCC CGTGTCTCGC ACTCGGTGCG
38041 GGAGGGGAAC GCGACGCGCA TGGAGGTCCA CTTCACCGTG GCCGACCCGG GCAAGGGCGT
38101 GCGGCACTTC TCCGACGTCC ATCTCATCAC CCTGTTCCAC CAGGCCGAGT ACGAGGCCGC
38161 GTTCACGGCC GCCGGGCTGC GCGTCGAGTA CCTGGAGGGC GGCCCGTCGG GCCGTGGCCT
38221 CTTCGTCGGC GTCCCCGCCT GAGCACCGCC CAAGACCCCC CGGGGCGGGA CGTCCCGGGT
38281 GCACCAAGCA AAGAGAGAGA AACGAACCGT GACAGGTAAG ACCCGAATAC CGCGTGTCCG
38341 CCGCGGCCGC ACCACGCCCA GGGCCTTCAC CCTGGCCGTC GTCGGCACCC TGCTGGCGGG
38401 CACCACCGTG GCGGCCGCCG CTCCCGGCGC CGCCGACACG GCCAATGTTC AGTACACGAG
38461 CCGGGCGGCG GAGCTCGTCG CCCAGATGAC GCTCGACGAG AAGATC
```

Those of skill in the art will recognize that, due to the degenerate nature of the genetic code, a variety of DNA compounds differing in their nucleotide sequences can be used to encode a given amino acid sequence of the invention. The native DNA sequence encoding the narbonolide PKS of *Streptomyces venezuelae* is shown herein merely to illustrate a preferred embodiment of the invention, and the invention includes DNA compounds of any sequence that encode the amino acid sequences of the polypeptides and proteins of the invention. In similar fashion, a polypeptide can typically tolerate one or more amino acid substitutions, deletions, and insertions in its amino acid sequence without loss or significant loss of a desired activity. The present invention includes such polypeptides with alternate amino acid sequences, and the amino acid sequences shown merely illustrate preferred embodiments of the invention.

The recombinant nucleic acids, proteins, and peptides of the invention are many and diverse. To facilitate an understanding of the invention and the diverse compounds and methods provided thereby, the following description of the various regions of the narbonolide PKS and corresponding coding sequences is provided.

The loading module of the narbonolide PKS contains an inactivated KS domain, an AT domain, and an ACP domain. The AT domain of the loading module binds propionyl CoA. Sequence analysis of the DNA encoding the KS domain indicates that this domain is enzymatically inactivated, as a critical cysteine residue in the motif TVDACSSSL, which is highly conserved among KS domains, is replaced by a glutamine and so is referred to as a $KS^Q$ domain. Such inactivated KS domains are also found in the PKS enzymes that synthesize the 16-membered macrolides carbomycin, spiromycin, tylosin, and niddamycin. While the KS domain is inactive for its usual function in extender modules, it is believed to serve as a decarboxylase in the loading module.

The present invention provides recombinant DNA compounds that encode the loading module of the narbonolide PKS and useful portions thereof. These recombinant DNA compounds are useful in the construction of PKS coding sequences that encode all or a portion of the narbonolide PKS and in the construction of hybrid PKS encoding DNA compounds of the invention, as described in the section concerning hybrid PKSs below. To facilitate description of the invention, reference to a PKS, protein, module, or domain herein can also refer to DNA compounds comprising coding sequences therefor and vice versa. Also, reference to a heterologous PKS refers to a PKS or DNA compounds comprising coding sequences therefor from an organism other than *Streptomyces venezuelae*. In addition, reference to a PKS or its coding sequence includes reference to any portion thereof.

The present invention provides recombinant DNA compounds that encode one or more of the domains of each of the six extender modules (modules 1–6, inclusive) of the narbonolide PKS. Modules 1 and 5 of the narbonolide PKS are functionally similar. Each of these extender modules contains a KS domain, an AT domain specific for methylmalonyl CoA, a KR domain, and an ACP domain. Module 2 of the narbonolide PKS contains a KS domain, an AT domain specific for malonyl CoA, a KR domain, a DH domain, and an ACP domain. Module 3 differs from extender modules 1 and 5 only in that it contains an inactive ketoreductase domain. Module 4 of the narbonolide PKS contains a KS domain, an AT domain specific for methylmalonyl CoA, a KR domain a DH domain, an ER domain, and an ACP domain. Module 6 of the narbonolide PKS contains a KS domain, an AT domain specific for methylmalonyl CoA, and an ACP domain.

In one important embodiment, the invention provides a recombinant narbonolide PKS that can be used to express only narbonolide (as opposed to the mixture of narbonolide and 10-deoxymethynolide that would otherwise be produced) in recombinant host cells. This recombinant narbonolide PKS results from a fusion of the coding sequences of the picAIII and picAIV genes so that extender modules 5 and 6 are present on a single protein. This recombinant PKS can be constructed on the *Streptomyces venezuelae* or *S. narbonensis* chromosome by homologous recombination. Alternatively, the recombinant PKS can be constructed on an expression vector and introduced into a heterologous host cell. This recombinant PKS is preferred for the expression of narbonolide and its glycosylated and/or hydroxylated derivatives, because a lesser amount or no 10-deoxymethynolide is produced from the recombinant PKS as compared to the native PKS. In a related embodiment, the invention provides a recombinant narbonolide PKS in which the picAIV gene has been rendered inactive by an insertion, deletion, or replacement. This recombinant PKS of the invention is useful in the production of 10-deoxymethynolide and its derivatives without production of narbonolide.

In similar fashion, the invention provides recombinant narbonolide PKS in which any of the domains of the native PKS have been deleted or rendered inactive to make the corresponding narbonolide or 10-deoxymethynolide derivative. Thus, the invention also provides recombinant narbonolide PKS genes that differ from the narbonolide PKS gene by one or more deletions. The deletions can encompass one or more modules and/or can be limited to a partial deletion within one or more modules. When a deletion encompasses an entire module, the resulting narbonolide derivative is at least two carbons shorter than the polyketide produced from the PKS encoded by the gene from which deleted PKS gene and corresponding polyketide were derived. When a deletion is within a module, the deletion typically encompasses a KR, DH, or ER domain, or both DH and ER domains, or both KR and DH domains, or all three KR, DH, and ER domains.

This aspect of the invention is illustrated in FIG. 4, parts B and C, which shows how a vector of the invention, plasmid pKOS039-16 (not shown), was used to delete or "knock out" the picA1 gene from the *Streptomyces venezuelae* chromosome. Plasmid pKOS039-16 comprises two segments (shown as cross-hatched boxes in FIG. 4, part B) of DNA flanking the picA1 gene and isolated from cosmid pKOS023-27 (shown as a linear segment in the Figure) of the invention. When plasmid pKOS039-16 was used to transform *S. venezuelae* and a double crossover homologous recombination event occurred, the picAI gene was deleted. The resulting host cell, designated K039-03 in the Figure, does not produce picromycin unless a functional picA1 gene is introduced.

This *Streptomyces venezuelae* K039-03 host cell and corresponding host cells of the invention are especially useful for the production of polyketides produced from hybrid PKS or narbonolide PKS derivatives. Especially preferred for production in this host cell are narbonolide derivatives produced by PKS enzymes that differ from the narbonolide PKS only in the loading module and/or extender modules 1 and/or 2. These are especially preferred, because one need only introduce into the host cell the modified picAI gene or other corresponding gene to produce the desired PKS and corresponding polyketide. These host cells are also preferred for desosaminylating polyketides in accordance with the method of the invention in which a polyketide is provided to an *S. venezuelae* cell and desosaminylated by the endogenous desosamine biosynthesis and desosaminyl transferase gene products.

The recombinant DNA compounds of the invention that encode each of the domains of each of the modules of the narbonolide PKS are also useful in the construction of expression vectors for the heterologous expression of the narbonolide PKS and for the construction of hybrid PKS expression vectors, as described further below.

Section II: The Genes for Desosamine Biosynthesis and Transfer and for Beta-glucosidase Narbonolide and 10-deoxymethynolide are desosaminylated in *Streptomyces venezuelae* and *S. narbonensis* to yield narbomycin and YC-17, respectively. This conversion requires the biosynthesis of desosamine and the transfer of the desosamine to the substrate polyketides by the enzyme desosaminyl transferase. Like other *Streptomyces*, *S. venezuelae* and *S. narbonensis* produce glucose and a glucosyl transferase enzyme that glucosylates desosamine at the 2' position. However, *S. venezuelae* and *S. narbonensis* also produce an enzyme called beta-glucosidase, which removes the glucose residue from the desosamine. The present invention provides recombinant DNA compounds and expression vectors for each of the desosamine biosynthesis enzymes, desosaminyl transferase, and beta-glucosidase.

As noted above, cosmid pKOS023-27 contains three ORFs that encode proteins involved in desosamine biosynthesis and transfer. The first ORF is from the picCII gene, also known as desVIII, a homologue of eryCII, believed to encode a 4-keto-6-deoxyglucose isomerase. The second ORF is from the picCIII gene, also known as desVII, a homologue of eryCIII, which encodes a desosaminyl transferase. The third ORF is from the picCVI gene, also known as desVI, a homologue of eryCVI, which encodes a 3-amino dimethyltransferase.

Figure 3:
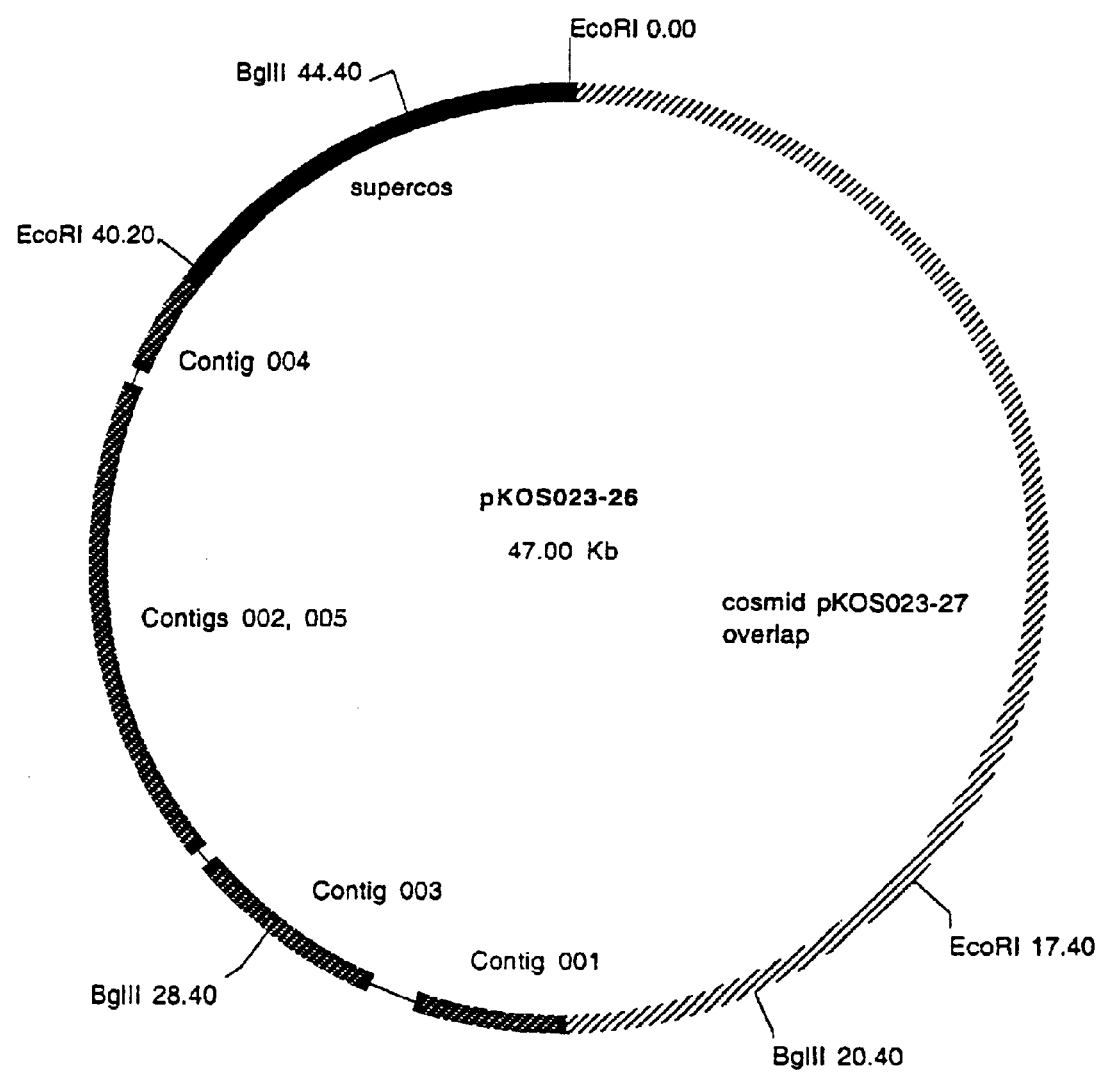
FIG. 3 shows a restriction site and function map of cosmid pKOS023-26.

The three genes above and the remaining desosamine biosynthetic genes can be isolated from cosmid pKOS023-26, which was deposited with the American Type Culture Collection on 8 Aug. 1998 under the Budapest Treaty and is available under the accession number ATCC 203141. FIG. 3 shows a restriction site and function map of cosmid pKOS023-26. This cosmid contains a region of overlap with cosmid pKOS023-27 representing nucleotides 14252 to nucleotides 38506 of pKOS023-27.

The remaining desosamine biosynthesis genes on cosmid pKOS023-26 include the following genes. ORF11, also known as desR, encodes beta-glucosidase and has no ery gene homologue. The picCI gene, also known as desV, is a homologue of eryCI. ORF14, also known as desIV, has no known ery gene homologue and encodes an NDP glucose 4,6-dehydratase. ORF13, also known as desIII, has no known ery gene homologue and encodes an NDP glucose synthase. The picCV gene, also known as desII, a homologue of eryCV is required for desosamine biosynthesis. The picCIV gene also known as desI, is a homologue of eryCIV, and its product is believed to be a 3,4-dehydratase. Other ORFs on cosmid pKOS023-26 include ORF12, believed to be a regulatory gene; ORF15, which encodes an S-adenosyl methionine synthase; and ORF16, which is a homolog of the *M. tuberculosis* cbhK gene. Cosmid pKOS023-26 also encodes the picK gene, which encodes the cytochrome P450 hydroxylase that hydroxylates the C12 of narbomycin and the C10 and C12 positions of YC-17. This gene is described in more detail in the following section.

Below, the amino acid sequences or partial amino acid sequences of the gene products of the desosamine biosynthesis and transfer and beta-glucosidase genes are shown. These amino acid sequences are followed by the DNA sequences that encode them.

Amino acid sequence of PICCI (SEQ ID NO:6).

Amino acid sequence of PICCI (SEQ ID NO: 6).

```
  1 VSSRAETPRV PFLDLKAAYE ELRAETDAAI ARVLDSGRYL LGPELEGFEA EFAAYCETDH
 61 AVGVNSGMDA LQLALRGLGI GPGDEVIVPS HTYIASWLAV SATGATPVPV EPHEDHPTLD
121 PLLVEKAITP RTRALLPVHL YGHPADMDAL RELADRHGLH IVEDAAQAHG ARYRGRRIGA
181 GSSVAAFSFY PGKNLGCFGD GGAVVTGDPE LAERLRMLRN YGSRQKYSHE TKGTNSRLDE
241 MQAAVLRIRL XHLDSWNGRR SALAAEYLSG LAGLPGIGLP VTAPDTDPVW HLFTVRTERR
301 DELRSHLDAR GIDTLTHYPV PVHLSPAYAG EAPPEGSLPR AESFARQVLS LPIGPHLERP
361 QALRVIDAVR EWAERVDQA
```

Amino acid sequence of 3-keto-6-deoxyglucose isomerase, PICCII (SEQ ID NO: 7).

```
  1 VADRELGTHL LETRGIHWIH AANGDPYATV LRGQADDPYP AYERVRARGA LSFSPTGSWV
 61 TADHALAASI LCSTDFGVSG ADGVPVPQQV LSYGEGCPLE REQVLPAAGD VPEGGQRAVV
121 EGIHRETLEG LAPDPSASYA FELLGGFVRP AVTAAAAAVL GVPADRRADF ADLLERLRPL
181 SDSLLAPQSL RTVRAADGAL AELTALLADS DDSPGALLSA LGVTAAVQLT GNAVLALLAH
241 PEQWRELCDR PGLAAAAVEE TLRYDPPVQL DARVVRGETE LAGRRLPAGA HVVVLTAATG
301 RDPEVFTDPE RFDLARPDAA AHLALHPAGP YGPVASLVRL QAEVALRTLA GRFPGLRQAG
361 DVLRPRRAPV GRGPLSVPVS SS
```

Amino acid sequence of desosaminyl transferase, PICCIII (SEQ ID NO: 8).

```
  1 MRVLLTSFAH HTHYYGLVPL AWALLAAGHE VRVASQPALT DTITGSGLAA VPVGTDHLIH
 61 EYRVRMAGEP RPNHPAIAFD EARPEPLDWD HALGIEAILA PYRYLLANND SMVDDLVDFA
121 RSWQPDLVLW EPTTYAGAVA AQVTGAAHAR VLWGPDVMGS ARRKFVALRD RQPPEHREDP
181 TAEWLTWTLD RYGASFEEEL LTGQFTIDPT PPSLRLDTGL PTVGMRYVPY NGTSVVPDWL
241 SEPPARPRVC LTLGVSAREV LGGDGVSQGD ILEALADLDI ELVATLDASQ RAEIRNYPKH
301 TRFTDFVPMH ALLPSCSAII HHGGAGTYAT AVINAVPQVM LAELWDAPVK ARAVAEQGAG
361 FFLPPAELTP QAVRDAVVRI LDDPSVATAA HRLREETFGD PTPAGIVPEL ERLAAQHRRP
421 PADARH
```

Partial amino acid sequence of aminotransferase-dehydrase, PICCIV (SEQ ID NO: 9).

```
  1 VKSALSDLAF FGGPAAFDQP LLVGRPNRID RARLYERLDR ALDSQWLSNG GPLVREFEER
 61 VAGLAGVRHA VATCNATAGL QLLAHAAGLT GEVIMPSMTF AATPHALRWI GLTPVFADID
121 PDTGNLDPDQ VAAAVTPRTS AVVGVHLWGR PCAADQLRKV ADEHGLRLYF DAAHALGCAV
181 DGRPAGSLGD AEVFSFHATK AVNAFEGGAV VTDDADLAAR IRALHNFGFD LPGGSPAGGT
241 NAKMSEAAAA MGLTSLDAFP EVIDRNRRNH AXYREHLADL PGVLVADHDR HGLNNHQYVI
301 VEIDEATTGI HRDLVMEVLK AEGVHTRAYF S
```

Amino acid sequence of PICCV (SEQ ID NO:10).

```
  1 MTAPALSATA PAERCAHPGA DLGAAVHAVG QTLAAGGLVP PDEAGTTARH LVRLAVRYGN
 61 SPFTPLEEAR HDLGVDRDAF RRLLALFGQV PELRTAVETG PAGAYWKNTL LPLEQRGVFD
121 AALARKPVFP YSVGLYPGPT CMFRCHFCVR VTGARYDPSA LDAGNAMFRS VIDEIPAGNP
181 SAMYFSGGLE PLTNPGLGSL AAHATDHGLR PTVYTNSFAL TERTLERQPG LWGLHAIRTS
241 LYGLNDEEYE QTTGKKAAFR RVRENLRRFQ QLRAERESPI NLGFAYIVLP GRASRLLDLV
301 DFIADLNDAG QGRTIDFVNI REDYSGRDDG KLPQEERAEL QEALNAFEER VRERTPGLHI
```

-continued

```
361 DYGYALNSLR TGADAELLRI KPATMRPTAH PQVAVQVDLL GDVYLYREAG FPDLDGATRY

421 IAGRVTPDTS LTEVVRDFVE RGGEVAAVDG DEYFMDGFDQ VVTARLNQLE RDAADGWEEA

481 RGFLR
```

Amino acid sequence of 3-amino dimethyl transferase, PICCVI (SEQ ID NO: 11).

```
  1 VYEVDHADVY DLFYLGRGKD YAAEASDIAD LVRSRTPEAS SLLDVACGTG THLEHFTKEF

61 GDTAGLELSE DMLTHARKRL PDATLHQGDM RDFRLGRKFS AVVSMFSSVG YLKTTEELGA

121 AVASFAEHLE PGGVVVVEPW WFPETFADGW VSADVVRRDG RTVARVSHSV REGNATRMEV

181 HFTVADPGKG VRHFSDVHLI TLFHQAEYEA AFTAAGLRVE YLEGGPSGRG LFVGVPA
```

Partial amino acid sequence of beta-glucosidase, ORF11 (SEQ ID NO: 12).

```
  1 MTLDEKISFV HWALDPDRQN VGYLPGVPRL GIPELRAADG PNGIRLVGQT ATALPAPVAL

61 ASTFDDTMAD SYGKVMGRDG RALNQDMVLG PMMNNIRVPH GGRNYETFSE DPLVVSRTAV

121 AQIKGIQGAG LMTTAKHFAA NNQENNRFSV NANVDEQTLR EIEFPAFEAS SKAGAGSFMC

181 AYNGLNGKPS CGNDELLNNV LRTQWGFQGW VMSDWLATPG TDAITKGLDQ EMGVELPGDV

241 PKGEPSPPAK FFGEALKTAV LNGTVPEAAV TRSAERIVGQ MEKFGLLLAT PAPRPERDKA

301 GAQAVSRKVA ENGAVLLRNE GQALPLAGDA GKSIAVIGPT AVDPKVTGLG SAHVVPDSAA

361 APLDTIKARA GAGATVTYET GEETFGTQIP AGNLSPAFNQ GHQLEPGKAG ALYDGTLTVP

421 ADGEYRIAVR ATGGYATVQL GSHTIEAGQV YGKVSSPLLK LTKGTHKLTI SGFAMSATPL

481 SLELGWVTPA AADATIAKAV ESARKARTAV VFAYDDGTEG VDRPNLSLPG TQDKLISAVA

541 DANPNTIVVL NTGSSVLMPW LSKTRAVLDM WYPGQAGAEA TAALLYGDVN PSGKLTQSFP

601 AAENQHAVAG DPTSYPGVDN QQTYREGIHV GYRWFDKENV KPLFPFGHGL SYSTFTQSAP

661 TVVRTSTGGL KVTVTVRNSG KRAGQEVVQA YLGASPNVTA PQAKKKLVGY TKVSLAAGEA

721 KTVTVNVDRR QLQFWDAATD NWKTGTGNRL LQTGSSSADL RGSATVNVW
```

Amino acid sequence of transcriptional activator, ORF12 (SEQ ID NO: 13).

```
  1 MNLVERDGEI AHLRAVLDAS AAGDGTLLLV SGPAGSGKTE LLRSLRRLAA ERETPVWSVR

61 ALPGDRDIPL GVLCQLLRSA EQHGADTSAV RDLLDAASRR AGTSPPPPTR RSASTRHTAC

121 TTGCSPSPAG TPFLVAVDDL THADTASLRF LLYCAAHHDQ GGIGFVMTER ASQRAGYRVF

181 RAELLRQPHC RNMWLSGLPP SGVRQLLAHY YGPEAAERRA PAYHATTGGN PLLLRALTQD

241 RQASHTTLGA AGGDEPVHGD AFAQAVLDCL HRSAEGTLET ARWLAVLEQS DPLLVERLTG

301 TTAAAVERHI QELAAIGLLD EDGTLGQPAI REAALQDLPA GERTELHRRA AEQLHRDGAD

361 EDTVARHLLV GGAPDAPWAL PLLERGAQQA LFDDRLDDAF RILEFAVRSS TDNTQLARLA

421 PHLVAASWRM NPHMTTRALA LFDRLLSGEL PPSHPVMALI RCLVWYGRLP EAADALSRLR

481 PSSDNDALEL SLTRMWLAAL CPPLLESLPA TPEPERGPVP VRLAPRTTAL QAQAGVFORG

541 PDNASVAQAE QILQGCRLSE ETYEALETAL LVLVHADRLD RALFWSDALL AEAVERRSLG

601 WEAVFAATRA MIAIRCGDLP TARERAELAL SHAAPESWGL AVGMPLSALL LACTEAGEYE

661 QAERVLRQPV PDAMFDSRHG MEYMHARGRY WLAXGRLHAA LGEEMLCGEI LGSWNLDQPS

721 IVPWRTSAAE VYLRIGNRQK ARALAEAQLA LVRPGRSRTR GLTLRVLAAA VDGQQAERLH

781 AEAVDMLHDS GDRLEHARAL AGMSRHQQAQ GDNYRARMTA RLAGDMAWAC GAYPLAEEIV

841 PGRGGRRAKA VSTELELPGG PDVGLLSEAE RRVAALAARG LTNRQIARRL CVTASTVEQH

901 LTRVYRKLNV TRRADLPISL AQDKSVTA
```

Amino acid sequence of dNDP-glucose synthase
(glucose-1-phosphate thymidyl transferase), ORF13 (SEQ ID NO: 14).

-continued

```
  1 MKGIVLAGGS GTRLHPATSV ISKQILPVYN KPMIYYPLSV LMLGGIREIQ IISTPQHIEL

61 FQSLLGNGRH LGIELDYAVQ KEPAGIADAL LVGAEHIGDD TCALILGDNI FHGPGLYTLL

121 RDSIARLDGC VLFGYPVKDP ERYGVAEVDA TGRLTDLVEK PVKPRSNLAV TGLYLYDNDV

181 VDIAKNIRPS PRGELEITDV NRVYLERGRA ELVNLGRGFA WLDTGTHDSL LRAAQYVQVL

241 EERQGVWIAG LEEIAFRMGF IDAEACHGLG EGLSRTEYGS YLMEIAGREG AP
```

Amino acid sequence of dNDP-glucose 4,6-dehydratase, ORF14 (SEQ ID NO: 15).

```
  1 VRLLVTGGAG FIGSHFVRQL LAGAYPDVPA DEVIVLDSLT YAGNRANLAP VDADPRLRFV

61 HGDIRDAGLL ARELRGVDAI VHFAAESHVD RSIAGASVFT ETNVQGTQTL LQCAVDAGVG

121 RVVHVSTDEV YGSIDSGSWT ESSPLEPNSP YAASKAGSDL VARAYHRTYG LDVRITRCCN

181 NYGPYQHPEK LIPLFVTNLL DGGTLPLYGD GANVREWVHT DDHCRGIALV LAGGRAGEIY

241 HIGGGLELTN RELTGILLDS LGADWSSVRK VADRKGHDLR YSLDGGKIER ELGYRPQVSF

301 ADGLARTVRW YRENRGWWEP LKATAPQLPA TAVEVSA
```

Partial amino acid sequence of S-adenosylmethionine synthase, ORF15 (SEQ ID NO: 16).

```
  1 IGYDSSKKGF DGASCGVSVS IGSQSPDIAQ GVDTAYEKRV EGASQRDEGD ELDKQGAGDQ

61 GLMFGYASDE TPELMPLPIH LAHRLSRRLT EVRKNGTIPY LRPDGKTQVT IEYDGDRAVR

121 LDTVVVSSQH ASDIDLESLL APDVRKFVVE HVLAQLVEDG IKLDTDGYRL LVNPTGRFEI

181 GGPMGDAGLT GRKIIIDTYG GMARHGGGAF SGKDPSKVDR SAAYAMRWVA KNVVAAGLAS

241 RCEVQVAYAI GKAEPVGLFV ETFGTHKIET EKIENAIGEV FDLRPAAIIR DLDLLRPIYS

301 QTAAYGHFGR ELPDFTWERT DRVDALKKAA GL
```

Partial amino acid sequence of ORF16
(homologous to *M. tuberculosis* cbhK) (SEQ ID NO: 17).

```
  1 MRIAVTGSIA TDHLMTFPGR FAEQILPDQL AHVSLSFLVD TLDIRHGGVA ANIAYGLGLL

61 GRRPVLVGAV GKDFDGYGQL LRAAGVDTDS VRVSDRQHTA RFMCTTDEDG NQLASFYAGA

121 MAEARDIDLG ETAGRPGGID LVLVGADDPE AMVRHTRVCR ELGLRRAADP SQQLARLEGD

181 SVRELVDGAE LLFTNAYERA LLLSKTGWTE QEVLARVGTW ITTLGAKGCR
```

Amino acid sequence of 3-keto-6-deoxyglucose isomerase, PICCII (SEQ ID NO:7).

Amino acid sequence of desosaminyl transferase, PICCIII (SEQ ID NO:8).

Partial amino acid sequence of aminotransferase-dehydrase, PICCIV (SEQ ID NO:9).

Amino acid sequence of PICCV (SEQ ID NO:10).

Amino acid sequence of 3-amino dimethyl transferase, PICCVI (SEQ ID NO:11).

Partial amino acid sequence of beta-glucosidase ORF11 (SEQ ID NO:12).

Amino acid sequence of trascriptional activator, ORF12 (SEQ ID NO:13).

Amino acid sequence of dNDP-glucose synthase (glucose-1-phosphate thymidyl transferase), ORF13 (SEQ ID NO:14).

Amino acid sequence of dNDP-glucose 4,6-dehydratase, ORF14 (SEQ ID NO:15).

Partial amino acid sequence of S-adenosylmethionine synthase, ORF15 (SEQ ID NO:16).

Partial amino acid sequence of ORF16 (homologous to *M. tuberculosis* cbhK) (SEQ ID NO:17).

While not all of the insert DNA of cosmid pKOS023-26 has been sequenced, five large contigs shown of FIG. 3 have been assembled and provide sufficient sequence information to manipulate the genes therein in accordance with the methods of the invention. The sequences of each of these five contigs are shown below.

Contig 001 from cosmid pKOS023-26 contains 2401 nucleotides, the first 100 bases of which correspond to 100 bases of the insert sequence of cosmid pKOS023-27. Nucleotides 80–2389 constitute ORF11, which encodes 1 beta glucosidase (SEQ ID NO:20).

```
  1 CGTGGCGGCC GCCGCTCCCG GCGCCGCCGA CACGGCCAAT GTTCAGTACA CGAGCCGGGC

61 GGCGGAGCTC GTCGCCCAGA TGACGCTCGA CGAGAAGATC AGCTTCGTCC ACTGGGCGCT

121 GGACCCCGAC CGGCAGAACG TCGGCTACCT TCCCGGCGTG CCGCGTCTGG GCATCCCGGA
```

-continued

```
 181 GCTGCGTGCC GCCGACGGCC CGAACGGCAT CCGCCTGGTG GGGCAGACCG CCACCGCGCT
 241 GCCCGCGCCG GTCGCCCTGG CCAGCACCTT CGACGACACC ATGGCCGACA GCTACGGCAA
 301 GGTCATGGGC CGCGACGGTC GCGCGCTCAA CCAGGACATG GTCCTGGGCC CGATGATGAA
 361 CAACATCCGG GTGCCGCACG GCGGCCGGAA CTACGAGACC TTCAGCGAGG ACCCCCTGGT
 421 CTCCTCGCGC ACCGCGGTCG CCCAGATCAA GGGCATCCAG GGTGCGGGTC TGATGACCAC
 481 GGCCAAGCAC TTCGCGGCCA CAACCAGGA GAACAACCGC TTCTCCGTGA ACGCCAATGT
 541 CGACGAGCAG ACGCTCCGCG AGATCGAGTT CCCGGCGTTC GAGGCGTCCT CCAAGGCCGG
 601 CGCGGGCTCC TTCATGTGTG CCTACAACGG CCTCAACGGG AAGCCGTCCT GCGGCAACGA
 661 CGAGCTCCTC AACAACGTGC TGCGCACGCA GTGGGGCTTC CAGGGCTGGG TGATGTCCGA
 721 CTGGCTCGCC ACCCCGGGCA CCGACGCCAT CACCAAGGGC CTCGACCAGG AGATGGGCGT
 781 CGAGCTCCCC GGCGACGTCC CGAAGGGCGA GCCCTCGCCG CCGGCCAAGT TCTTCGGCGA
 841 GGCGCTGAAG ACGGCCGTCC TGAACGGCAC GGTCCCCGAG GCGGCCGTGA CGCGGTCGGC
 901 GGAGCGGATC GTCGGCCAGA TGGAGAAGTT CGGTCTGCTC CTCGCCACTC CGGCGCCGCG
 961 GCCCGAGCGC GACAAGGCGG GTGCCCAGGC GGTGTCCCGC AAGGTCGCCG AGAACGGCGC
1021 GGTGCTCCTG CGCAACGAGG GCCAGGCCCT GCCGCTCGCC GGTGACGCCG GCAAGAGCAT
1081 CGCGGTCATC GGCCCGACGG CCGTCGACCC CAAGGTCACC GGCCTGGGCA GCGCCCACGT
1141 CGTCCCGGAC TCGGCGGCGG CGCCACTCGA CACCATCAAG GCCCGCGCGG GTGCGGGTGC
1201 GACGGTGACG TACGAGACGG GTGAGGAGAC CTTCGGGACG CAGATCCCGG CGGGGAACCT
1261 CAGCCCGGCG TTCAACCAGG GCCACCAGCT CGAGCCGGGC AAGGCGGGGG CGCTGTACGA
1321 CGGCACGCTG ACCGTGCCCG CCGACGGCGA GTACCGCATC GCGGTCCGTG CCACCGGTGG
1381 TTACGCCACG GTGCAGCTCG GCAGCCACAC CATCGAGGCC GGTCAGGTCT ACGGCAAGGT
1441 GAGCAGCCCG CTCCTCAAGC TGACCAAGGG CACGCACAAG CTCACGATCT CGGGCTTCGC
1501 GATGAGTGCC ACCCCGCTCT CCCTGGAGCT GGGCTGGGTN ACGCCGGCGG CGGCCGACGC
1561 GACGATCGCG AAGGCCGTGG AGTCGGCGCG GAAGGCCCGT ACGGCGGTCG TCTTCGCCTA
1621 CGACGACGGC ACCGAGGGCG TCGACCGTCC GAACCTGTCG CTGCCGGGTA CGCAGGACAA
1681 GCTGATCTCG GCTGTCGCGG ACGCCAACCC GAACACGATC GTGGTCCTCA ACACCGGTTC
1741 GTCGGTGCTG ATGCCGTGGC TGTCCAAGAC CCGCGCGGTC CTGGACATGT GGTACCCGGG
1801 CCAGGCGGGC GCCGAGGCCA CCGCCGCGCT GCTCTACGGT GACGTCAACC CGAGCGGCAA
1861 GCTCACGCAG AGCTTCCCGG CCGCCGAGAA CCAGCACGCG GTCGCCGGCG ACCCGACCAG
1921 CTACCCGGGC GTCGACAACC AGCAGACGTA CCGCGAGGGC ATCCACGTCG GTACCGCTG
1981 GTTCGACAAG GAGAACGTCA AGCCGCTGTT CCCGTTCGGG CACGGCCTGT CGTACACCTC
2041 GTTCACGCAG AGCGCCCCGA CCGTCGTGCG TACGTCCACG GGTGGTCTGA AGGTCACGGT
2101 CACGGTCCGC AACAGCGGGA AGCGCGCCGG CCAGGAGGTC GTCCAGGCGT ACCTCGGTGC
2161 CAGCCCGAAC GTGACGGCTC CGCAGGCGAA GAAGAAGCTC GTGGGCTACA CGAAGGTCTC
2221 GCTCGCCGCG GGCGAGGCGA AGACGGTGAC GGTGAACGTC GACCGCCGTC AGCTGCAGTT
2281 CTGGGATGCC GCCACGGACA ACTGGAAGAC GGGAACGGGC AACCGCCTCC TGCAGACCGG
2341 TTCGTCCTCC GCCGACCTGC GGGGCAGCGC CACGGTCAAC GTCTGGTGAC GTGACGCCGT
2401 G
```

Contig 002 from cosmid pKOS023-26 contains 5970 nucleotides and the following ORFs: from nucleotide 995 to 1 is an ORF of picCIV that encodes a partial sequence of an amino transferase-dehydrase; from nucleotides 1356 to 2606 is an ORF of picK that encodes a cytochrome P450 hydroxylase; and from nucleotides 2739 to 5525 is ORF12, which encodes a transcriptional activator (SEQ ID NO:21).

```
   1 GGCGAGAAGT AGGCGCGGGT GTGCACGCCT TCGGCCTTCA GGACCTCCAT GACGAGGTCG
  61 CGGTGGATGC CGGTGGTGGC CTCGTCGATC TCGACGATCA CGTACTGGTG GTTGTTGAGG
 121 CCGTGGCGGT CGTGGTCGGC GACGAGGACG CCGGGGAGGT CCGCGAGGTG CTCGCGGTAG
 181 SCGGCGTGGT TGCGCCGGTT CCGGTCGATG ACCTCGGGAA ACGCGTCGAG GGAGGTGAGG
 241 CCCATGGCGG CGGCGGCCTC GCTCATCTTG GCGTTGGTCC CGCCGGCGGG GCTGCCGCCG
 301 GGCAGGTCGA AGCCGAAGTT GTGGAGGGCG CGGATCCGGG CGGCGAGGTC GGCGTCGTCG
 361 GTGACGACGG CGCCGCCCTC GAAGGCGTTG ACGGCCTTGG TGGCGTGGAA GCTGAAGACC
 421 TCGGCGTCGC CGAGGCTGCC GGCGGGCCGG CCGTCGACCG CGCAGCCGAG GGCGTGCGCG
 481 GCGTCGAAGT ACAGCCGCAG GCCGTGCTCG TCGGCGACCT TCCGCAGCTG GTCGGCGGCG
 541 CAGGGGCGGC CCCAGAGGTG GACGCCGACG ACGGCCGAGG TGCGGGGTGT GACCGCGGCG
 601 GCCACCTGGT CCGGGTCGAG GTTGCCGGTG TCCGGGTCGA TGTCGGCGAA GACCGGGGTG
 661 AGGCCGATCC AGCGCAGTGC GTGCGGGGTG GCGGCGAACG TCATCGACGG CATGATCACT
 721 TCGCCGGTGA GGCCGGCGGC GTGCGCGAGG AGCTGGAGCC CGGCCGTGGC GTTGCAGGTG
 781 GCCACGGCAT GCCGGACCCC GGCGAGCCCG GCGACGCGCT CCTCGAACTC GCGGACGAGC
 841 GGGCCGCCGT TGGACAGCCA CTGGCTGTCG AGGGCCCGGT CGAGCCGCTC GTACAGCCTG
 901 GCGCGGTCGA TGCGGTTGGG CCGCCCCACG AGGAGCGGCT GGTCGAAAGC GGCGGGGCCG
 961 CCGAAGAATG CGAGGTCGGA TAAGGCGCTT TTCACGGATG TTCCCTCCGG GCCACCGTCA
1021 CGAAATGATT CGCCGATCCG GGAATCCCGA ACGAGGTCGC CGCGCTCCAC CGTGACGTAC
1081 GACGAGATGG TCGATTGTGG TGGTCGATTT CGGGGGACT CTAATCCGCG CGGAACGGGA
1141 CCGACAAGAG CACGCTATGC GCTCTCGATG TGCTTCGGAT CACATCCGCC TCCGGGGTAT
1201 TCCATCGGCG GCCCGAATGT GATGATCCTT GACAGGATCC GGGAATCAGC CGAGCCGCCG
1261 GGAGGGCCGG GGCGCGCTCC GCGGAAGAGT ACGTGTGAGA AGTCCCGTTC CTCTTCCCGT
1321 TTCCGTTCCG CTTCCGGCCC GGTCTGGAGT TCTCCGTGCG CCGTACCCAG CAGGGAACGA
1381 CCGCTTCTCC CCCGGTACTC GACCTCGGGG CCCTGGGGCA GGATTTCGCG GCCGATCCGT
1441 ATCCGACGTA CGCGAGACTG CGTGCCGAGG GTCCGGCCCA CCGGGTGCGC ACCCCCGAGG
1501 GGGACGAGGT GTGGCTGGTC GTCGGCTACG ACCGGGCGCG GGCGGTCCTC GCCGATCCCC
1561 GGTTCAGCAA GGACTGGCGC AACTCCACGA CTCCCCTGAC CGAGGCCGAG GCCGCGCTCA
1621 ACCACAACAT GCTGGAGTCC GACCCGCCGC GGCACACCCG GCTGCGCAAG CTGGTGGCCC
1681 GTGAGTTCAC CATGCGCCGG GTCGAGTTGC TGCGGCCCCG GGTCCAGGAG ATCGTCGACG
1741 GGCTCGTGGA CGCCATGCTG GCGGCGCCCG ACGGCCGCGC CGATCTGATG GAGTCCCTGG
1801 CCTGGCCGCT GCCGATCACC GTGATCTCCG AACTCCTCGG CGTGCCCGAG CCGGACCGCG
1861 CCGCCTTCCG CGTCTGGACC GACGCCTTCG TCTTCCCGGA CGATCCCGCC CAGGCCCAGA
1921 CCGCCATGGC CGAGATGAGC GGCTATCTCT CCCGGCTCAT CGACTCCAAG CGCGGGCAGG
1981 ACGGCGAGGA CCTGCTCAGC GCGCTCGTGC GGACCAGCGA CGAGGACGGC TCCCGGCTGA
2041 CCTCCGAGGA GCTGCTCGGT ATGGCCCACA TCCTGCTCGT CGCGGGGCAC GAGACCACGG
2101 TCAATCTGAT CGCCAACGGC ATGTACGCGC TGCTCTCGCA CCCCGACCAG CTGGCCGCCC
2161 TGCGGGCCGA CATGACGCTC TTGGACGGCG CGGTGGAGGA GATGTTGCGC TACGAGGGCC
```

```
                        -continued
2221 CGGTGGAATC CGCGACCTAC CGCTTCCCGG TCGAGCCCGT CGACCTGGAC GGCACGGTCA

2281 TCCCGGCCGG TGACACGGTC CTCGTCGTCC TGGCCGACGC CCACCGCACC CCCGAGCGCT

2341 TCCCGGACCC GCACCGCTTC GACATCCGCC GGGACACCGC CGGCCATCTC GCCTTCGGCC

2401 ACGGCATCCA CTTCTGCATC GGCGCCCCCT TGGCCCGGTT GGAGGCCCGG ATCGCCGTCC

2461 GCGCCCTTCT CGAACGCTGC CCGGACCTCG CCCTGGACGT CTCCCCCGGC GAACTCGTGT

2521 GGTATCCGAA CCCGATGATC CGCGGGCTCA AGGCCCTGCC GATCCGCTGG CGGCGAGGAC

2581 GGGAGGCGGG CCGCCGTACC GGTTGAACCC GCACGTCACC CATTACGACT CCTTGTCACG

2641 GAAGCCCCGG ATCGGTCCCC CCTCGCCGTA ACAAGACCTG GTTAGAGTGA TGGAGGACGA

2701 CGAAGGGTTC GGCGCCCGGA CGAGGGGGGA CTTCCGCGAT GAATCTGGTG GAACGCGACG

2761 GGGAGATAGC CCATCTCAGG GCCGTTCTTG ACGCATCCGC CGCAGGTGAC GGGACGCTCT

2821 TACTCGTCTC CGGACCGGCC GGCAGCGGGA AGACGGAGCT GCTGCGGTCG CTCCGCCGGC

2881 TGGCCGCCGA GCGGGAGACC CCCGTCTGGT CGGTCCGGGC GCTGCCGGGT GACCGCGACA

2941 TCCCCCTGGG CGTCCTCTGC CAGTTACTCC GCAGCGCCGA CAACACGGT GCCGACACCT

3001 CCGCCGTCCG CGACCTGCTG GACGCCGCCT CGCGGCGGGC CGGAACCTCA CCTCCCCCGC

3061 CGACGCGCCG CTCCGCGTCG ACGAGACACA CCGCCTGCAC GACTGGCTGC TCTCCGTCTC

3121 CCGCCGGCAC CCCGTTCCTC GTCGCCGTCG ACGACCTGAC CCACGCCGAC ACCGCGTCCC

3181 TGAGGTTCCT CCTGTACTGC GCCGCCCACC ACGACCAGGG CGGCATCGGC TTCGTCATGA

3241 CCGAGCGGGC CTCGCAGCGC GCCGGATACC GGGTGTTCCG CGCCGAGCTG CTCCGCCAGC

3301 CGCACTGCCG CAACATGTGG CTCTCCGGGC TTCCCCCCAG CGGGGTACGC CAGTTACTCG

3361 CCCACTACTA CGGCCCCGAG GCCGCCGAGC GGCGGGCCCC CGCGTACCAC GCGACGACCG

3421 GCGGGAACCC GCTGCTCCTG CGGGCGCTGA CCCAGGACCG GCAGGCCTCC CACACCACCC

3481 TCGGCGCGGC CGGCGGCGAC GAGCCCGTCC ACGGCGACGC CTTCGCCCAG GCCGTCCTCG

3541 ACTGCCTGCA CCGCAGCGCC GAGGGCACAC TGGAGACCGC CCGCTGGCTC GCGGTCCTCG

3601 AACAGTCCGA CCCGCTCCTG GTGGAGCGGC TCACGGGAAC GACCGCCGCC GCCGTCGAGC

3661 GCCACATCCA GGAGCTCGCC GCCATCGGCC TCCTGGACGA GGACGGCACC CTGGGACAGC

3721 CCGCGATCCG CGAGGCCGCC CTCCAGGACC TGCCGGCCGG CGAGCGCACC GAACTGCACC

3781 GGCGCGCCGC GGAGCAGCTG CACCGGGACG GCGCCGACGA GGACACCGTG GCCCGCCACC

3841 TGCTGGTCGG CGGCGCCCCC GACGCTCCCT GGGCGCTGCC CCTGCTCGAA CGGGGCGCGC

3901 AGCAGGCCCT GTTCGACGAC CGACTCGACG ACGCCTTCCG GATCCTCGAG TTCGCCGTGC

3961 GGTCGAGCAC CGACAACACC CAGCTGGCCC GCCTCGCCCC ACACCTGGTC GCGGCCTCCT

4021 GGCGGATGAA CCCGCACATG ACGACCCGGG CCCTCGCACT CTTCGACCGG CTCCTGAGCG

4081 GTGAACTGCC GCCCAGCCAC CCGGTCATGG CCCTGATCCG CTGCCTCGTC TGGTACGGNC

4141 GGCTGCCCGA GGCCGCCGAC GCGCTGTCCC GGCTGCGGCC CAGCTCCGAC AACGATGCCT

4201 TGGAGCTGTC GCTCACCCGG ATGTGGCTCG CGGCGCTGTG CCCGCCGCTC CTGGAGTCCC

4261 TGCCGGCCAC GCCGGAGCCG GAGCGGGGTC CCGTCCCCGT ACGGCTCGCG CCGCGGACGA

4321 CCGCGCTCCA GGCCCAGGCC GGCGTCTTCC AGCGGGCCC GGACAACGCC TCGGTCGCGC

4381 AGGCCGAACA GATCCTGCAG GGCTGCCGGC TGTCGGAGGA GACGTACGAG GCCCTGGAGA

4441 CGGCCCTCTT GGTCCTCGTC CACGCCGACC GGCTCGACCG GGCGCTGTTC TGGTCGGACG

4501 CCCTGCTCGC CGAGGCCGTG GAGCGGCGGT CGCTCGGCTG GGAGGCGGTC TTCGCCGCGA

4561 CCCGGGCGAT GATCGCGATC CGCTGCGGCG ACCTCCCGAC GGCGCGGGAG CGGGCCGAGC
```

```
                              -continued
4621 TGGCGCTCTC CCACGCGGCG CCGGAGAGCT GGGGCCTCGC CGTGGGCATG CCCCTCTCCG

4681 CGCTGCTGCT CGCCTGCACG GAGGCCGGCG AGTACGAACA GGCGGAGCGG GTCCTGCGGC

4741 AGCCGGTGCC GGACGCGATG TTCGACTCGC GGCACGGCAT GGAGTACATG CACGCCCGGG

4801 GCCGCTACTG GCTGGCGANC GGCCGGCTGC ACGCGGCGCT GGGCGAGTTC ATGCTCTGCG

4861 GGGAGATCCT GGGCAGCTGG AACCTCGACC AGCCCTCGAT CGTGCCCTGG CGGACCTCCG

4921 CCGCCGAGGT GTACCTGCGG CTCGGCAACC GCCAGAAGGC CAGGGCGCTG GCCGAGGCCC

4981 AGCTCGCCCT GGTGCGGCCC GGGCGCTCCC GCACCCGGGG TCTCACCCTG CGGGTCCTGG

5041 CGGCGGCGGT GGACGGCCAG CAGGCGGAGC GGCTGCACGC CGAGGCGGTC GACATGCTGC

5101 ACGACAGCGG CGACCGGCTC GAACACGCCC GCGCGCTCGC CGGGATGAGC CGCCACCAGC

5161 AGGCCCAGGG GGACAACTAC CGGGCGAGGA TGACGGCGCG GCTCGCCGGC GACATGGCGT

5221 GGGCCTGCGG CGCGTACCCG CTGGCCGAGG AGATCGTGCC GGGCCGCGGC GGCCGCCGGG

5281 CGAAGGCGGT GAGCACGGAG CTGGAACTGC CGGGCGGCCC GGACGTCGGC CTGCTCTCGG

5341 AGGCCGAACG CCGGGTGGCG GCCCTGGCAG CCCGAGGATT GACGAACCGC CAGATAGCGC

5401 GCCGGCTCTG CGTCACCGCG AGCACGGTCG AACAGCACCT GACGCGCGTC TACCGCAAAC

5461 TGAACGTGAC CCGCCGAGCA GACCTCCCGA TCAGCCTCGC CCAGGACAAG TCCGTCACGG

5521 CCTGAGCCAC CCCCGGTGTC CCCGTGCGAC GACCCGCCGC ACGGGCCACC GGGCCCGCCG

5581 GGACACGCCG GTGCGACACG GGGGCGCGCC AGGTGCCATG GGGACCTCCG TGACCGCCCG

5641 AGGCGCCCGA GGCGCCCGGT GCGGCACCCG GAGACGCCAG GACCGCCGGG ACCACCGGAG

5701 ACGCCAGGGA CCGCTGGGGA CACCGGGACC TCAGGGACCG CCGGGACCGC CCGAGTTGCA

5761 CCCGGTGCGC CCGGGGACAC CAGACCGCCG GGACCACCCG AGGGTGCCCG GTGTGGCCCC

5821 GGCGGCCGGG GTGTCCTTCA TCGGTGGGCC TTCATCGGCA GGAGGAAGCG ACCGTGAGAC

5881 CCGTCGTGCC GTCGGCGATC AGCCGCCTGT ACGGGCGTCG GACTCCCTGG CGGTCCCGGA

5941 CCCGTCGTAC GGGCTCGCGG GACCCGGTGC
```

Contig 003 from cosmid pKOS023-26 contains 3292 nucleotides and the following ORFs: from nucleotide 104 to 982 is ORF13, which encodes dNDP glucose synthase (glucose-1-phosphate thymidyl transferase); from nucleotide 1114 to 2127 is ORF14, which encodes dNDP-glucose 4,6-dehydratase; and from nucleotide 2124 to 3263 is the picCI ORF (SEQ ID NO:22).

```
  1 ACCCCCCAAA GGGGTGGTGA CACTCCCCCT GCGCAGCCCC TAGCGCCCCC CTAACTCGCC

61 ACGCCGACCG TTATCACCGG CGCCCTGCTG CTAGTTTCCG AGAATGAAGG GAATAGTCCT

121 GGCCGGCGGG AGCGGAACTC GGCTGCATCC GGCGACCTCG GTCATTTCGA AGCAGATTCT

181 TCCGGTCTAC AACAAACCGA TGATCTACTA TCCGCTGTCG GTTCTCATGC TCGGCGGTAT

241 TCGCGAGATT CAAATCATCT CGACCCCCCA GCACATCGAA CTCTTCCAGT CGCTTCTCGG

301 AAACGGCAGG CACCTGGGAA TAGAACTCGA CTATGCGGTC CAGAAAGAGC CCGCAGGAAT

361 CGCGGACGCA CTTCTCGTCG GAGCCGAGCA CATCGGCGAC GACACCTGCG CCCTGATCCT

421 GGGCGACAAC ATCTTCCACG GGCCCGGCCT CTACACGCTC CTGCGGGACA GCATCGCGCG

481 CCTCGACGGC TGCGTGCTCT TCGGCTACCC GGTCAAGGAC CCCGAGCGGT ACGGCGTCGC

541 CGAGGTGGAC GCGACGGGCC GGCTGACCGA CCTCGTCGAG AAGCCCGTCA GCCGCGCTC

601 CAACCTCGCC GTCACCGGCC TCTACCTCTA CGACAACGAC GTCGTCGACA TCGCCAAGAA

661 CATCCGGCCC TCGCCGCGCG GCGAGCTGGA GATCACCGAC GTCAACCGCG TCTACCTGGA

721 GCGGGGCCGG GCCGAACTCG TCAACCTGGG CCGCGGCTTC GCCTGGCTGG ACACCGGCAC
```

-continued

```
 781 CCACGACTCG CTCCTGCGGG CCGCCCAGTA CGTCCAGGTC CTGGAGGAGC GGCAGGGCGT
 841 CTGGATCGCG GGCCTTGAGG AGATCGCCTT CCGCATGGGC TTCATCGACG CCGAGGCCTG
 901 TCACGGCCTG GGAGAAGGCC TCTCCCGCAC CGAGTACGGC AGCTATCTGA TGGAGATCGC
 961 CGGCCGCGAG GGAGCCCCGT GAGGGCACCT CGCGGCCGAC GCGTTCCCAC GACCGACAGC
1021 GCCACCGACA GTGCGACCCA CACCGCGACC CGCACCGCCA CCGACAGTGC GACCCACACC
1081 GCGACCTACA GCGCGACCGA AAGGAAGACG GCAGTGCGGC TTCTGGTGAC CGGAGGTGCG
1141 GGCTTCATCG GCTCGCACTT CGTGCGGCAG CTCCTCGCCG GGGCGTACCC CGACGTGCCC
1201 GCCGATGAGG TGATCGTCCT GGACAGCCTC ACCTACGCGG GCAACCGCGC CAACCTCGCC
1261 CCGGTGGACG CGGACCCGCG ACTGCGCTTC GTCCACGGCG ACATCCGCGA CGCCGGCCTC
1321 CTCGCCCGGG AACTGCGCGG CGTGGACGCC ATCGTCCACT TCGCGGCCGA GAGCCACGTG
1381 GACCGCTCCA TCGCGGGCGC GTCCGTGTTC ACCGAGACCA ACGTGCAGGG CACGCAGACG
1441 CTGCTCCAGT GCGCCGTCGA CGCCGGCGTC GGCCGGGTCG TGCACGTCTC CACCGACGAG
1501 GTGTACGGGT CGATCGACTC CGGCTCCTGG ACCGAGAGCA GCCCGCTGGA GCCCAACTCG
1561 CCCTACGCGG CGTCCAAGGC CGGCTCCGAC CTCGTTGCCC GCGCCTACCA CCGGACGTAC
1621 GGCCTCGACG TACGGATCAC CCGCTGCTGC AACAACTACG GCCGTACCA GCACCCCGAG
1681 AAGCTCATCC CCCTCTTCGT GACGAACCTC CTCGACGGCG GGACGCTCCC GCTGTACGGC
1741 GACGGCGCGA ACGTCCGCGA GTGGGTGCAC ACCGACGACC ACTGCCGGGG CATCGCGCTC
1801 GTCCTCGCGG GCGGCCGGGC CGGCGAGATC TACCACATCG GCGGCGGCCT GGAGCTGACC
1861 AACCGCGAAC TCACCGGCAT CCTCCTGGAC TCGCTCGGCG CCGACTGGTC CTCGGTCCGG
1921 AAGGTCGCCG ACCGCAAGGG CCACGACCTG CGCTACTCCC TCGACGGCGG CAAGATCGAG
1981 CGCGAGCTCG GCTACCGCCC GCAGGTCTCC TTCGCGGACG GCCTCGCGCG GACCGTCCGC
2041 TGGTACCGGG AGAACCGCGG CTGGTGGGAG CCGCTCAAGG CGACCGCCCC GCAGCTGCCC
2101 GCCACCGCCG TGGAGGTGTC CGCGTGAGCA GCCGCGCCGA GACCCCCCGC GTCCCCTTCC
2161 TCGACCTCAA GGCCGCCTAC GAGGAGCTCC GCGCGGAGAC CGACGCCGCG ATCGCCCGCG
2221 TCCTCGACTC GGGGCGCTAC CTCCTCGGAC CCGAACTCGA AGGATTCGAG GCGGAGTTCG
2281 CCGCGTACTG CGAGACGGAC CACGCCGTCG GCGTGAACAG CGGGATGGAC GCCCTCCAGC
2341 TCGCCCTCCG CGGCCTCGGC ATCGGACCCG GGGACGAGGT GATCGTCCCC TCGCACACGT
2401 ACATCGCCAG CTGGCTCGCG GTGTCCGCCA CCGGCGCGAC CCCCGTGCCC GTCGAGCCGC
2461 ACGAGGACCA CCCCACCCTG GACCCGCTGC TCGTCGAGAA GGCGATCACC CCCCGCACCC
2521 GGGCGCTCCT CCCCGTCCAC CTCTACGGGC ACCCCGCCGA CATGGACGCC CTCCGCGAGC
2581 TCGCGGACCG GCACGGCCTG CACATCGTCG AGGACGCCGC GCAGGCCCAC GGCGCCCGCT
2641 ACCGGGGCCG GCGGATCGGC GCCGGGTCGT CGGTGGCCGC GTTCAGCTTC TACCCGGGCA
2701 AGAACCTCGG CTGCTTCGGC GACGGCGGCG CCGTCGTCAC CGGCGACCCC GAGCTCGCCG
2761 AACGGCTCCG GATGCTCCGC AACTACGGCT CGCGGCAGAA GTACAGCCAC GAGACGAAGG
2821 GCACCAACTC CCGCCTGGAC GAGATGCAGG CCGCCGTGCT GCGGATCCGG CTCGNCCACC
2881 TGGACAGCTG GAACGGCCGC AGGTCGGCGC TGGCCGCGGA GTACCTCTCC GGGCTCGCCG
```

-continued

```
2941 GACTGCCCGG CATCGGCCTG CCGGTGACCG CGCCCGACAC CGACCCGGTC TGGCACCTCT

3001 TCACCGTGCG CACCGAGCGC CGCGACGAGC TGCGCAGCCA CCTCGACGCC CGCGGCATCG

3061 ACACCCTCAC GCACTACCCG GTACCCGTGC ACCTCTCGCC CGCCTACGCG GGCGAGGCAC

3121 CGCCGGAAGG CTCGCTCCCG CGGGCCGAGA GCTTCGCGCG GCAGGTCCTC AGCCTGCCGA

3181 TCGGCCCGCA CCTGGAGCGC CCGCAGGCGC TGCGGGTGAT CGACGCCGTG CGCGAATGGG

3241 CCGAGCGGGT CGACCAGGCC TAGTCAGGTG GTCCGGTAGA CCCAGCAGGC CG
```

Contig 004 from cosmid pKOS023-26 contains 1693 nucleotides and the following ORFs: from nucleotide 1692 to 694 is ORF15, which encodes a part of S-adenosylmethionine synthetase; and from nucleotide 692 to 1 is ORF16, which encodes a part of a protein homologous to the *M. tuberculosis* cbhK gene (SEQ ID NO:23).

```
   1 ATGCGGCACC CCTTGGCGCC GAGCGTGGTG ATCCAGGTGC CGACCCGGGC GAGCACCTCC

61 TGCTCGGTCC AGCCCGTCTT GCTGAGCAGC AGCGCCCGCT CGTAGGCGTT CGTGAACAGC

121 AGCTCGGCTC CGTCGACGAG CTCCCGGACG CTGTCGCCCT CCAGCCGGGC GAGCTGCTGC

181 GAGGGGTCCG CGGCCCGGCG GAGGCCCAGC TCGCGGCAGA CCCGCGTGTG CCGCACCATC

241 GCCTCGGGGT CGTCCGCGCC GACGAGGACG AGGTCGATCC CGCCGGGCCG GCCGGCCGTC

301 TCGCCCAGGT CGATGTCGCG CGCCTCGGCC ATCGCGCCCG CGTAGAACGA GGCGAGCTGA

361 TTGCCGTCCT CGTCGGTGGT GCACATGAAG CGGGCGGTGT GCTGACGGTC CGACACCCGC

421 ACGGAGTCGG TGTCGACGCC CGCGGCGCGG AGCAGCTGCC CGTACCCGTC GAAGTCCTTG

481 CCGACGGCGC CGACGAGGAC GGGGCGGCGA CCGAGCAGGC CGAGGCCGTA CGCGATGTTG

541 GCGGCGACGC CGCCGTGCCG GATGTCCAGG GTGTCGACGA GGAACGACAG GGACACGTGG

601 GCGAGCTGGT CCGGCAGGAT CTGCTCGGCG AAGCGGCCCG GGAAGGTCAT CAGGTGGTCG

661 GTGGCGATCG ACCCGGTGAC GGCTATACGC ATGTCAGAGC CCCGCGGCCT TCTTCAGGGC

721 GTCCACGCGG TCGGTGCGCT CCCAGGTGAA GTCCGGCAGC TCGCGGCCGA AGTGGCCGTA

781 GGCGGCGGTC TGGGAGTAGA TCGGGCGGAG CAGGTCGAGG TCGCGGATGA TCGCGGCCGG

841 GCGGAGGTCG AAGACCTCGC CGATGGCGTT CTCGATCTTC TCGGTCTCGA TCTTGTGGGT

901 GCCGAAGGTC TCGACGAAGA GGCCGACGGG CTCGGCCTTG CCGATCGCGT ACGCGACCTG

961 GACCTCGCAG CGCGAGGCGA GACCGGCGGC GACGACGTTC TTCGCCACCC AGCGCATCGC

1021 GTACGCGGCG GAGCGGTCGA CCTTCGACGG GTCCTTGCCG GAGAAGGCGC CGCCACCGTG

1081 GCGGGCCATG CCGCCGTAGG TGTCGATGAT GATCTTGCGG CCGGTGAGGC CGGCGTCGCC

1141 CATCGGCCG CCGATCTCGA AGCGACCGGT CGGGTTCACG AGCAGGCGGT AGCCGTCGGT

1201 GTCGAGCTTG ATGCCGTCCT CGACGAGCTG CGCAAGCACG TGCTCGACGA CGAACTTCCG

1261 CACGTCGGGG GCGAGCAGCG ACTCCAGGTC GATGTCCGAG GCGTGCTGCG AGGAGACGAC

1321 GACCGTGTCG AGACGGACCG CCCTGTCGCC GTCGTACTCG ATGGTGACCT GGGTCTTGCC

1381 GTCGGGACGC AGGTACGGGA TGGTCCCGTT CTTGCGGACC TCGGTCAGGC GGCGCGAGAG

1441 ACGGTGCGCG AGGTGGATCG GCAGCGGCAT CAGCTCGGGC GTCTCGTCCG AGGCATAGCC

1501 GAACATCAGG CCCTGGTCAC CGGCGCCCTG CTTGTCGAGC TCGTCCCCCT CGTCCCGCTG

1561 GGAGGCACCC TCGACCCGCT TCTCGTACGC GGTGTCGACA CCCTGGGCGA TGTCCGGGGA

1621 CTGCGACCCG ATGGACACCG ACACGCCGCA GGAGGCGCCG TCGAAGCCCT TCTTCGAGGA

1681 GTCGTACCCG ATC
```

Contig 005 from cosmid pKOS023-26 contains 1565 nucleotides and contains the ORF of the picCV gene that encodes PICCV, involved in desosamine biosynthesis (SEQ ID NO:24).

related to narbomycin in structure. The present invention also provides methods of hydroxylating polyketides, which method comprises contacting the polyketide with the recombinant PicK enzyme under conditions such that hydroxyla-

```
   1 CCCCGCTCGC GGCCCCCCAG ACATCCACGC CCACGATTGG ACGCTCCCGA TGACCGCCCC

61 CGCCCTCTCC GCCACCGCCC CGGCCGAACG CTGCGCGCAC CCCGGAGCCG ATCTGGGGGC

121 GGCGGTCCAC GCCGTCGGCC AGACCCTCGC CGCCGGCGGC CTCGTGCCGC CCGACGAGGC

181 CGGAACGACC GCCCGCCACC TCGTCCGGCT CGCCGTGCGC TACGGCAACA GCCCCTTCAC

241 CCCGCTGGAG GAGGCCCGCC ACGACCTGGG CGTCGACCGG GACGCCTTCC GGCGCCTCCT

301 CGCCCTGTTC GGGCAGGTCC CGGAGCTCCG CACCGCGGTC GAGACCGGCC CCGCCGGGGC

361 GTACTGGAAG AACACCCTGC TCCCGCTCGA ACAGCGCGGC GTCTTCGACG CGGCGCTCGC

421 CAGGAAGCCC GTCTTCCCGT ACAGCGTCGG CCTCTACCCC GGCCCGACCT GCATGTTCCG

481 CTGCCACTTC TGCGTCCGTG TGACCGGCGC CCGCTACGAC CCGTCCGCCC TCGACGCCGG

541 CAACGCCATG TTCCGGTCGG TCATCGACGA GATACCCGCG GGCAACCCCT CGGCGATGTA

601 CTTCTCCGGC GGCCTGGAGC CGCTCACCAA CCCCGGCCTC GGGAGCCTGG CCGCGCACGC

661 CACCGACCAC GGCCTGCGGC CCACCGTCTA CACGAACTCC TTCGCGCTCA CCGAGCGCAC

721 CCTGGAGCGC CAGCCCGGCC TCTGGGGCCT GCACGCCATC CGCACCTCGC TCTACGGCCT

781 CAACGACGAG GAGTACGAGC AGACCACCGG CAAGAAGGCC GCCTTCCGCC GCGTCCGCGA

841 GAACCTGCGC CGCTTCCAGC AGCTGCGCGC CGAGCGCGAG TCGCCGATCA ACCTCGGCTT

901 CGCCTACATC GTGCTCCCGG GCCGTGCCTC CCGCCTGCTC GACCTGGTCG ACTTCATCGC

961 CGACCTCAAC GACGCCGGGC AGGGCAGGAC GATCGACTTC GTCAACATTC GCGAGGACTA

1021 CAGCGGCCGT GACGACGGCA AGCTGCCGCA GGAGGAGCGG GCCGAGCTCC AGGAGGCCCT

1081 CAACGCCTTC GAGGAGCGGG TCCGCGAGCG CACCCCCGGA CTCCACATCG ACTACGGCTA

1141 CGCCCTGAAC AGCCTGCGCA CCGGGGCCGA CGCCGAACTG CTGCGGATCA AGCCCGCCAC

1201 CATGCGGCCC ACCGCGCACC CGCAGGTCGC GGTGCAGGTC GATCTCCTCG GCGACGTGTA

1261 CCTGTACCGC GAGGCCGGCT TCCCCGACCT GGACGGCGCG ACCCGCTACA TCGCGGGCCG

1321 CGTGACCCCC GACACCTCCC TCACCGAGGT CGTCAGGGAC TTCGTCGAGC GCGGCGGCGA

1381 GGTGGCGGCC GTCGACGGCG ACGAGTACTT CATGGACGGC TTCGATCAGG TCGTCACCGC

1441 CCGCCTGAAC CAGCTGGAGC GCGACGCCGC GGACGGCTGG GAGGAGGCCC GCGGCTTCCT

1501 GCGCTGACCC GCACCCGCCC CGATCCCCCC GATCCCCCCC CCACGATCCC CCCACCTGAG

1561 GGCCC
```

The recombinant desosamine biosynthesis and transfer and beta-glucosidase genes and proteins provided by the invention are useful in the production of glycosylated polyketides in a variety of host cells, as described in Section IV below.

Section III. The picK Hydroxylase Gene

The present invention provides the picK gene in recombinant form as well as recombinant PicK protein. The availability of the hydroxylase encoded by the picK gene in recombinant form is of significant benefit in that the enzyme can convert narbomycin into picromycin and accepts in addition a variety of polyketide substrates, particularly those tion occurs. This methodology is applicable to large numbers of polyketides.

DNA encoding the picK gene can be isolated from cosmid pKOS023-26 of the invention. The DNA sequence of the picK gene is shown in the preceding section. This DNA sequence encodes one of the recombinant forms of the enzyme provided by the invention. The amino acid sequence of this form of the picK gene is shown below. The present invention also provides a recombinant picK gene that encodes a picK gene product in which the PicK protein is fused to a number of consecutive histidine residues, which facilitates purification from recombinant host cells.

Amino acid sequence of picromycin/methymycin cytochrome P450 hydroxylase, PicK (SEQ ID NO:18).

Amino acid sequence of picromycin/methymycin cytochrome P450
hydroxylase, PicK (SEQ ID NO: 18).

```
  1 VRRTQQGTTA SPPVLDLGAL GQDFAADPYP TYARLRAEGP AHRVRTPEGD EVWLVVGYDR

61 ARAVLADPRF SKDWRNSTTP LTEAEAALNH NMLESDPPRH TRLRKLVARE FTMRRVELLR

121 PRVQEIVDGL VDAMLAAPDG RADLMESLAW PLPITVISEL LGVPEPDRAA FRVWTDAFVF

181 PDDPAQAQTA MAEMSGYLSR LIDSKRGQDG EDLLSALVRT SDEDGSRLTS EELLGMAHIL

241 LVAGHETTVN LIANGMYALL SHPDQLAALR ADMTLLDGAV EEMLRYEGPV ESATYRFPVE

301 PVDLDGTVIP AGDTVLVVLA DAHRTPERFP DPHRFDIRRD TAGHLAFGHG IHFCIGAPLA

361 RLEARIAVRA LLERCPDLAL DVSPGELVWY PNPMIRGLKA LPIRWRRGRE AGRRTG
```

The recombinant PicK enzyme of the invention hydroxylates narbomycin at the C12 position and YC-17 at either the C10 or C12 position. Hydroxylation of these compounds at the respective positions increases the antibiotic activity of the compound relative to the unhydroxylated compound. Hydroxylation can be achieved by a number of methods. First, the hydroxylation may be performed in vitro using purified hydroxylase, or the relevant hydroxylase can be produced recombinantly and utilized directly in the cell that produces it. Thus, hydroxylation may be effected by supplying the nonhydroxylated precursor to a cell that expresses the hydroxylase. These and other details of this embodiment of the invention are described in additional detail below in Section IV and the examples.

Section IV: Heterologous Expression of the Narbonolide PKS; the Desosamine Biosynthetic and Transferase Genes; the Beta-glucosidase Gene; and the picK Hydroxylase Gene In one important embodiment, the invention provides methods for the heterologous expression of one or more of the genes involved in picromycin biosynthesis and recombinant DNA expression vectors useful in the method. Thus, included within the scope of the invention in addition to isolated nucleic acids encoding domains, modules, or proteins of the narbonolide PKS, glycosylation, and/or hydroxylation enzymes, are recombinant expression systems. These systems contain the coding sequences operably linked to promoters, enhancers, and/or termination sequences that operate to effect expression of the coding sequence in compatible host cells. The host cells are modified by transformation with the recombinant DNA expression vectors of the invention to contain these sequences either as extrachromosomal elements or integrated into the chromosome. The invention also provides methods to produce PKS and post-PKS tailoring enzymes as well as polyketides and antibiotics using these modified host cells.

As used herein, the term expression vector refers to a nucleic acid that can be introduced into a host cell or cell-free transcription and translation medium. An expression vector can be maintained stably or transiently in a cell, whether as part of the chromosomal or other DNA in the cell or in any cellular compartment, such as a replicating vector in the cytoplasm. An expression vector also comprises a gene that serves to produce RNA, which typically is translated into a polypeptide in the cell or cell extract. To drive production of the RNA, the expression vector typically comprises one or more promoter elements. Furthermore, expression vectors typically contain additional functional elements, such as, for example, a resistance-conferring gene that acts as a selectable marker.

The various components of an expression vector can vary widely, depending on the intended use of the vector. In particular, the components depend on the host cell(s) in which the vector will be introduced or in which it is intended to function. Components for expression and maintenance of vectors in *E. coli* are widely known and commercially available, as are components for other commonly used organisms, such as yeast cells and *Streptomyces* cells.

One important component is the promoter, which can be referred to as, or can be included within, a control sequence or control element, which drives expression of the desired gene product in the heterologous host cell. Suitable promoters include those that function in eucaryotic or procaryotic host cells. In addition to a promoter, a control element can include, optionally, operator sequences, and other elements, such as ribosome binding sites, depending on the nature of the host. Regulatory sequences that allow for regulation of expression of the heterologous gene relative to the growth of the host cell may also be included. Examples of such regulatory sequences known to those of skill in the art are those that cause the expression of a gene to be turned on or off in response to a chemical or physical stimulus.

Preferred host cells for purposes of selecting vector components include fungal host cells such as yeast and procaryotic, especially *E. coli* and *Streptomyces*, host cells, but single cell cultures of, for example, mammalian cells can also be used. In hosts such as yeasts, plants, or mammalian cells that ordinarily do not produce polyketides, it may be necessary to provide, also typically by recombinant means, suitable holo-ACP synthases to convert the recombinantly produced PKS to functionality. Provision of such enzymes is described, for example, in PCT publication Nos. WO 97/13845 and 98/27203, each of which is incorporated herein by reference. Control systems for expression in yeast, including controls that effect secretion are widely available and can be routinely used. For *E. coli* or other bacterial host cells, promoters such as those derived from sugar metabolizing enzymes, such as galactose, lactose (lac), and maltose, can be used. Additional examples include promoters derived from genes encoding biosynthetic enzymes, and the tryptophan (trp), the beta-lactamase (bla), bacteriophage lambda PL, and T5 promoters. In addition, synthetic promoters, such as the tac promoter (U.S. Pat. No. 4,551,433), can also be used.

Particularly preferred are control sequences compatible with *Streptomyces*spp. Particularly useful promoters for *Streptomyces* host cells include those from PKS gene clusters that result in the production of polyketides as secondary metabolites, including promoters from aromatic (Type II) PKS gene clusters. Examples of Type II PKS gene cluster promoters are act gene promoters and tcm gene promoters; an example of a Type I PKS gene cluster promoter is the spiramycin PKS gene promoter.

If a *Streptomyces* or other host ordinarily produces polyketides, it may be desirable to modify the host so as to prevent the production of endogenous polyketides prior to its use to express a recombinant PKS of the invention. Such hosts have been described, for example, in U.S. Pat. No. 5,672,491, incorporated herein by reference. In such hosts, it may not be necessary to provide enzymatic activities for all of the desired post-translational modifications of the enzymes that make up the recombinantly produced PKS, because the host naturally expresses such enzymes. In particular, these hosts generally contain holo-ACP synthases that provide the pantotheinyl residue needed for functionality of the PKS.

Thus, in one important embodiment, the vectors of the invention are used to transform *Streptomyces* host cells to provide the recombinant *Streptomyces* host cells of the invention. *Streptomyces* is a convenient host for expressing narbonolide or 10-deoxymethynolide or derivatives of those compounds, because narbonolide and 10-deoxymethynolide are naturally produced in certain *Streptomyces* species, and *Streptomyces* generally produce the precursors needed to form the desired polyketide. The present invention also provides the narbonolide PKS gene promoter in recombinant form, located upstream of the picAI gene on cosmid pKOS023-27. This promoter can be used to drive expression of the narbonolide PKS or any other coding sequence of interest in host cells in which the promoter functions, particularly *S. venezuelae* and generally any *Streptomyces* species. As described below, however, promoters other than the promoter of the narbonolide PKS genes will typically be used for heterologous expression.

For purposes of the invention, any host cell other than *Streptomyces venezuelae* is a heterologous host cell. Thus, *S. narbonensis*, which produces narbomycin but not picromycin is a heterologous host cell of the invention, although other host cells are generally preferred for purposes of heterologous expression. Those of skill in the art will recognize that, if a *Streptomyces* host that produces a picromycin or methymycin precursor is used as the host cell, the recombinant vector need drive expression of only a portion of the genes constituting the picromycin gene cluster. As used herein, the picromycin gene cluster includes the narbonolide PKS, the desosamine biosynthetic and transferase genes, the beta-glucosidase gene, and the picK hydroxylase gene. Thus, such a vector may comprise only a single ORF, with the desired remainder of the polypeptides encoded by the picromycin gene cluster provided by the genes on the host cell chromosomal DNA.

The present invention also provides compounds and recombinant DNA vectors useful for disrupting any gene in the picromycin gene cluster (as described above and illustrated in the examples below). Thus, the invention provides a variety of modified host cells (particularly, *S. narbonensis* and *S. venezuelae*) in which one or more of the genes in the picromycin gene cluster have been disrupted. These cells are especially useful when it is desired to replace the disrupted function with a gene product expressed by a recombinant DNA vector. Thus, the invention provides such *Streptomyces* host cells, which are preferred host cells for expressing narbonolide derivatives of the invention. Particularly preferred host cells of this type include those in which the coding sequence for the loading module has been disrupted, those in which one or more of any of the PKS gene ORFs has been disrupted, and/or those in which the picK gene has been disrupted.

In a preferred embodiment, the expression vectors of the invention are used to construct a heterologous recombinant *Streptomyces* host cell that expresses a recombinant PKS of the invention. As noted above, a heterologous host cell for purposes of the present invention is any host cell other than *S. venezuelae*, and in most cases other than *S. narbonensis* as well. Particularly preferred heterologous host cells are those which lack endogenous functional PKS genes. Illustrative host cells of this type include the modified *Streptomyces coelicolor* CH999 and similarly modified *S. lividans* described in PCT publication No. WO 96/40968.

The invention provides a wide variety of expression vectors for use in *Streptomyces*. For replicating vectors, the origin of replication can be, for example and without limitation, a low copy number vector, such as SCP2* (see Hopwood et al., *Genetic Manipulation of Streptomyces: A Laboratory manual* (The John Innes Foundation, Norwich, U.K., 1985); Lydiate et al., 1985, *Gene* 35: 223–235; and Kieser and Melton, 1988, *Gene* 65: 83–91, each of which is incorporated herein by reference), SLP1.2 (Thompson et al., 1982, *Gene* 20: 51–62, incorporated herein by reference), and pSG5(ts) (Muth et al., 1989, *Mol. Gen. Genet.* 219: 341–348, and Bierman et al., 1992, *Gene* 116: 43–49, each of which is incorporated herein by reference), or a high copy number vector, such as pIJ101 and pJV1 (see Katz et al., 1983, *J. Gen. Microbiol.* 129: 2703–2714; Vara et al., 1989, *J. Bacteriol.* 171: 5782–5781; and Servin-Gonzalez, 1993, *Plasmid* 30: 131–140, each of which is incorporated herein by reference). High copy number vectors are generally, however, not preferred for expression of large genes or multiple genes. For non-replicating and integrating vectors and generally for any vector, it is useful to include at least an *E. coli* origin of replication, such as from pUC, p1P, p1I, and pBR. For phage based vectors, the phage phiC31 and its derivative KC515 can be employed (see Hopwood et al., supra). Also, plasmid pSET152, plasmid pSAM, plasmids pSE101 and pSE211, all of which integrate site-specifically in the chromosomal DNA of *S. lividans*, can be employed.

Preferred *Streptomyces* host cell/vector combinations of the invention include *S. coelicolor* CH999 and *S. lividans* K4-114 host cells, which do not produce actinorhodin, and expression vectors derived from the pRM1 and pRM5 vectors, as described in U.S. Pat. No. 5,830,750 and U.S. patent application Ser. No. 08/828,898, filed Mar. 31, 1997, and Ser. No. 09/181,833, filed Oct. 28, 1998, each of which is incorporated herein by reference.

As described above, particularly useful control sequences are those that alone or together with suitable regulatory systems activate expression during transition from growth to stationary phase in the vegetative mycelium. The system contained in the illustrative plasmid pRM5, i.e., the actI/actIII promoter pair and the actII-ORF4 activator gene, is particularly preferred. Other useful *Streptomyces* promoters include without limitation those from the ermE gene and the melC1 gene, which act constitutively, and the tipA gene and the merA gene, which can be induced at any growth stage. In addition, the T7 RNA polymerase system has been transferred to *Streptomyces* and can be employed in the vectors and host cells of the invention. In this system, the coding sequence for the T7 RNA polymerase is inserted into a neutral site of the chromosome or in a vector under the control of the inducible merA promoter, and the gene of interest is placed under the control of the T7 promoter. As noted above, one or more activator genes can also be employed to enhance the activity of a promoter. Activator genes in addition to the actII-ORF4 gene described above include dnrI, redD, and ptpA genes (see U.S. patent application Ser. No. 09/181,833, supra).

Typically, the expression vector will comprise one or more marker genes by which host cells containing the vector can be identified and/or selected. Selectable markers are often preferred for recombinant expression vectors. A variety of markers are known that are useful in selecting for transformed cell lines and generally comprise a gene that confers a selectable phenotype on transformed cells when the cells are grown in an appropriate selective medium. Such markers include, for example, genes that confer antibiotic resistance or sensitivity to the plasmid. Alternatively, several polyketides are naturally colored, and this characteristic can provide a built-in marker for identifying cells. Preferred selectable markers include antibiotic resistance conferring genes. Preferred for use in *Streptomyces* host cells are the ermE (confers resistance to erythromycin and lincomycin), tsr (confers resistance to thiostrepton), aadA (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes.

To provide a preferred host cell and vector for purposes of the invention, the narbonolide PKS genes were placed on a recombinant expression vector that was transferred to the non-macrolide producing host *Streptomyces lividans* K4-114, as described in Example 3. Transformation of *S. lividans* K4-114 with this expression vector resulted in a strain which produced two compounds in similar yield (~5–10 mg/L each). Analysis of extracts by LC/MS followed by $^1$H-NMR spectroscopy of the purified compounds established their identity as narbonolide (FIG. 5, compound 4) and 10-deoxymethynolide (FIG. 5, compound 5), the respective 14 and 12-membered polyketide precursors of narbomycin and YC17.

To provide a host cell of the invention that produces the narbonolide PKS as well as an additional narbonolide biosynthetic gene and to investigate the possible role of the Pik TEII in picromycin biosynthesis, the picB gene was integrated into the chromosome to provide the host cell of the invention *Streptomyces lividans* K39-18. The picB gene was cloned into the *Streptomyces* genome integrating vector pSET152 (see Bierman et al., 1992, *Gene* 116:43, incorporated herein by reference) under control of the same promoter (PactI) as the PKS on plasmid pKOS039-86.

A comparison of strains *Streptomyces lividans* K39-18/pKOS039-86 and K4-114/pKOS039-86 grown under identical conditions indicated that the strain containing TEII produced 4–7 times more total polyketide. This increased production indicates that the enzyme is functional in this strain and is consistent with the observation that yields fall to below 5% for both picromycin and methymycin when picB is disrupted in *S. venezuelae*. Because the production levels of compound 4 and 5 from K39-18/pKOS03986 increased by the same relative amounts, TEII does not appear to influence the ratio of 12 and 14-membered lactone ring formation. Thus, the invention provides methods of coexpressing the picB gene product or any other type II thioesterase with the narbonolide PKS or any other PKS in heterologous host cells to increase polyketide production.

In accordance with the methods of the invention, picromycin biosynthetic genes in addition to the genes encoding the PKS and Pik TEII can be introduced into heterologous host cells. In particular, the picK gene, desosamine biosynthetic genes, and the desosaminyl transferase gene can be expressed in the recombinant host cells of the invention to produce any and all of the polyketides in the picromycin biosynthetic pathway (or derivatives thereof). Those of skill will recognize that the present invention enables one to select whether only the 12-membered polyketides, or only the 14-membered polyketides, or both 12- and 14-membered polyketides will be produced. To produce only the 12-membered polyketides, the invention provides expression vectors in which the last module is deleted or the KS domain of that module is deleted or rendered inactive. To produce only the 14-membered polyketides, the invention provides expression vectors in which the coding sequences of extender modules 5 and 6 are fused to provide only a single polypeptide.

In one important embodiment, the invention provides methods for desosaminylating polyketides or other compounds. In this method, a host cell other than *Streptomyces venezuelae* is transformed with one or more recombinant vectors of the invention comprising the desosamine biosynthetic and desosaminyl transferase genes and control sequences positioned to express those genes. The host cells so transformed can either produce the polyketide to be desosaminylated naturally or can be transformed with expression vectors encoding the PKS that produces the desired polyketide. Alternatively, the polyketide can be supplied to the host cell containing those genes. Upon production of the polyketide and expression of the desosamine biosynthetic and desosaminyl transferase genes, the desired desosaminylated polyketide is produced. This method is especially useful in the production of polyketides to be used as antibiotics, because the presence of the desosamine residue is known to increase, relative to their undesosaminylated counterparts, the antibiotic activity of many polyketides significantly. The present invention also provides a method for desosaminylating a polyketide by transforming an *S. venezuelae* or *S. narbonensis* host cell with a recombinant vector that encodes a PKS that produces the polyketide and culturing the transformed cell under conditions such that said polyketide is produced and desosaminylated. In this method, use of an *S. venezuelae* or *S. narbonensis* host cell of the invention that does not produce a functional endogenous narbonolide PKS is preferred.

In a related aspect, the invention provides a method for improving the yield of a desired desosaminylated polyketide in a host cell, which method comprises transforming the host cell with a beta-glucosidase gene. This method is not limited to host cells that have been transformed with expression vectors of the invention encoding the desosamine biosynthetic and desosaminyl transferase genes of the invention but instead can be applied to any host cell that desosaminylates polyketides or other compounds. Moreover, while the beta-glucosidase gene from *Streptomyces venezuelae* provided by the invention is preferred for use in the method, any beta-glucosidase gene may be employed. In another embodiment, the beta-glucosidase treatment is conducted in a cell free extract.

Thus, the invention provides methods not only for producing narbonolide and 10-deoxymethynolide in heterologous host cells but also for producing narbomycin and YC-17 in heterologous host cells. In addition, the invention provides methods for expressing the picK gene product in heterologous host cells, thus providing a means to produce picromycin, methymycin, and neomethymycin in heterologous host cells. Moreover, because the recombinant expression vectors provided by the invention enable the artisan to provide for desosamine biosynthesis and transfer and/or C10 or C12 hydroxylation in any host cell, the invention provides methods and reagents for producing a very wide variety of glycosylated and/or hydroxylated polyketides. This variety of polyketides provided by the invention can be better appreciated upon consideration of the following section relating to the production of polyketides from heterologous or hybrid PKS enzymes provided by the invention.

Section V: Hybrid PKS Genes

The present invention provides recombinant DNA compounds encoding each of the domains of each of the modules of the narbonolide PKS, the proteins involved in desosamine biosynthesis and transfer to narbonolide, and the PicK protein. The availability of these compounds permits their use in recombinant procedures for production of desired portions of the narbonolide PKS fused to or expressed in conjunction with all or a portion of a heterologous PKS. The resulting hybrid PKS can then be expressed in a host cell, optionally with the desosamine biosynthesis and transfer genes and/or the picK hydroxylase gene to produce a desired polyketide.

Thus, in accordance with the methods of the invention, a portion of the narbonolide PKS coding sequence that encodes a particular activity can be isolated and manipulated, for example, to replace the corresponding region in a different modular PKS. In addition, coding sequences for individual modules of the PKS can be ligated into suitable expression systems and used to produce the portion of the protein encoded. The resulting protein can be isolated and purified or can may be employed in situ to effect polyketide synthesis. Depending on the host for the recombinant production of the domain, module, protein, or combination of proteins, suitable control sequences such as promoters, termination sequences, enhancers, and the like are ligated to the nucleotide sequence encoding the desired protein in the construction of the expression vector.

In one important embodiment, the invention thus provides a hybrid PKS and the corresponding recombinant DNA compounds that encode those hybrid PKS enzymes. For purposes of the invention, a hybrid PKS is a recombinant PKS that comprises all or part of one or more extender modules, loading module, and/or thioesterase/cyclase domain of a first PKS and all or part of one or more extender modules, loading module, and/or thioesterase/cyclase domain of a second PKS. In one preferred embodiment, the first PKS is most but not all of the narbonolide PKS, and the second PKS is only a portion or all of a non-narbonolide PKS. An illustrative example of such a hybrid PKS includes a narbonolide PKS in which the natural loading module has been replaced with a loading module of another PKS. Another example of such a hybrid PKS is a narbonolide PKS in which the AT domain of extender module 3 is replaced with an AT domain that binds only malonyl CoA.

In another preferred embodiment, the first PKS is most but not all of a non-narbonolide PKS, and the second PKS is only a portion or all of the narbonolide PKS. An illustrative example of such a hybrid PKS includes a DEBS PKS in which an AT specific for methylmalonyl CoA is replaced with the AT from the narbonolide PKS specific for malonyl CoA.

Those of skill in the art will recognize that all or part of either the first or second PKS in a hybrid PKS of the invention need not be isolated from a naturally occurring source. For example, only a small portion of an AT domain determines its specificity. See U.S. provisional patent application Serial No. 60/091,526, and Lau et al., infra, incorporated herein by reference. The state of the art in DNA synthesis allows the artisan to construct de novo DNA compounds of size sufficient to construct a useful portion of a PKS module or domain. Thus, the desired derivative coding sequences can be synthesized using standard solid phase synthesis methods such as those described by Jaye et al., 1984, *J. Biol. Chem.* 259: 6331, and instruments for automated synthesis are available commercially from, for example, Applied Biosystems, Inc. For purposes of the invention, such synthetic DNA compounds are deemed to be a portion of a PKS.

With this general background regarding hybrid PKSs of the invention, one can better appreciate the benefit provided by the DNA compounds of the invention that encode the individual domains, modules, and proteins that comprise the narbonolide PKS. As described above, the narbonolide PKS is comprised of a loading module, six extender modules composed of a KS, AT, ACP, and zero, one, two, or three KR, DH, and ER domains, and a thioesterase domain. The DNA compounds of the invention that encode these domains individually or in combination are useful in the construction of the hybrid PKS encoding DNA compounds of the invention.

The recombinant DNA compounds of the invention that encode the loading module of the narbonolide PKS and the corresponding polypeptides encoded thereby are useful for a variety of applications. In one embodiment, a DNA compound comprising a sequence that encodes the narbonolide PKS loading module is inserted into a DNA compound that comprises the coding sequence for a heterologous PKS. The resulting construct, in which the coding sequence for the loading module of the heterologous PKS is replaced by that for the coding sequence of the narbonolide PKS loading module provides a novel PKS. Examples include the 6-deoxyerythronolide B, rapamycin, FK506, FK520, rifamycin, and avermectin PKS coding sequences. In another embodiment, a DNA compound comprising a sequence that encodes the narbonolide PKS loading module is inserted into a DNA compound that comprises the coding sequence for the narbonolide PKS or a recombinant narbonolide PKS that produces a narbonolide derivative.

In another embodiment, a portion of the loading module coding sequence is utilized in conjunction with a heterologous coding sequence. In this embodiment, the invention provides, for example, replacing the propionyl CoA specific AT with an acetyl CoA, butyryl CoA, or other CoA specific AT. In addition, the $KS^Q$ and/or ACP can be replaced by another inactivated KS and/or another ACP. Alternatively, the $KS^Q$, AT, and ACP of the loading module can be replaced by an AT and ACP of a loading module such as that of DEBS. The resulting heterologous loading module coding sequence can be utilized in conjunction with a coding sequence for a PKS that synthesizes narbonolide, a narbonolide derivative, or another polyketide.

The recombinant DNA compounds of the invention that encode the first extender module of the narbonolide PKS and the corresponding polypeptides encoded thereby are useful for a variety of applications. In one embodiment, a DNA compound comprising a sequence that encodes the narbonolide PKS first extender module is inserted into a DNA compound that comprises the coding sequence for a heterologous PKS. The resulting construct, in which the coding sequence for a module of the heterologous PKS is either replaced by that for the first extender module of the narbonolide PKS or the latter is merely added to coding sequences for modules of the heterologous PKS, provides a novel PKS coding sequence. In another embodiment, a DNA compound comprising a sequence that encodes the first extender module of the narbonolide PKS is inserted into a DNA compound that comprises coding sequences for the narbonolide PKS or a recombinant narbonolide PKS that produces a narbonolide derivative.

In another embodiment, a portion or all of the first extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or carboxyglycolyl CoA specific AT; deleting (which includes inactivating) the KR; inserting a DH or a DH and ER; and/or replacing the KR with another KR, a DH and KR, or a DH, KR, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the narbonolide PKS, from a gene for a PKS that produces a polyketide other than narbonolide, or from chemical synthesis. The resulting heterologous first extender module coding sequence can be utilized in conjunction with a coding sequence for a PKS that synthesizes narbonolide, a narbonolide derivative, or another polyketide.

In an illustrative embodiment of this aspect of the invention, the invention provides recombinant PKSs and recombinant DNA compounds and vectors that encode such PKSs in which the KS domain of the first extender module has been inactivated. Such constructs are especially useful when placed in translational reading frame with the remaining modules and domains of a narbonolide PKS or narbonolide derivative PKS. The utility of these constructs is that host cells expressing, or cell free extracts containing, the PKS encoded thereby can be fed or supplied with N-acetylcysteamine thioesters of novel precursor molecules to prepare narbonolide derivatives. See U.S. patent application Ser. No. 60/117,384, filed 27 Jan. 1999, and PCT publication Nos. WO 99/03986 and 97/02358, each of which is incorporated herein by reference.

The recombinant DNA compounds of the invention that encode the second extender module of the narbonolide PKS and the corresponding polypeptides encoded thereby are useful for a variety of applications. In one embodiment, a DNA compound comprising a sequence that encodes the narbonolide PKS second extender module is inserted into a DNA compound that comprises the coding sequence for a heterologous PKS. The resulting construct, in which the coding sequence for a module of the heterologous PKS is either replaced by that for the second extender module of the narbonolide PKS or the latter is merely added to coding sequences for the modules of the heterologous PKS, provides a novel PKS. In another embodiment, a DNA compound comprising a sequence that encodes the second extender module of the narbonolide PKS is inserted into a DNA compound that comprises the coding sequences for the narbonolide PKS or a recombinant narbonolide PKS that produces a narbonolide derivative.

In another embodiment, a portion or all of the second extender module coding sequence is utilized in conjunction with other PKS coding sequences to create a hybrid module. In this embodiment, the invention provides, for example, replacing the malonyl CoA specific AT with a methylmalonyl CoA, ethylmalonyl CoA, or carboxyglycolyl CoA specific AT; deleting (or inactivating) the KR, the DH, or both the DH and KR; replacing the KR or the KR and DH with a KR, a KR and a DH, or a KR, DH, and ER; and/or inserting an ER. In addition, the KS and/or ACP can be replaced with another KS and/or ACP. In each of these replacements or insertions, the heterologous KS, AT, DH, KR, ER, or ACP coding sequence can originate from a coding sequence for another module of the narbonolide PKS, from a coding sequence for a PKS that produces a polyketide other than narbonolide, or from chemical synthesis. The resulting heterologous second extender module coding sequence can be utilized in conjunction with a coding sequence from a PKS that synthesizes narbonolide, a narbonolide derivative, or another polyketide.

The recombinant DNA compounds of the invention that encode the third extender module of the narbonolide PKS and the corresponding polypeptides encoded thereby are useful for a variety of applications. In one embodiment, a DNA compound comprising a sequence that encodes the narbonolide PKS third extender module is inserted into a DNA compound that comprises the coding sequence for a heterologous PKS. The resulting construct, in which the coding sequence for a module of the heterologous PKS is either replaced by that for the third extender module of the narbonolide PKS or the latter is merely added to coding sequences for the modules of the heterologous PKS, provides a novel PKS. In another embodiment, a DNA compound comprising a sequence that encodes the third extender module of the narbonolide PKS is inserted into a DNA compound that comprises coding sequences for the narbonolide PKS or a recombinant narbonolide PKS that produces a narbonolide derivative.

In another embodiment, a portion or all of the third extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or carboxyglycolyl CoA specific AT; deleting the inactive KR; and/or inserting a KR, or a KR and DH, or a KR, DH, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the narbonolide PKS, from a gene for a PKS that produces a polyketide other than narbonolide, or from chemical synthesis. The resulting heterologous third extender module coding sequence can be utilized in conjunction with a coding sequence for a PKS that synthesizes narbonolide, a narbonolide derivative, or another polyketide.

The recombinant DNA compounds of the invention that encode the fourth extender module of the narbonolide PKS and the corresponding polypeptides encoded thereby are useful for a variety of applications. In one embodiment, a DNA compound comprising a sequence that encodes the narbonolide PKS fourth extender module is inserted into a DNA compound that comprises the coding sequence for a heterologous PKS. The resulting construct, in which the coding sequence for a module of the heterologous PKS is either replaced by that for the fourth extender module of the narbonolide PKS or the latter is merely added to coding sequences for the modules of the heterologous PKS, provides a novel PKS. In another embodiment, a DNA compound comprising a sequence that encodes the fourth extender module of the narbonolide PKS is inserted into a DNA compound that comprises coding sequences for the narbonolide PKS or a recombinant narbonolide PKS that produces a narbonolide derivative.

In another embodiment, a portion of the fourth extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or carboxyglycolyl CoA specific AT; deleting any one, two, or all three of the ER, DH, and KR; and/or replacing any one, two, or all three of the ER, DH, and KR with either a KR, a DH and KR, or a KR, DH, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the narbonolide PKS, from a coding sequence for a PKS that produces a polyketide other than narbonolide, or from chemical synthesis. The resulting heterologous fourth extender module coding sequence can be utilized in conjunction with a coding sequence for a PKS that synthesizes narbonolide, a narbonolide derivative, or another polyketide.

The recombinant DNA compounds of the invention that encode the fifth extender module of the narbonolide PKS and the corresponding polypeptides encoded thereby are useful for a variety of applications. In one embodiment, a DNA compound comprising a sequence that encodes the narbonolide PKS fifth extender module is inserted into a DNA compound that comprises the coding sequence for a heterologous PKS. The resulting construct, in which the coding sequence for a module of the heterologous PKS is either replaced by that for the fifth extender module of the narbonolide PKS or the latter is merely added to coding sequences for the modules of the heterologous PKS, provides a novel PKS. In another embodiment, a DNA compound comprising a sequence that encodes the fifth extender module of the narbonolide PKS is inserted into a DNA compound that comprises the coding sequence for the narbonolide PKS or a recombinant narbonolide PKS that produces a narbonolide derivative.

In another embodiment, a portion or all of the fifth extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or carboxyglycolyl CoA specific AT; deleting (or inactivating) the KR; inserting a DH or a DH and ER; and/or replacing the KR with another KR, a DH and KR, or a DH, KR, and ER. In addition, the KS and/or ACP can be replaced with another KS and/or ACP. In each of these replacements or insertions, the heterologous KS, AT, DH, KR, ER, or ACP coding sequence can originate from a coding sequence for another module of the narbonolide PKS, from a coding sequence for a PKS that produces a polyketide other than narbonolide, or from chemical synthesis. The resulting heterologous fifth extender module coding sequence can be utilized in conjunction with a coding sequence for a PKS that synthesizes narbonolide, a narbonolide derivative, or another polyketide.

The recombinant DNA compounds of the invention that encode the sixth extender module of the narbonolide PKS and the corresponding polypeptides encoded thereby are useful for a variety of applications. In one embodiment, a DNA compound comprising a sequence that encodes the narbonolide PKS sixth extender module is inserted into a DNA compound that comprises the coding sequence for a heterologous PKS. The resulting construct, in which the coding sequence for a module of the heterologous PKS is either replaced by that for the sixth extender module of the narbonolide PKS or the latter is merely added to coding sequences for the modules of the heterologous PKS, provides a novel PKS. In another embodiment, a DNA compound comprising a sequence that encodes the sixth extender module of the narbonolide PKS is inserted into a DNA compound that comprises the coding sequences for the narbonolide PKS or a recombinant narbonolide PKS that produces a narbonolide derivative.

In another embodiment, a portion or all of the sixth extender module coding sequence is utilized in conjunction with other PKS coding sequences to create a hybrid module. In this embodiment, the invention provides, for example, replacing the methylmalonyl CoA specific AT with a malonyl CoA, ethylmalonyl CoA, or carboxyglycolyl CoA specific AT; and/or inserting a KR, a KR and DH, or a KR, DH, and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the narbonolide PKS, from a coding sequence for a PKS that produces a polyketide other than narbonolide, or from chemical synthesis. The resulting heterologous sixth extender module coding sequence can be utilized in conjunction with a coding sequence for a PKS that synthesizes narbonolide, a narbonolide derivative, or another polyketide.

The sixth extender module of the narbonolide PKS is followed by a thioesterase domain. This domain is important in the cyclization of the polyketide and its cleavage from the PKS. The present invention provides recombinant DNA compounds that encode hybrid PKS enzymes in which the narbonolide PKS is fused to a heterologous thioesterase or a heterologous PKS is fused to the narbonolide synthase thioesterase. Thus, for example, a thioesterase domain coding sequence from another PKS gene can be inserted at the end of the sixth extender module coding sequence in recombinant DNA compounds of the invention. Recombinant DNA compounds encoding this thioesterase domain are therefore useful in constructing DNA compounds that encode the narbonolide PKS, a PKS that produces a narbonolide derivative, and a PKS that produces a polyketide other than narbonolide or a narbonolide derivative.

The following Table lists references describing illustrative PKS genes and corresponding enzymes that can be utilized in the construction of the recombinant hybrid PKSs and the corresponding DNA compounds that encode them of the invention. Also presented are various references describing tailoring enzymes and corresponding genes that can be employed in accordance with the methods of the invention.

Avermectin
   U.S. Pat. No. 5,252,474 to Merck.
   MacNeil et al., 1993, *Industrial Microorganisms: Basic and Applied Molecular Genetics*, Baltz, Hegeman, & Skatrud, eds. (ASM), pp. 245–256, A Comparison of the Genes Encoding the Polyketide Synthases for Avermectin, Erythromycin, and Nemadectin.
   MacNeil et al., 1992, *Gene* 115: 119–125, Complex Organization of the *Streptomyces avermitilis* genes encoding the avermectin polyketide synthase.

Candicidin (FR008)
   Hu et al., 1994, *Mol. Microbiol.* 14: 163–172.

Epothilone
   U.S. patent application Ser. No. 60/130,560, filed 22 Apr. 1999, and Ser. No. 60/122,620, filed 3 Mar. 3, 1999.

Erythromycin
   PCT Pub. No. 93/13663 to Abbott.
   U.S. Pat. No. 5,824,513 to Abbott.
   Donadio et al., 1991, *Science* 252:675–9.
   Cortes et al., 8 Nov. 1990, *Nature* 348:176–8, An unusually large multifunctional polypeptide in the erythromycin producing polyketide synthase of *Saccharopolyspora erythraea*.
   Glycosylation Enzymes
   PCT Pat. App. Pub. No. 97/23630 to Abbott.

FK506
   Motamedi et al., 1998, The biosynthetic gene cluster for the macrolactone ring of the immunosuppressant FK506, *Eur. J. biochem.* 256: 528–534.
   Motamedi et al., 1997, Structural organization of a multifunctional polyketide synthase involved in the biosynthesis of the macrolide immunosuppressant FK506, *Eur. J. Biochem.* 244: 74–80.

Methyltransferase

U.S. Pat. No. 5,264,355, issued 23 Nov. 1993, Methylating enzyme from *Streptomyces* MA6858.31-O-desmethyl-FK506 methyltransferase.

Motamedi et al., 1996, Characterization of methyltransferase and hydroxylase genes involved in the biosynthesis of the immunosuppressants FK506 and FK520, *J. Bacteriol.* 178: 5243–5248.

FK520

U.S. patent application Ser. No. 60/123,810, filed 11 Mar. 1999.

Immunomycin

Nielsen et al., 1991, *Biochem.* 30:5789–96.

Lovastatin

U.S. Pat. No. 5,744,350 to Merck.

Nemadectin

MacNeil et al., 1993, supra.

Niddamycin

Kakavas et al., 1997, Identification and characterization of the niddamycin polyketide synthase genes from *Streptomyces caelestis*, *J. Bacteriol.* 179: 7515–7522.

Oleandomycin

Swan et al., 1994, Characterisation of a *Streptomyces antibioticus* gene encoding a type I polyketide synthase which has an unusual coding sequence, *Mol. Gen. Genet.* 242: 358–362.

Olano et al., 1998, Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299–308.

U.S. patent application Ser. No. 60/120,254, filed 16 Feb. 1999, and Ser. No. 60/106,000, filed 29 Oct. 1998.

Platenolide

EP Pat. App. Pub. No. 791,656 to Lilly.

Pradimicin

PCT Pat. Pub. No. WO 98/11230 to Bristol-Myers Squibb.

Rapamycin

Schwecke et al., August 1995, The biosynthetic gene cluster for the polyketide rapamycin, *Proc. Natl. Acad. Sci. USA* 92:7839–7843.

Aparicio et al., 1996, Organization of the biosynthetic gene cluster for rapamycin in *Streptomyces hygroscopicus*: analysis of the enzymatic domains in the modular polyketide synthase, *Gene* 169: 9–16.

Rifamycin

August et al., 13 Feb. 1998, Biosynthesis of the ansamycin antibiotic rifamycin: deductions from the molecular analysis of the rif biosynthetic gene cluster of *Amycolatopsis mediterranei* S669, *Chemistry & Biology*, 5(2): 69–79.

Soraphen

U.S. Pat. No. 5,716,849 to Novartis.

Schupp et al., 1995, *J. Bacteriology* 177: 3673–3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.

Spiramycin

U.S. Pat. No. 5,098,837 to Lilly.

Activator Gene

U.S. Pat. No. 5,514,544 to Lilly.

Tylosin

EP Pub. No. 791,655 to Lilly.

Kuhstoss et al., 1996, *Gene* 183:231–6., Production of a novel polyketide through the construction of a hybrid polyketide synthase.

U.S. Pat. No. 5,876,991 to Lilly.

Tailoring enzymes

Merson-Davies and Cundliffe, 1994, *Mol. Microbiol.* 13: 349–355. Analysis of five tylosin biosynthetic genes from the tylBA region of the *Streptomyces fradiae* genome.

As the above Table illustrates, there are a wide variety of PKS genes that serve as readily available sources of DNA and sequence information for use in constructing the hybrid PKS-encoding DNA compounds of the invention. Methods for constructing hybrid PKS-encoding DNA compounds are described without reference to the narbonolide PKS in U.S. Pat. Nos. 5,672,491 and 5,712,146 and PCT publication No. 98/49315, each of which is incorporated herein by reference.

In constructing hybrid PKSs of the invention, certain general methods may be helpful. For example, it is often beneficial to retain the framework of the module to be altered to make the hybrid PKS. Thus, if one desires to add DH and ER functionalities to a module, it is often preferred to replace the KR domain of the original module with a KR, DH, and ER domain-containing segment from another module, instead of merely inserting DH and ER domains. One can alter the stereochemical specificity of a module by replacement of the KS domain with a KS domain from a module that specifies a different stereochemistry. See Lau et al., 1999, Dissecting the role of acyltransferase domains of modular polyketide synthases in the choice and stereochemical fate of extender units "*Biochemistry* 38(5):1643–1651, incorporated herein by reference. One can alter the specificity of an AT domain by changing only a small segment of the domain. See Lau et al., supra. One can also take advantage of known linker regions in PKS proteins to link modules from two different PKSs to create a hybrid PKS. See Gokhale et al., 16 Apr. 1999, Dissecting and Exploiting Intermodular Communication in Polyketide Synthases", *Science* 284: 482–485, incorporated herein by reference.

The hybrid PKS-encoding DNA compounds of the invention can be and often are hybrids of more than two PKS genes. Even where only two genes are used, there are often two or more modules in the hybrid gene in which all or part of the module is derived from a second (or third) PKS gene. Thus, as one illustrative example, the invention provides a hybrid narbonolide PKS that contains the naturally occurring loading module and thioesterase domain as well as extender modules one, two, four, and six of the narbonolide PKS and further contains hybrid or heterologous extender modules three and five. Hybrid or heterologous extender modules three and five contain AT domains specific for malonyl CoA and derived from, for example, the rapamycin PKS genes.

To construct a hybrid PKS or narbonolide derivative PKS of the invention, one can employ a technique, described in PCT Pub. No. 98/27203, which is incorporated herein by reference, in which the large PKS gene cluster is divided into two or more, typically three, segments, and each segment is placed on a separate expression vector. In this manner, each of the segments of the gene can be altered, and various altered segments can be combined in a single host cell to provide a recombinant PKS gene of the invention. This technique makes more efficient the construction of large libraries of recombinant PKS genes, vectors for expressing those genes, and host cells comprising those vectors.

The invention also provides libraries of PKS genes, PKS proteins, and ultimately, of polyketides, that are constructed by generating modifications in the narbonolide PKS so that the protein complexes produced have altered activities in one or more respects and thus produce polyketides other than the natural product of the PKS. Novel polyketides may thus be prepared, or polyketides in general prepared more readily, using this method. By providing a large number of different genes or gene clusters derived from a naturally occurring PKS gene cluster, each of which has been modified in a different way from the native cluster, an effectively combinatorial library of polyketides can be produced as a result of the multiple variations in these activities. As will be further described below, the metes and bounds of this embodiment of the invention can be described on both the protein level and the encoding nucleotide sequence level.

As described above, a modular PKS "derived from" the narbonolide or other naturally occurring PKS includes a modular PKS (or its corresponding encoding gene(s)) that retains the scaffolding of the utilized portion of the naturally occurring gene. Not all modules need be included in the constructs. On the constant scaffold, at least one enzymatic activity is mutated, deleted, replaced, or inserted so as to alter the activity of the resulting PKS relative to the original PKS. Alteration results when these activities are deleted or are replaced by a different version of the activity, or simply mutated in such a way that a polyketide other than the natural product results from these collective activities. This occurs because there has been a resulting alteration of the starter unit and/or extender unit, and/or stereochemistry, and/or chain length or cyclization, and/or reductive or dehydration cycle outcome at a corresponding position in the product polyketide. Where a deleted activity is replaced, the origin of the replacement activity may come from a corresponding activity in a different naturally occurring PKS or from a different region of the narbonolide PKS. Any or all of the narbonolide PKS genes may be included in the derivative or portions of any of these may be included, but the scaffolding of the PKS protein is retained in whatever derivative is constructed. The derivative preferably contains a thioesterase activity from the narbonolide or another PKS.

In summary, a PKS derived from the narbonolide PKS includes a PKS that contains the scaffolding of all or a portion of the narbonolide PKS. The derived PKS also contains at least two extender modules that are functional, preferably three extender modules, and more preferably four or more extender modules, and most preferably six extender modules. The derived PKS also contains mutations, deletions, insertions, or replacements of one or more of the activities of the functional modules of the narbonolide PKS so that the nature of the resulting polyketide is altered. This definition applies both at the protein and DNA sequence levels. Particular preferred embodiments include those wherein a KS, AT, KR, DH, or ER has been deleted or replaced by a version of the activity from a different PKS or from another location within the same PKS. Also preferred are derivatives where at least one non-condensation cycle enzymatic activity (KR, DH, or ER) has been deleted or added or wherein any of these activities has been mutated so as to change the structure of the polyketide synthesized by the PKS.

Conversely, also included within the definition of a PKS derived from the narbonolide PKS are functional PKS modules or their encoding genes wherein at least one portion, preferably two portions, of the narbonolide PKS activities have been inserted. Exemplary is the use of the narbonolide AT for extender module 2 which accepts a malonyl CoA extender unit rather than methylmalonyl CoA to replace a methylmalonyl specific AT in a PKS. Other examples include insertion of portions of non-condensation cycle enzymatic activities or other regions of narbonolide synthase activity into a heterologous PKS. Again, the derived from definition applies to the PKS at both the genetic and protein levels.

Thus, there are at least five degrees of freedom for constructing a hybrid PKS in terms of the polyketide that will be produced. First, the polyketide chain length is determined by the number of modules in the PKS. Second, the nature of the carbon skeleton of the PKS is determined by the specificities of the acyl transferases that determine the nature of the extender units at each position, e.g., malonyl, methylmalonyl, ethylmalonyl, or other substituted malonyl. Third, the loading module specificity also has an effect on the resulting carbon skeleton of the polyketide. The loading module may use a different starter unit, such as acetyl, butyryl, and the like. As noted above and in the examples below, another method for varying loading module specificity involves inactivating the KS activity in extender module 1 (KS1) and providing alternative substrates, called diketides that are chemically synthesized analogs of extender module 1 diketide products, for extender module 2. This approach was illustrated in PCT publication Nos. 97/02358 and 99/03986, incorporated herein by reference, wherein the KS1 activity was inactivated through mutation. Fourth, the oxidation state at various positions of the polyketide will be determined by the dehydratase and reductase portions of the modules. This will determine the presence and location of ketone and alcohol moieties and C—C double bonds or C—C single bonds in the polyketide. Finally, the stereochemistry of the resulting polyketide is a function of three aspects of the synthase. The first aspect is related to the AT/KS specificity associated with substituted malonyls as extender units, which affects stereochemistry only when the reductive cycle is missing or when it contains only a ketoreductase, as the dehydratase would abolish chirality. Second, the specificity of the ketoreductase may determine the chirality of any beta-OH. Finally, the enoylreductase specificity for substituted malonyls as extender units may influence the result when there is a complete KR/DH/ER available.

Thus, the modular PKS systems, and in particular, the narbonolide PKS system, permit a wide range of polyketides to be synthesized. As compared to the aromatic PKS systems, a wider range of starter units including aliphatic monomers (acetyl, propionyl, butyryl, isovaleryl, etc.), aromatics (aminohydroxybenzoyl), alicyclics (cyclohexanoyl), and heterocyclics (thiazolyl) are found in various macrocyclic polyketides. Recent studies have shown that modular PKSs have relaxed specificity for their starter units (Kao et al., 1994, *Science*, supra). Modular PKSs also exhibit considerable variety with regard to the choice of extender units in each condensation cycle. The degree of beta-ketoreduction following a condensation reaction has also been shown to be altered by genetic manipulation (Donadio et al., 1991, *Science*, supra; Donadio et al., 1993, *Proc. Natl. Acad. Sci. USA* 90: 7119–7123). Likewise, the size of the polyketide product can be varied by designing mutants with the appropriate number of modules (Kao et al., 1994, *J. Am. Chem. Soc.* 116:11612–11613). Lastly, these enzymes are particularly well known for generating an impressive range of asymmetric centers in their products in a highly controlled manner. The polyketides and antibiotics produced by the methods of the invention are typically single stereoisomeric forms. Although the compounds of the invention can occur as mixtures of stereoisomers, it may be beneficial in some instances to generate individual stereoisomers. Thus, the combinatorial potential within modular PKS pathways based on any naturally occurring modular, such as the narbonolide, PKS scaffold is virtually unlimited.

The combinatorial potential is increased even further when one considers that mutations in DNA encoding a polypeptide can be used to introduce, alter, or delete an activity in the encoded polypeptide. Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. See, e.g., Kunkel, 1985, *Proc. Natl. Acad. Sci. USA* 82: 448; Geisselsoder et al., 1987, *BioTechniques* 5:786. Alternatively, the mutations can be effected using a mismatched primer (generally 10–20 nucleotides in length) that hybridizes to the native nucleotide sequence, at a temperature below the melting temperature of the mismatched duplex. The primer can be made specific by keeping primer length and base composition within relatively narrow limits and by keeping the mutant base centrally located. See Zoller and Smith, 1983, *Methods Enzymol.* 100:468. Primer extension is effected using DNA polymerase, the product cloned, and clones containing the mutated DNA, derived by segregation of the primer extended strand, selected. Identification can be accomplished using the mutant primer as a hybridization probe. The technique is also applicable for generating multiple point mutations. See, e.g., Dalbie-McFarland et al., 1982, *Proc. Natl. Acad. Sci. USA* 79: 6409. PCR mutagenesis can also be used to effect the desired mutations.

Random mutagenesis of selected portions of the nucleotide sequences encoding enzymatic activities can also be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants, or by damaging plasmid DNA in vitro with chemicals. Chemical mutagens include, for example, sodium bisulfite, nitrous acid, nitrosoguanidine, hydroxylamine, agents which damage or remove bases thereby preventing normal base-pairing such as hydrazine or formic acid, analogues of nucleotide precursors such as 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

In constructing a hybrid PKS of the invention, regions encoding enzymatic activity, i.e., regions encoding corresponding activities from different PKS synthases or from different locations in the same PKS, can be recovered, for example, using PCR techniques with appropriate primers. By "corresponding" activity encoding regions is meant those regions encoding the same general type of activity. For example, a KR activity encoded at one location of a gene cluster "corresponds" to a KR encoding activity in another location in the gene cluster or in a different gene cluster. Similarly, a complete reductase cycle could be considered corresponding. For example, KR/DH/ER corresponds to KR alone.

If replacement of a particular target region in a host PKS is to be made, this replacement can be conducted in vitro using suitable restriction enzymes. The replacement can also be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT publication No. WO 96/40968, incorporated herein by reference. The vectors used to perform the various operations to replace the enzymatic activity in the host PKS genes or to support mutations in these regions of the host PKS genes can be chosen to contain control sequences operably linked to the resulting coding sequences in a manner such that expression of the coding sequences can be effected in an appropriate host.

However, simple cloning vectors may be used as well. If the cloning vectors employed to obtain PKS genes encoding derived PKS lack control sequences for expression operably linked to the encoding nucleotide sequences, the nucleotide sequences are inserted into appropriate expression vectors. This need not be done individually, but a pool of isolated encoding nucleotide sequences can be inserted into expression vectors, the resulting vectors transformed or transfected into host cells, and the resulting cells plated out into individual colonies.

The various PKS nucleotide sequences can be cloned into one or more recombinant vectors as individual cassettes, with separate control elements, or under the control of, e.g., a single promoter. The PKS subunit encoding regions can include flanking restriction sites to allow for the easy deletion and insertion of other PKS subunit encoding sequences so that hybrid PKSs can be generated. The design of such unique restriction sites is known to those of skill in the art and can be accomplished using the techniques described above, such as site-directed mutagenesis and PCR.

The expression vectors containing nucleotide sequences encoding a variety of PKS enzymes for the production of different polyketides are then transformed into the appropriate host cells to construct the library. In one straightforward approach, a mixture of such vectors is transformed into the selected host cells and the resulting cells plated into individual colonies and selected to identify successful transformants. Each individual colony has the ability to produce a particular PKS synthase and ultimately a particular polyketide. Typically, there will be duplications in some, most, or all of the colonies; the subset of the transformed colonies that contains a different PKS in each member colony can be considered the library. Alternatively, the expression vectors can be used individually to transform hosts, which transformed hosts are then assembled into a library. A variety of strategies are available to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, and more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length is quite large.

Methods for introducing the recombinant vectors of the invention into suitable hosts are known to those of skill in the art and typically include the use of $CaCl_2$ or agents such as other divalent cations, lipofection, DMSO, protoplast transformation, infection, transfection, and electroporation. The polyketide producing colonies can be identified and isolated using known techniques and the produced polyketides further characterized. The polyketides produced by these colonies can be used collectively in a panel to represent a library or may be assessed individually for activity.

The libraries of the invention can thus be considered at four levels: (1) a multiplicity of colonies each with a different PKS encoding sequence; (2) colonies that contain the proteins that are members of the PKS library produced by the coding sequences; (3) the polyketides produced; and (4) antibiotics or compounds with other desired activities derived from the polyketides. Of course, combination libraries can also be constructed wherein members of a library derived, for example, from the narbonolide PKS can be considered as a part of the same library as those derived from, for example, the rapamycin PKS or DEBS.

Colonies in the library are induced to produce the relevant synthases and thus to produce the relevant polyketides to obtain a library of polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can more readily be included. Antibiotic activity can be verified using typical screening assays such as those set forth in Lehrer et al., 1991, *J. Immunol. Meth.* 137:167–173, incorporated herein by reference, and in the examples below.

The invention provides methods for the preparation of a large number of polyketides. These polyketides are useful intermediates in formation of compounds with antibiotic or other activity through hydroxylation and glycosylation reactions as described above. In general, the polyketide products of the PKS must be further modified, typically by hydroxylation and glycosylation, to exhibit antibiotic activity. Hydroxylation results in the novel polyketides of the invention that contain hydroxyl groups at C6, which can be accomplished using the hydroxylase encoded by the eryF gene, and/or C12, which can be accomplished using the hydroxylase encoded by the picK or eryK gene. The presence of hydroxyl groups at these positions can enhance the antibiotic activity of the resulting compound relative to its unhydroxylated counterpart.

Gycosylation is important in conferring antibiotic activity to a polyketide as well. Methods for glycosylating the polyketides are generally known in the art; the glycosylation may be effected intracellularly by providing the appropriate glycosylation enzymes or may be effected in vitro using chemical synthetic means as described herein and in PCT publication No. WO 98/49315, incorporated herein by reference. Preferably, glycosylation with desosamine is effected in accordance with the methods of the invention in recombinant host cells provided by the invention. In general, the approaches to effecting glycosylation mirror those described above with respect to hydroxylation. The purified enzymes, isolated from native sources or recombinantly produced may be used in vitro. Alternatively and as noted, glycosylation may be effected intracellularly using endogenous or recombinantly produced intracellular glycosylases. In addition, synthetic chemical methods may be employed.

The antibiotic modular polyketides may contain any of a number of different sugars, although D-desosamine, or a close analog thereof, is most common. Erythromycin, picromycin, narbomycin and methymycin contain desosamine. Erythromycin also contains L-cladinose (3-O-methyl mycarose). Tylosin contains mycaminose (4-hydroxy desosamine), mycarose and 6-deoxy-D-allose. 2-acetyl-1-bromodesosamine has been used as a donor to glycosylate polyketides by Masamune et al., 1975, *J. Am. Chem. Soc.* 97: 3512–3513. Other, apparently more stable donors include glycosyl fluorides, thioglycosides, and trichloroacetimidates; see Woodward et al., 1981, *J. Am. Chem. Soc.* 103: 3215; Martin et al., 1997, *J. Am. Chem. Soc.* 119: 3193; Toshima et al., 1995, *J. Am. Chem. Soc.* 117: 3717; Matsumoto et al., 1988, *Tetrahedron Lett.* 29: 3575. Glycosylation can also be effected using the polyketide aglycones as starting materials and using *Saccharopolyspora erythraea* or *Streptomyces venezuelae* to make the conversion, preferably using mutants unable to synthesize macrolides.

To provide an illustrative hybrid PKS of the invention as well as an expression vector for that hybrid PKS and host cells comprising the vector and producing the hybrid polyketide, a portion of the narbonolide PKS gene was fused to the DEBS genes. This construct also allowed the examination of whether the TE domain of the narbonolide PKS (pikTE) could promote formation of 12-membered lactones in the context of a different PKS. A construct was generated, plasmid pKOS039-18, in which the pikTE ORF was fused with the DEBS genes in place of the DEBS TE ORF (see FIG. 5). To allow the TE to distinguish between substrates most closely resembling those generated by the narbonolide PKS, the fusion junction was chosen between the AT and ACP to eliminate ketoreductase activity in DEBS extender module 6 (KR6). This results in a hybrid PKS that presents the TE with a β-ketone heptaketide intermediate and a β-(S)-hydroxy hexaketide intermediate to cyclize, as in narbonolide and 10-deoxymethynolide biosynthesis.

Figure 5:
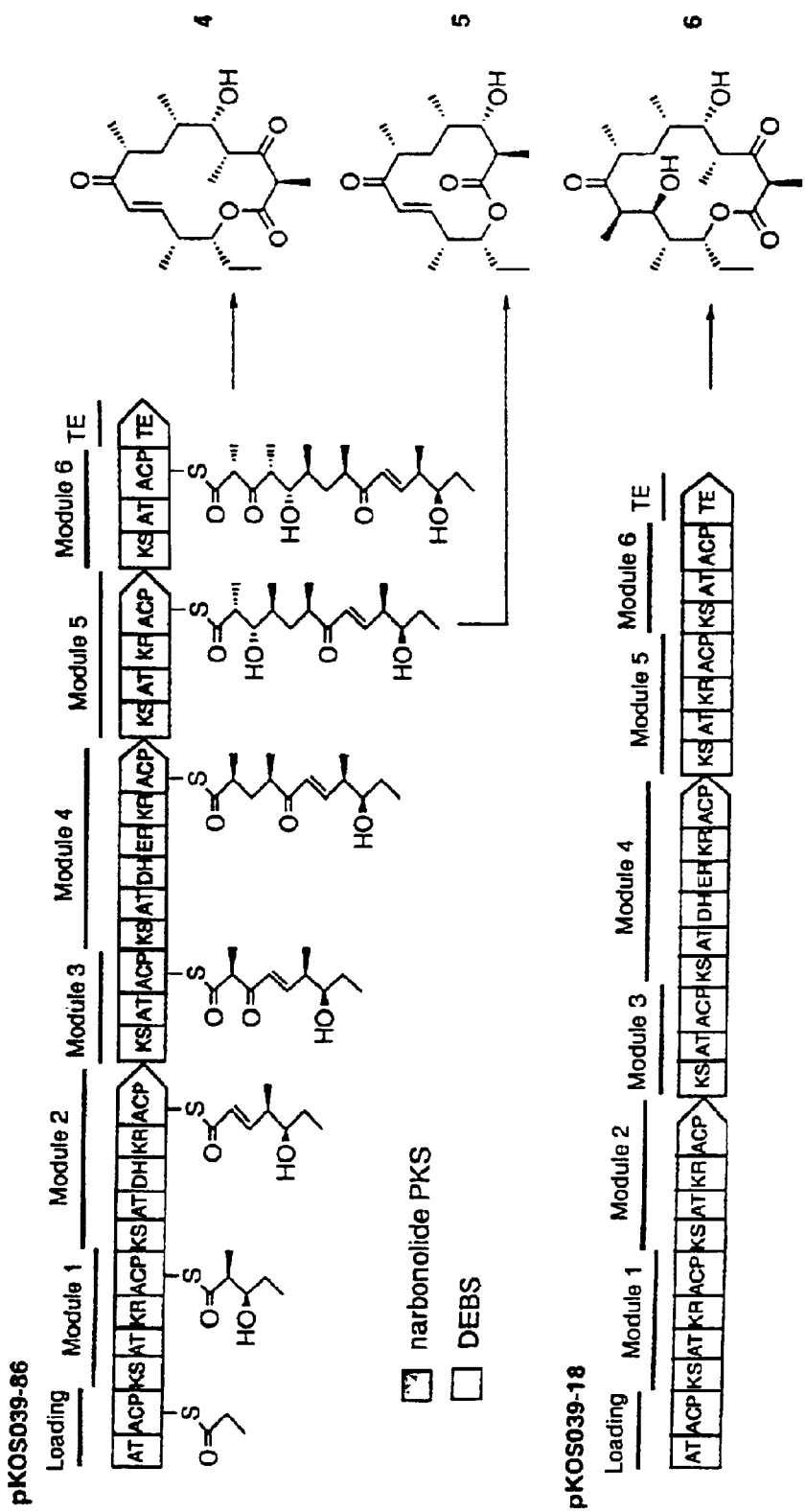
FIG. 5 shows the narbonolide PKS genes encoded by plasmid pKOS039-86, the compounds synthesized by each module of that PKS and the narbonolide (compound 4) and 10-deoxymethynolide (compound 5) products produced in heterologous host cells transformed with the plasmid. The Figure also shows a hybrid PKS of the invention produced by plasmid pKOS038-18, which encodes a hybrid of DEBS and the narbonolide PKS. The Figure also shows the compound, 3,6-dideoxy-3-oxo-erythronolide B (compound 6), produced in heterologous host cells comprising the plasmid.

Analysis of this construct indicated the production of the 14-membered ketolide 3,6-dideoxy-3-oxo-erythronolide B (FIG. 5, compound 6). Extracts were analyzed by LC/MS. The identity of compound 6 was verified by comparison to a previously authenticated sample (see PCT publication No. 98/49315, incorporated herein by reference). The predicted 12-membered macrolactone, (8R,9S)-8,9-dihydro-8-methyl-9-hydroxy-10-deoxymethynolide (see Kao et al., 1995, *J. Am. Chem. Soc.* 117, incorporated herein by reference) was not detected. This result, along with others reported herein, suggests that protein interactions between the narbonolide PKS modules play a role in formation of the 12 and 14-membered macrolides.

The above example illustrates also how engineered PKSs can be improved for production of novel compounds. Compound 6 was originally produced by deletion of the KR6 domain in DEBS to create a 3-ketolide producing PKS (see U.S. patent application Ser. No. 09/073,538, filed May 6, 1998, and PCT publication No. WO 98/49315, each of which is incorporated herein by reference). Although the desired molecule was made, purification of compound 6 from this strain was hampered by the presence of 2-desmethyl ketolides that could not be easily separated. Extracts from *Streptomyces lividans* K4-114/pKOS039-18, however, do not contain the 2-desmethyl compounds, greatly simplifying purification. Thus, the invention provides a useful method of producing such compounds. The ability to combine the narbonolide PKS with DEBS and other modular PKSs provides a significant advantage in the production of macrolide antibiotics.

Two other hybrid PKSs of the invention were constructed that yield this same compound. These constructs also illustrate the method of the invention in which hybrid PKSs are constructed at the protein, as opposed to the module, level. Thus, the invention provides a method for constructing a hybrid PKS which comprises the coexpression of at least one gene from a first modular PKS gene cluster in a host cell that also expresses at least one gene from a second PKS gene cluster. The invention also provides novel hybrid PKS enzymes prepared in accordance with the method. This method is not limited to hybrid PKS enzymes composed of at least one narbonolide PKS gene, although such constructs are illustrative and preferred. Moreover, the hybrid PKS enzymes are not limited to hybrids composed of unmodified proteins; as illustrated below, at least one of the genes can optionally be a hybrid PKS gene.

In the first construct, the eryAI and eryAII genes were coexpressed with picAIV and a gene encoding a hybrid extender module 5 composed of the KS and AT domains of extender module 5 of DEBS3 and the KR and ACP domains of extender module 5 of the narbonolide PKS. In the second construct, the picAIV coding sequence was fused to the hybrid extender module 5 coding sequence used in the first construct to yield a single protein. Each of these constructs produced 3-deoxy-3-oxo-6-deoxyerythronolide B. In a third construct, the coding sequence for extender module 5 of DEBS3 was fused to the picAIV coding sequence, but the levels of product produced were below the detection limits of the assay.

A variant of the first construct hybrid PKS was constructed that contained an inactivated DEBS1 extender module 1 KS domain. When host cells containing the resultant hybrid PKS were supplied the appropriate diketide precursor, the desired 13-desethyl-13-propyl compounds were obtained, as described in the examples below.

Other illustrative hybrid PKSs of the invention were made by coexpressing the picAI and picAII genes with genes encoding DEBS3 or DEBS3 variants. These constructs illustrate the method of the invention in which a hybrid PKS is produced from coexpression of PKS genes unmodified at the modular or domain level. In the first construct, the eryAIII gene was coexpressed with the picAI and picAII genes, and the hybrid PKS produced 10-desmethyl-10,11-anhydro-6-deoxyerythronolide B in *Streptomyces lividans*. Such a hybrid PKS could also be constructed in accordance with the method of the invention by transformation of *S. venzuelae* with an expression vector that produces the eryAIII gene product, DEBS3. In a preferred embodiment, the *S. venezuelae* host cell has been modified to inactivate the picAIII gene.

In the second construct, the DEBS3 gene was a variant that had an inactive KR in extender module 5. The hybrid PKS produced 5,6-dideoxy-5-oxo-10-desmethyl-10,11-anhydroerythronolide B in *Streptomyces lividans*.

In the third construct, the DEBS3 gene was a variant in which the KR domain of extender module 5 was replaced by the DH and KR domains of extender module 4 of the rapamycin PKS. This construct produced 5,6-dideoxy-5-oxo-10-desmethyl-10,11-anhydroerythronolide B and 5,6-dideoxy-4,5-anhydro-10-desmethyl-10,11-anhydroerythronolide B in *Streptomyces lividans*, indicating that the rapamycin DH and KR domains functioned only inefficiently in this construct.

In the fourth construct, the DEBS3 gene was a variant in which the KR domain of extender module 5 was replaced by the DH, KR, and ER domains of extender module 1 of the rapamycin PKS. This construct produced 5,6-dideoxy-5-oxo-10-desmethyl-10,11-anhydroerythronolide B as well as 5,6-dideoxy-10-desmethyl-10,11-anhydroerythronolide B in *Streptomyces lividans*, indicating that the rapamycin DH, KR, and ER domains functioned only inefficiently in this construct.

In the fifth construct, the DEBS3 gene was a variant in which the KR domain of extender module 6 was replaced by the DH and KR domains of extender module 4 of the rapamycin PKS. This construct produced 3,6-dideoxy-2,3-anhydro-10-desmethyl-10,11-anhydroerythronolide B in *Streptomyces lividans*.

In the sixth construct, the DEBS3 gene was a variant in which the AT domain of extender module 6 was replaced by the AT domain of extender module 2 of the rapamycin PKS. This construct produced 2,10-didesmethyl-10,11-anhydro-6-deoxyerythronolide B in *Streptomyces lividans*.

These hybrid PKSs illustrate the wide variety of polyketides that can be produced by the methods and compounds of the invention. These polyketides are useful as antibiotics and as intermediates in the synthesis of other useful compounds, as described in the following section.

Section VI: Compounds

The methods and recombinant DNA compounds of the invention are useful in the production of polyketides. In one important aspect, the invention provides methods for making ketolides, polyketide compounds with significant antibiotic activity. See Griesgraber et al., 1996, *J. Antibiot.* 49: 465–477, incorporated herein by reference. Most if not all of the ketolides prepared to date are synthesized using erythromycin A, a derivative of 6-dEB, as an intermediate. While the invention provides hybrid PKSs that produce a polyketide different in structure from 6-dEB, the invention also provides methods for making intermediates useful in preparing traditional, 6-dEB-derived ketolide compounds.

Because 6-dEB in part differs from narbonolide in that it comprises a 10-methyl group, the novel hybrid PKS genes of the invention based on the narbonolide PKS provide many novel ketolides that differ from the known ketolides only in that they lack a 10-methyl group. Thus, the invention provides the 10-desmethyl analogues of the ketolides and intermediates and precursor compounds described in, for example, Griesgraber et al., supra; Agouridas et al., 1998, *J. Med. Chem.* 41: 4080–4100, U.S. Pat. Nos. 5,770,579; 5,760,233; 5,750,510; 5,747,467; 5,747,466; 5,656,607; 5,635,485; 5,614,614; 5,556,118; 5,543,400; 5,527,780; 5,444,051; 5,439,890; 5,439,889; and PCT publication Nos. WO 98/09978 and 98/28316, each of which is incorporated herein by reference. Because the invention also provides hybrid PKS genes that include a methylmalonyl-specific AT domain in extender module 2 of the narbonolide PKS, the invention also provides hybrid PKS that can be used to produce the 10-methyl-containing ketolides known in the art.

Thus, a hybrid PKS of the invention that produces 10-methyl narbonolide is constructed by substituting the malonyl-specific AT domain of the narbonolide PKS extender module 2 with a methylmalonyl specific AT domain from a heterologous PKS. A hybrid narbonolide PKS in which the AT of extender module 2 was replaced with the AT from DEBS extender module 2 was constructed using boundaries described in PCT publication No. 98/49315, incorporated herein by reference. However, when the hybrid PKS expression vector was introduced into *Streptomyces venezuelae*, detectable quantities of 10-methyl picromycin were not produced. Thus, to construct such a hybrid PKS of the invention, an AT domain from a module other than DEBS extender module 2 is preferred. One could also employ DEBS extender module 2 or another methylmalonyl specific AT but utilize instead different boundaries than those used for the substitution described above. In addition, one can construct such a hybrid PKS by substituting, in addition to the AT domain, additional extender module 2 domains, including the KS, the KR, and the DH, and/or additional extender module 3 domains.

Although modification of extender module 2 of the narbonolide PKS is required, the extent of hybrid modules engineered need not be limited to module 2 to make 10-methyl narbonolide. For example, substitution of the KS domain of extender module 3 of the narbonolide PKS with a heterologous domain or module can result in more efficient processing of the intermediate generated by the hybrid extender module 2. Likewise, a heterologous TE domain may be more efficient in cyclizing 10-methyl narbonolide.

Substitution of the entire extender module 2 of the narbonolide PKS with a module encoding the correct enzymatic activities, i.e., a KS, a methylmalonyl specific AT, a KR, a DH, and an ACP, can also be used to create a hybrid PKS of the invention that produces a 10-methyl ketolide. Modules useful for such whole module replacements include extender modules 4 and 10 from the rapamycin PKS, extender modules 1 and 5 from the FK506 PKS, extender module 2 of the tylosin PKS, and extender module 4 of the rifamycin PKS. Thus, the invention provides many different hybrid PKSs that can be constructed starting from the narbonolide PKS that can be used to produce 10-methyl narbonolide. While 10-methyl narbonolide is referred to in describing these hybrid PKSs, those of skill recognize that the invention also therefore provides the corresponding derivatives produces by glycosylation and hydroxylation. For example, if the hybrid PKS is expressed in *Streptomyces narbonensis* or *S. venezuelae*, the compounds produced are 10-methyl narbomycin and picromycin, respectively. Alternatively, the PKS can be expressed in a host cell transformed with the vectors of the invention that encode the desosamine biosynthesis and desosaminyl transferase and picK hydroxylase genes.

Other important compounds provided by the invention are the 6-hydroxy ketolides. These compounds include 3-deoxy-3-oxo erythronolide B, 6-hydroxy narbonolide, and 6-hydroxy-10-methyl narbonolide. In the examples below, the invention provides a method for utilizing EryF to hydroxylate 3-ketolides that is applicable for the production of any 6-hydroxy-3-ketolide.

Thus, the hybrid PKS genes of the invention can be expressed in a host cell that contains the desosamine biosynthetic genes and desosaminyl transferase gene as well as the required hydroxylase gene(s), which may be either picK (for the C12 position) or eryK (for the C12 position) and/or eryF (for the C6 position). The resulting compounds have antibiotic activity but can be further modified, as described in the patent publications referenced above, to yield a desired compound with improved or otherwise desired properties. Alternatively, the aglycone compounds can be produced in the recombinant host cell, and the desired glycosylation and hydroxylation steps carried out in vitro or in vivo, in the latter case by supplying the converting cell with the aglycone.

The compounds of the invention are thus optionally glycosylated forms of the polyketide set forth in formula (2) below which are hydroxylated at either the C6 or the C12 or both. The compounds of formula (2) can be prepared using the loading and the six extender modules of a modular PKS, modified or prepared in hybrid form as herein described. These polyketides have the formula:

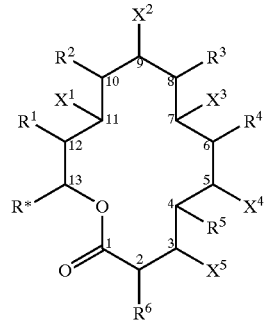

(2)

including the glycosylated and isolated stereoisomeric forms thereof;

wherein R* is a straight chain, branched or cyclic, saturated or unsaturated substituted or unsubstituted hydrocarbyl of 1–15C;

each of $R^1$–$R^6$ is independently H or alkyl (1–4C) wherein any alkyl at $R^1$ may optionally be substituted;

each of $X^1$–$X^5$ is independently two H, H and OH, or =O; or each of $X^1$–$X^5$ is independently H and the compound of formula (2) contains a double-bond in the ring adjacent to the position of said X at 2–3, 4–5, 6–7, 8–9 and/or 10–11;

with the proviso that:

at least two of $R^1$–$R^6$ are alkyl (1–4C).

Preferred compounds comprising formula 2 are those wherein at least three of $R^1$–$R^5$ are alkyl (1–4C), preferably methyl or ethyl; more preferably wherein at least four of $R^1$–$R^5$ are alkyl (1–4C), preferably methyl or ethyl. Also preferred are those wherein $X^2$ is two H, =O, or H and OH, and/or $X^3$ is H, and/or $X^1$ is OH and/or $X^4$ is OH and/or $X^5$ is OH. Also preferred are compounds with variable R* when $R^1$–$R^5$ is methyl, $X^2$ is =O, and $X^1$, $X^4$ and $X^5$ are OH. The glycosylated forms of the foregoing are also preferred.

The invention also provides the 12-membered macrolides corresponding to the compounds above but produced from a narbonolide-derived PKS lacking extender modules 5 and 6 of the narbonolide PKS.

The compounds of the invention can be produced by growing and fermenting the host cells of the invention under conditions known in the art for the production of other polyketides. The compounds of the invention can be isolated from the fermentation broths of these cultured cells and purified by standard procedures. The compounds can be readily formulated to provide the pharmaceutical compositions of the invention. The pharmaceutical compositions of the invention can be used in the form of a pharmaceutical preparation, for example, in solid, semisolid, or liquid form. This preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, solutions, emulsions, suspensions, and any other form suitable for use.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquefied form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, Transplantation Proceedings XIX, Supp. 6: 17–22, incorporated herein by reference. Dosage forms for external application may be prepared essentially as described in EPO patent publication No. 423,714, incorporated herein by reference. The active compound is included in the pharmaceutical composition in an amount sufficient to produce the desired effect upon the disease process or condition.

For the treatment of conditions and diseases caused by infection, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intramuscular, and intrasternal injection or infusion techniques.

Dosage levels of the compounds of the invention are of the order from about 0.01 mg to about 50 mg per kilogram of body weight per day, preferably from about 0.1 mg to about 10 mg per kilogram of body weight per day. The dosage levels are useful in the treatment of the above-indicated conditions (from about 0.7 mg to about 3.5 mg per patient per day, assuming a 70 kg patient). In addition, the compounds of the invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 gm of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention may be formulated within the range of, for example, 0.00001% to 60% by weight, preferably from 0.001% to 10% by weight, and most preferably from about 0.005% to 0.8% by weight.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

A detailed description of the invention having been provided above, the following examples are given for the purpose of illustrating the invention and shall not be construed as being a limitation on the scope of the invention or claims.

EXAMPLE 1

General Methodology

Bacterial strains, plasmids, and culture conditions. *Streptomyces coelicolor* CH999 described in WO 95/08548, published 30Mar. 1995, or *S. Lividans* K4-114, described in Ziermann and Betlach, January 99, Recombinant Polyketide Synthesis in *Streptomyces*: Engineering of Improved Host Strains, BioTechniques 26:106–110, incorporated herein by reference, was used as an expression host. DNA manipulations were performed in *Escherichia coli* XL1-Blue, available from Stratagene. *E. coli* MC1061 is also suitable for use as a host for plasmid manipulation. Plasmids were passaged through *E. coli* ET12567 (dam dcm hsdS Cm$^r$) (MacNeil, 1988, *J. Bacteriol.* 170: 5607, incorporated herein by reference) to generate unmethylated DNA prior to transformation of *S. coelicolor*. *E. coli* strains were grown under standard conditions. *S. coelicolor* strains were grown on R2YE agar plates (Hopwood et al., *Genetic manipulation of Streptomyces. A laboratory manual*. The John Innes Foundation: Norwich, 1985, incorporated herein by reference).

Many of the expression vectors of the invention illustrated in the examples are derived from plasmid pRM5, described in WO 95/08548, incorporated herein by reference. This plasmid includes a colEI replicon, an appropriately truncated SCP2* *Streptomyces* replicon, two act-promoters to allow for bidirectional cloning, the gene encoding the actII-ORF4 activator which induces transcription from act promoters during the transition from growth phase to stationary phase, and appropriate marker genes. Engineered restriction sites in the plasmid facilitate the combinatorial construction of PKS gene clusters starting from cassettes encoding individual domains of naturally occurring PKSs. When plasmid pRM5 is used for expression of a PKS, all relevant biosynthetic genes can be plasmid-borne and therefore amenable to facile manipulation and mutagenesis in *E. coli*. This plasmid is also suitable for use in *Streptomyces* host cells. *Streptomyces* is genetically and physiologically well-characterized and expresses the ancillary activities required for in vivo production of most polyketides. Plasmid pRM5 utilizes the act promoter for PKS gene expression, so polyketides are produced in a secondary metabolite-like manner, thereby alleviating the toxic effects of synthesizing potentially bioactive compounds in vivo.

Manipulation of DNA and organisms. Polymerase chain reaction (PCR) was performed using Pfu polymerase (Stratagene; Taq polymerase from Perkin Elmer Cetus can also be used) under conditions recommended by the enzyme manufacturer. Standard in vitro techniques were used for DNA manipulations (Sambrook et al. *Molecular Cloning: A Laboratory Manual* (Current Edition)). *E. coli* was transformed using standard calcium chloride-based methods; a Bio-Rad *E. coli* pulsing apparatus and protocols provided by Bio-Rad could also be used. *S. coelicolor* was transformed by standard procedures (Hopwood et al. *Genetic manipulation of Streptomyces. A laboratory manual*. The John Innes Foundation: Norwich, 1985), and depending on what selectable marker was employed, transformants were selected using 1 mL of a 1.5 mg/mL thiostrepton overlay, 1 mL of a 2 mg/mL apramycin overlay, or both.

EXAMPLE 2

Cloning of the Picromycin Biosynthetic Gene Cluster from *Streptomyces Venezuelae*

Genomic DNA (100 μg) isolated from *Streptomyces venezuelae* ATCC15439 using standard procedures was partially digested with Sau3AI endonuclease to generate fragments ~40 kbp in length. SuperCosI (Stratagene) DNA cosmid arms were prepared as directed by the manufacturer. A cosmid library was prepared by ligating 2.5 μg of the digested genomic DNA with 1.5 μg of cosmid arms in a 20

µL reaction. One microliter of the ligation mixture was propagated in *E. coli* XL1-Blue MR (Stratagene) using a GigapackIII XL packaging extract kit (Stratagene). The resulting library of ~3000 colonies was plated on a 10×150 mm agar plate and replicated to a nylon membrane.

The library was initially screened by direct colony hybridization with a DNA probe specific for ketosynthase domain coding sequences of PKS genes. Colonies were alkaline lysed, and the DNA was crosslinked to the membrane using UV irradiation. After overnight incubation with the probe at 42° C., the membrane was washed twice at 25° C. in 2×SSC buffer+0.1% SDS for 15 minutes, followed by two 15 minute washes with 233 SSC buffer at 55° C. Approximately 30 colonies gave positive hybridization signals with the degenerate probe. Several cosmids were selected and divided into two classes based on restriction digestion patterns. A representative cosmid was selected from each class for further analysis. The representative cosmids were designated pKOS023-26 and pKOS023-27. These cosmids were determined by DNA sequencing to comprise the narbonolide PKS genes, the desosamine biosynthesis and transferase genes, the beta-glucosidase gene, and the picK hydroxylase gene. These cosmids were deposited with the American Type Culture Collection in accordance with the terms of the Budapest Treaty. Cosmid pKOS023-26 was assigned accession number ATCC 203141, and cosmid pKOS023-27 was assigned accession number ATCC 203142.

To demonstrate that the narbonolide PKS genes had been cloned and to illustrate how the invention provides methods and reagents for constructing deletion variants of narbonolide PKS genes, a narbonolide PKS gene was deleted from the chromosome of *Streptomyces venezuelae*. This deletion is shown schematically in FIG. 4, parts B and C. A ~2.4 kb EcoRI-KpnI fragment and a ~2.1 kb KpnI-XhoI fragment, which together comprise both ends of the picAI gene (but lack a large portion of the coding sequence), were isolated from cosmid pKOS023-27 and ligated together into the commercially available vector pLitmus 28 (digested with restriction enzymes EcoRI and XhoI) to give plasmid pKOS039-07. The ~4.5 kb HindIII-SpeI fragment from plasmid pKOS039-07 was ligated with the 2.5 kb HindIII-NHeI fragment of integrating vector pSET152, available from the NRRL, which contains an *E. coli* origin of replication and an apramycin resistance-conferring gene to create plasmid pKOS039-16. This vector was used to transform *S. venezuelae*, and apramycin-resistant transformants were selected.

Then, to select for double-crossover mutants, the selected transformants were grown in TSB liquid medium without antibiotics for three transfers and then plated onto nonselective media to provide single colony isolates. The isolated colonies were tested for sensitivity to apramycin, and the apramycin-sensitive colonies were then tested to determine if they produced picromycin. The tests performed included a bioassay and LC/MS analysis of the fermentation media. Colonies determined not to produce picromycin (or methymycin or neomethymycin) were then analyzed using PCR to detect an amplification product diagnostic of the deletion. A colony designated K39-03 was identified, providing confirmation that the narbonolide PKS genes had been cloned. Transformation of strain K39-03 with plasmid pKOS039-27 comprising an intact picA gene under the control of the ermE* promoter from plasmid pWHM3 (see Vara et al., 1989, *J. Bact.* 171: 5872–5881, incorporated herein by reference) was able to restore picromycin production.

To determine that the cosmids also contained the picK hydroxylase gene, each cosmid was probed by Southern hybridization using a labeled DNA fragment amplified by PCR from the *Saccharopolyspora erythraea* C12-hydroxylase gene, eryK. The cosmids were digested with BamHI endonuclease and electrophoresed on a 1% agarose gel, and the resulting fragments were transferred to a nylon membrane. The membrane was incubated with the eryK probe overnight at 42° C., washed twice at 25° C. in 2×SSC buffer with 0.1% SDS for 15 minutes, followed by two 15 minute washes with 2×SSC buffer at 50° C. Cosmid pKOS023-26 produced an ~3 kb fragment that hybridized with the probe under these conditions. This fragment was subcloned into the PCRscript™ (Stratagene) cloning vector to yield plasmid pKOS023-28 and sequenced. The ~1.2 kb gene designated picK above was thus identified. The picK gene product is homologous to eryK and other known macrolide cytochrome P450 hydroxylases.

By such methodology, the complete set of picromycin biosynthetic genes were isolated and identified. DNA sequencing of the cloned DNA provided further confirmation that the correct genes had been cloned. In addition, and as described in the following example, the identity of the genes was confirmed by expression of narbomycin in heterologous host cells.

EXAMPLE 3

Heterologous Expression of the Narbonolide PKS and the Picromycin Biosynthetic Gene Cluster To provide a preferred host cell and vector for purposes of the invention, the narbonolide PKS was transferred to the non-macrolide producing host *Streptomyces lividans* K4-114 (see Ziermann and Betlach, 1999, Biotechniques 26, 106–110, and U.S. patent application Ser. No. 09/181,833, filed 28 Oct. 1998, each of which is incorporated herein by reference). This was accomplished by replacing the three DEBS ORFs on a modified version of pCK7 (see Kao et al., 1994, *Science* 265, 509–512, and U.S. Pat. No. 5,672,491, each of which is incorporated herein by reference) with all four narbonolide PKS ORFs to generate plasmid pKOS039-86 (see FIG. 5). The pCK7 derivative employed, designated pCK7'Kan', differs from pCK7 only in that it contains a kanamycin resistance conferring gene inserted at its HindIII restriction enzyme recognition site. Because the plasmid contains two selectable markers, one can select for both markers and so minimize contamination with cells containing rearranged, undesired vectors.

Protoplasts were transformed using standard procedures and transformants selected using overlays containing antibiotics. The strains were grown in liquid R5 medium for growth/seed and production cultures at 30° C. Transformed strains produced two compounds in similar yield (~5–10 mg/L each). Polyketides produced in the host cells were analyzed by bioassay against *Bacillus subtilis* and by LC/MS analysis. Analysis of extracts by LC/MS followed by $^1$H-NMR spectroscopy of the purified compounds established their identity as narbonolide (FIG. 5, compound 4; see Kaiho et al., 1982, *J. Org. Chem.* 47: 1612–1614, incorporated herein by reference) and 10-deoxymethynolide (FIG. 5, compound 5; see Lambalot et al., 1992, *J. Antibiotics* 45, 1981–1982, incorporated herein by reference), the respective 14 and 12-membered polyketide aglycones of YC17, narbomycin, picromycin, and methymycin.

The production of narbonolide in *Streptomyces lividans* represents the expression of an entire modular polyketide pathway in a heterologous host. The combined yields of compounds 4 and 5 are similar to those obtained with expression of DEBS from pCK7 (see Kao et al., 1994, Science 265: 509–512, incorporated herein by reference). Furthermore, based on the relative ratios (~1:1) of compounds 4 and 5 produced, it is apparent that the narbonolide PKS itself possesses an inherent ability to produce both 12 and 14-membered macrolactones without the requirement of additional activities unique to S. venezuelae. Although the existence of a complementary enzyme present in S. lividans that provides this function is possible, it would be unusual to find such a specific enzyme in an organism that does not produce any known macrolide.

To provide a heterologous host cell of the invention that produces the narbonolide PKS and the picB gene, the picB gene was integrated into the chromosome of Streptomyces lividans harboring plasmid pKOS039-86 to yield S. lividans K39-18/pKOS039-86. To provide the integrating vector utilized, the picB gene was cloned into the Streptomyces genome integrating vector pSET152 (see Bierman et al., 1992, Gene 116,43, incorporated herein by reference) under control of the same promoter (PactI) as the PKS on plasmid pKOS039-86.

A comparison of strains K39-18/pKOS039-86 and K4-114/pKOS039-86 grown under identical conditions indicated that the strain containing TEII produced 4–7 times more total polyketide. Each strain was grown in 30 mL of R5 (see Hopwood et al., Genetic Manipulation of Streptomyces: A Laboratory Manual; John Innes Foundation: Norwich, UK, 1985, incorporated herein by reference) liquid (with 20 µg/mL thiostrepton) at 30° C. for 9 days. The fermentation broth was analyzed directly by reverse phase HPLC. Absorbance at 235 nm was used to monitor compounds and measure relative abundance. This increased production indicates that the enzyme is functional in this strain. As noted above, because the production levels of compound 4 and 5 from K39-18/pKOS03986 increased by the same relative amounts, TEII does not appear to influence the ratio of 12 and 14-membered lactone ring formation.

To express the glycosylated counterparts of narbonolide (narbomycin) and 10-deoxymethynolide (YC17) in heterologous host cells, the desosamine biosynthetic genes and desosaminyl transferase gene were transformed into the host cells harboring plasmid pKOS039-86(and, optionally, the picB gene, which can be integrated into the chromosome as described above).

Figure 6:
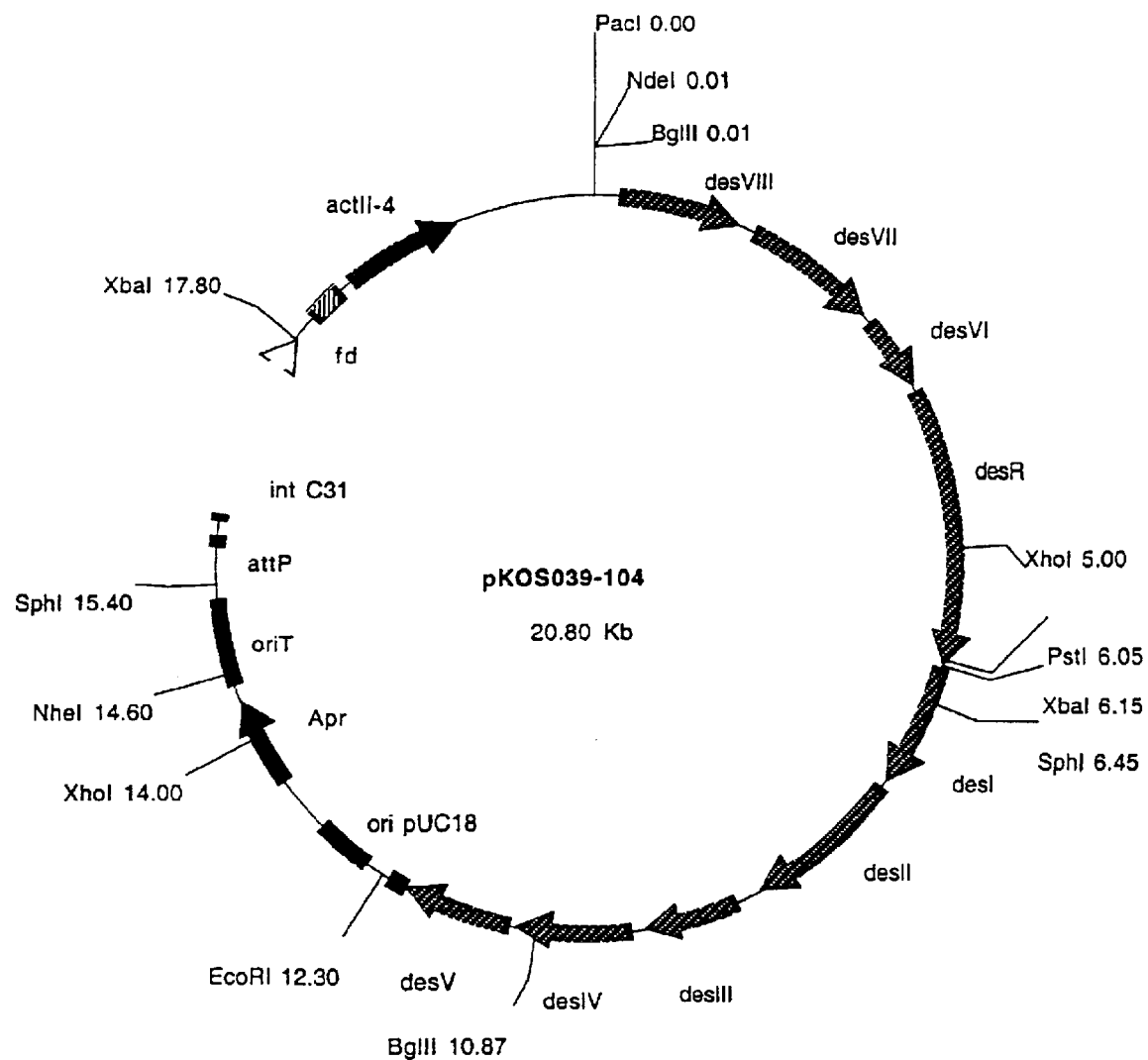
FIG. 6 shows a restriction site and function map of plasmid pKOS039-104, which contains the desosamine biosynthetic, beta-glucosidase, and desosaminyl transferase genes under transcriptional control of actI1–4.

Plasmid pKOS039-104, see FIG. 6, comprises the desosamine biosynthetic genes, the beta-glucosidase gene, and the desosaminyl transferase gene. This plasmid was constructed by first inserting a polylinker oligonucleotide, containing a restriction enzyme recognition site for PacI, a Shine-Dalgarno sequence, and restriction enzyme recognition sites for NdeI, BglII, and HindIII, into a pUC19 derivative, called pKOS24-47, to yield plasmid pKOS039-98.

An ~0.3 kb PCR fragment comprising the coding sequence for the N-terminus of the desI gene product and an ~0.12 kb PCR fragment comprising the coding sequence for the C-terminus of the desR gene product were amplified from cosmid pKOS23-26 (ATCC 203141) and inserted together into pLitmus28 treated with restriction enzymes NsiI and EcoRI to produce plasmid pKOS039-101. The ~6 kb SphI-PstI restriction fragment of pKOS23-26 containing the desI, desII, desIII, desIV, and desV genes was inserted into plasmid pUC19 (Stratagene) to yield plasmid pKOS039-102. The ~6 kb SphI-EcoRI restriction fragment from plasmid pKOS039-102 was inserted into pKOS039-101 to produce plasmid pKOS039-103. The ~6 kb BglII-PstI fragment from pKOS23-26 that contains the desR, des VI, des VII, and desVIII genes was inserted into pKOS39-98 to yield pKOS39-100. The ~6 kb PacI-PstI restriction fragment of pKOS39-100 and the ~6.4 kb NsiI-EcoRI fragment of pKOS39-103 were cloned into pKOS39-44 to yield pKOS39-104.

When introduced into Streptomyces lividans host cells comprising the recombinant narbonolide PKS of the invention, plasmid pKOS39-104 drives expression of the desosamine biosynthetic genes, the beta-glucosidase gene, and the desosaminyl transferase gene. The glycosylated antibiotic narbomycin was produced in these host cells, and it is believed that YC17 was produced as well. When these host cells are transformed with vectors that drive expression of the picK gene, the antibiotics methymycin, neomethymycin, and picromycin are produced.

In similar fashion, when plasmid pKOS039-18, which encodes a hybrid PKS of the invention that produces 3-deoxy-3-oxo-6-deoxyerythronolide B was expressed in Streptomyces lividans host cells transformed with plasmid pKOS39-104, the 5-desosaminylated analog was produced. Likewise, when plasmid pCK7, which encodes DEBS, which produces 6-deoxyerythronolide B, was expressed in Streptomyces lividans host cells transformed with plasmid pKOS39-104, the 5-desosaminylated analog was produced. These compounds have antibiotic activity and are useful as intermediates in the synthesis of other antibiotics.

EXAMPLE 4

Expression Vector for Desosaminyl Transferase

While the invention provides expression vectors comprising all of the genes required for desosamine biosynthesis and transfer to a polyketide, the invention also provides expression vectors that encode any subset of those genes or any single gene. As one illustrative example, the invention provides an expression vector for desosaminyl transferase. This vector is useful to desosaminylate polyketides in host cells that produce NDP-desosamine but lack a desosaminyl transferase gene or express a desosaminyl transferase that does not function as efficiently on the polyketide of interest as does the desosaminyl transferase of Streptomyces venezuelae. This expression vector was constructed by first amplifying the desosaminyl transferase coding sequence from pKOS023-27 using the primers:

```
                                           (SEQ ID NO: 25)
N3917:  5'-CCCTGCAGCGGCAAGGAAGGACACGACGCCA-3'; and (SEQ ID NO: 26)
N3918:  5'-AGGTCTAGAGCTCAGTGCCGGGCGTCGGCCGG-3',
``` to give a 1.5 kb product. This product was then treated with restriction enzymes PstI and XbaI and ligated with HindIII and XbaI digested plasmid pKOS039-06 together with the 7.6 kb PstI-HindIII restriction fragment of plasmid pWHM1104 to provide plasmid pKOS039-14. Plasmid pWHM1104, described in Tang et at., 1996, Molec. Microbiol. 22(5): 801–813, incorporated herein by reference, encodes the ermE* promoter. Plasmid pKOS039-14 is constructed so that the desosaminyl transferase gene is placed under the control of the ermE* promoter and is suitable for expression of the desosaminyl transferase in Streptomyces, Saccharopolyspora erythraea, and other host cells in which the ermE* promoter functions.

EXAMPLE 5

Heterologous Expression of the picK Gene Product in E. coli

The picK gene was PCR amplified from plasmid pKOS023-28 using the oligonucleotide primers: N024–36B (forward):

```
N024-36B (forward):              (SEQ ID NO: 27)
   5'-TTGCATGCATATGCGCCGTACCCAGCAGGGAACGACC; and N024-37B (reverse):              (SEQ ID NO: 28)
   5'-TTGAATTCTCAACTAGTACGGCGGCCCGCCTCCCGTCC.
```

These primers alter the *Streptomyces* GTG start codon to ATG and introduce a SpeI site at the C-terminal end of the gene, resulting in the substitution of a serine for the terminal glycine amino acid residue. The blunt-ended PCR product was subcloned into the commercially available vector pCR-script at the SrfI site to yield plasmid pKOS023-60. An ~1.3 kb NdeI-XhoI fragment was then inserted into the NdeI/XhoI sites of the T7 expression vector pET22b (Novagen, Madison, Wis.) to generate pKOS023-61. Plasmid pKQS023-61 was digested with restriction enzymes SpeI and EcoRI, and a short linker fragment encoding 6 histidine residues and a stop codon (composed of oligonucleotides 30–85a:

```
                                 (SEQ ID NO: 29)
30-85a:  5'-CTAGTATGCATCATCATCATCATCATTAA-3'; and (SEQ ID NO: 30)
30-85b:  5'-AATTTTAATGATGATGATGATGATGCATA-3')
``` was inserted to obtain plasmid pKOS023-68. Both plasmid pKOS023-61 and pKOS023-68 produced active PicK enzyme in recombinant *E. coli* host cells.

Plasmid pKOS023-61 was transformed into *E. coli* BL21-DE3. Successful transformants were grown in LB-containing carbenicillin (100 μg/ml) at 37° C. to an $OD_{600}$ of 0.6. Isopropyl-beta-D-thiogalactopyranoside (IPTG) was added to a final concentration of 1 mM, and the cells were grown for an additional 3 hours before harvesting. The cells were collected by centrifugation and frozen at −80° C. A control culture of BL21-DE3 containing the vector plasmid pET21c (Invitrogen) was prepared in parallel.

The frozen BL21-DE3/pKOS023-61 cells were thawed, suspended in 2 μL of cold cell disruption buffer (5 mM imidazole, 500 mM NaCl, 20 mM Tris/HCl, pH 8.0) and sonicated to facilitate lysis. Cellular debris and supernatant were separated by centrifugation and subjected to SDS-PAGE on 10–15% gradient gels, with Coomassie Blue staining, using a Pharmacia Phast Gel Electrophoresis system. The soluble crude extract from BL21-DE3/pKOS023-61 contained a Coomassie stained band of $M_r$~46 kDa, which was absent in the control strain BL21-DE3/pET21c.

The hydroxylase activity of the picK protein was assayed as follows. The crude supernatant (20 μL) was added to a reaction mixture (100 μL total volume) containing 50 mM Tris/HCl (pH 7.5), 20 μM spinach ferredoxin, 0.025 Unit of spinach ferredoxin:$NADP^+$ oxidoreductase, 0.8 Unit of glucose-6-phosphate dehydrogenase, 1.4 mM $NADP^+$, 7.6 mM glucose-6 phosphate, and 20 nmol of narbomycin. The narbomycin was purified from a culture of *Streptomyces narbonensis*, and upon LC/MS analysis gave a single peak of $[M+H]^+$=510. The reaction was allowed to proceed for 105 minutes at 30° C. Half of the reaction mixture was loaded onto an HPLC, and the effluent was analyzed by evaporative light scattering (ELSD) and mass spectrometry. The control extract (BL21-DE3/pET21c) was processed identically. The BL21-DE3/pKOS023-61 reaction contained a compound not present in the control having the same retention time, molecular weight and mass fragmentation pattern as picromycin ($[M+H]^+$=526). The conversion of narbomycin to picromycin under these conditions was estimated to be greater than 90% by ELSD peak area.

The poly-histidine-linked PicK hydroxylase was prepared from pKOS023-68 transformed into *E. coli* BL21 (DE3) and cultured as described above. The cells were harvested and the PicK protein purified as follows. All purification steps were performed at 4° C. *E. coli* cell pellets were suspended in 32 μL of cold binding buffer (20 mM Tris/HCl, pH 8.0, 5 mM imidazole, 500 mM NaCl) per mL of culture and lysed by sonication. For analysis of *E. coli* cell-free extracts, the cellular debris was removed by low-speed centrifugation, and the supernatant was used directly in assays. For purification of PicK/6-His, the supernatant was loaded (0.5 mL/min.) onto a 5 mL HiTrap Chelating column (Pharmacia, Piscataway, N.J.), equilibrated with binding buffer. The column was washed with 25 μL of binding buffer and the protein was eluted with a 35 μL linear gradient (5–500 mM imidazole in binding buffer). Column effluent was monitored at 280 nm and 416 nm. Fractions corresponding to the 416 nm absorbance peak were pooled and dialyzed against storage buffer (45 mM Tris/HCl, pH 7.5, 0.1 mM EDTA, 0.2 mM DTT, 10% glycerol). The purified 46 kDa protein was analyzed by SDS-PAGE using Coomassie blue staining, and enzyme concentration and yield were determined.

Narbomycin was purified as described above from a culture of *Streptomyces narbonensis* ATCC19790. Reactions for kinetic assays (100 μL) consisted of 50 mM Tris/HCl (pH 7.5), 100 μM spinach ferredoxin, 0.025 Unit of spinach ferredoxin:$NADP^+$ oxidoreductase, 0.8 U glucose-6-phosphate dehydrogenase, 1.4 mM $NADP^+$, 7.6 mM glucose-6-phosphate, 20–500 μM narbomycin substrate, and 50–500 nM of PicK enzyme. The reaction proceeded at 30° C., and samples were withdrawn for analysis at 5, 10, 15, and 90 minutes. Reactions were stopped by heating to 100° C. for 1 minute, and denatured protein was removed by centrifugation. Depletion of narbomycin and formation of picromycin were determined by high performance liquid chromatography (HPLC, Beckman C-18 0.46×15 cm column) coupled to atmospheric pressure chemical ionization (APCI) mass spectroscopic detection (Perkin Elmer/Sciex API 100) and evaporative light scattering detection (Alltech 500 ELSD).

EXAMPLE 6

Expression of the picK Gene Encoding the Hydroxylase in Streptomyces Narbonensis To produce picromycin in *Streptomyces narbonensis*, a host that produces narbomycin but not picromycin, the methods and vectors of the invention were used to express the picK gene in this host.

The picK gene was amplified from cosmid pKOS023-26 using the primers:

N3903: 5'-TCCTCTAGACGTTTCCGT-3'; and (SEQ ID NO: 31)

N3904: 5'-TGAAGCTTGAATTCAACCGGT-3' (SEQ ID NO: 32)

to obtain an ~1.3 kb product. The product was treated with restriction enzymes XbaI and HindIII and ligated with the 7.6 kb XbaI-HindIII restriction fragment of plasmid pWHM1104 to provide plasmid pKOS039-01, placing the picK gene under the control of the ermE* promoter. The resulting plasmid was transformed into purified stocks of S. narbonensis by protoplast fusion and electroporation. The transformants were grown in suitable media and shown to convert narbomycin to picromycin at a yield of over 95%.

EXAMPLE 7

Construction of a Hybrid DEBS/Narbonolide PKS

This example describes the construction of illustrative hybrid PKS expression vectors of the invention. The hybrid PKS contains portions of the narbonolide PKS and portions of rapamycin and/or DEBS PKS. In the first constructs, pKOS039-18 and pKOS039-19, the hybrid PKS comprises the narbonolide PKS extender module 6 ACP and thioesterase domains and the DEBS loading module and extender modules 1–5 as well as the KS and AT domains of DEBS extender module 6 (but not the KR domain of extender module 6). In pKOS039-19, the hybrid PKS is identical except that the KS1 domain is inactivated, i.e., the ketosynthase in extender module 1 is disabled. The inactive DEBS KS1 domain and its construction are described in detail in PCT publication Nos. WO 97/02358 and 99/03986, each of which is incoxporated herein by reference. To construct pKOS039-18, the 2.33 kb BamHI-EcoRI fragment of pKOS023-27, which contains the desired sequence, was amplified by PCR and subcloned into plasmid pUC19. The primers used in the PCR were:

N3905: 5'-TTTATGCATCCCGCGGGTCCCGGCGAG-3'; and (SEQ ID NO: 33)

N3906: 5'-TCAGAATTCTGTCGGTCACTTGCCCGC-3'. (SEQ ID NO: 34)

The 1.6 kb PCR product was digested with PstI and EcoRI and cloned into the corresponding sites of plasmid pKOS015-52 (this plasmid contains the relevant portions of the coding sequence for the DEBS extender module 6) and commercially available plasmid pLitmus 28 to provide plasmids pKOS039-12 and pKOS039-13, respectively. The BglII-EcoRI fragment of plasmid pKOS039-12 was cloned into plasmid pKOS011-77, which contains the functional DEBS gene cluster and into plasmid pJRJ2, which contains the mutated DEBS gene that produces a DEBS PIG in which the KS domain of extender module 1 has been rendered inactive. Plasmid pJRJ2 is described in PCT publication Nos. 99/03986 and 97/02358, incorporated herein by reference.

Plasmids pKOS039-18 and pKOS039-19, respectively, were obtained. These two plasmids were transformed into Streptomyces coelicolor CH999 by protoplast fusion. The resulting cells were cultured under conditions such that expression of the PKS occurred. Cells transformed with plasmid pKOS039-18 produced the expected product 3-deoxy-3-oxo-6-deoxyerythronolide B. When cells transformed with plasmid pKOS039-19 were provided (2S,3R)-2-methyl-3-hydroxyhexanoate NACS, 13-desethyl-13-propyl-3-deoxy-3-oxo-6-deoxyerythronolide B was produced.

EXAMPLE 8

6-Hydroxylation of 3,6-dideoxy-3-oxoerythronolide B Using the eryF Hydroxylase

Certain compounds of the invention can be hydroxylated at the C6 position in a host cell that expresses the eryF gene. These compounds can also be hydroxylated in vitro, as illustrated by this example.

The 6-hydroxylase encoded by eryF was expressed in E. coli, and partially purified. The hydroxylase (100 pmol in 10 µL) was added to a reaction mixture (100 µl total volume) containing 50 mM Tris/HCl (pH 7.5), 20 µM spinach ferredoxin, 0.025 Unit of spinach ferredoxin:NADP$^+$ oxidoreductase, 0.8 Unit of glucose-6-phosphate dehydrogenase, 1.4 mM NADP$^+$, 7.6 mM glucose-6-phosphate, and 10 nmol 6-deoxyerythronolide B. The reaction was allowed to proceed for 90 minutes at 30° C. Half of the reaction mixture was loaded onto an HPLC, and the effluent was analyzed by mass spectrometry. The production of erythronolide B as evidenced by a new peak eluting earlier in the gradient and showing [M+H]$^+$=401. Conversion was estimated at 50% based on relative total ion counts.

Those of skill in the art will recognize the potential for hemiketal formation in the above compound and compounds of similar structure. To reduce the amount of hemiketal formed, one can use more basic (as opposed to acidic) conditions or employ sterically hindered derivative compounds, such as 5-desosaminylated compounds.

EXAMPLE 9

Measurement of Antibacterial Activity

Antibacterial activity was determined using either disk diffusion assays with Bacillus cereus as the test organism or by measurement of minimum inhibitory concentrations (MIC) in liquid culture against sensitive and resistant strains of Staphylococcus pneumoniae.

EXAMPLE 10

Construction of Desosamine Containing Polyketide Libraries Using a Glycosyltransferase with Broad Substrate Specificity Desosamine is an important deoxyaminosugar present on a number of structurally related macrolide antibiotics such as erythromycin and is the only glycoside present on picromycin, methymycin, and the highly potent semisynthetic ketolides. In this example, a set of nine deoxysugar biosynthetic and auxiliary genes from the picromycin/methymycin (Pik) cluster was integrated in the chromosome of Streptomyces lividans to create a host that synthesizes TDP-D-desosamine and can be used in combination with PKS expression plasmids to generate libraries of desosaminylated polyketides. The versatility of the DesVII desosaminyltransferase is demonstrated by formation of desosaminylated macrolides from more than twenty different 14-membered lactones. The attachment of desosamine is sufficient to confer antibiotic activity to each of the otherwise inactive aglycones, reinforcing the belief that this sugar plays a critical role in the molecular binding properties of erythromycin and related macrolides. This host and others that can be engineered to produce deoxysugar and polyketide tailoring pathways in accordance with the methods of the invention are valuable tools for expanding the size and diversity of polyketides that can be generated by combinatorial biosynthesis. References cited in this example are indicated by a reference number; the numbered list of references is located at the end of this example. All references cited are incorporated herein by reference.

Much of the structural diversity and complexity among polyketides can be attributed to the chemistry performed by PKSs (1), and the modular architecture of catalytic domains within PKSs has been exploited by different rational and combinatorial engineering approaches to create polyketide diversity (2–4). However, structural variability among polyketides can also result from post-PKS biosynthetic steps, including oxidation and/or glycosylation with unique deoxy and amino sugars. Such modifications are often necessary to impart or enhance the specific biological activity of the molecule. For example, erythromycin A contains two deoxysugar moieties, L-cladinose and D-desosamine, that are required for antibacterial activity and the absence of either carbohydrate results in loss of potency. Although some chemical modifications to erythromycin have been discovered that can ameliorate the loss of the cladinose residue (5–7), there has been no substitution found for desosamine. This important deoxyaminosugar is also present in other macrolide antibiotics, such as oleandomycin and megalomicin, and is the only glycoside necessary to confer antibacterial activity to picromycin, methymycin, and the semisynthetic ketolide pharmacophores.

Polyketide libraries generated by genetic modification of macrolide PKSs in which enzymatic domains and entire protein subunits were removed, added, or exchanged in various combinations have been produced (3, 4, 8). Because these libraries were constructed in heterologous hosts lacking glycosylation pathways, only the corresponding aglycones were produced. The methods and reagents of the present invention can be used to expand the capabilities of the combinatorial biosynthesis strategies described to incorporate post-PKS tailoring steps, in particular the addition of deoxysugar components.

Some experiments have been performed in which structurally modified macrolactones are subsequently glycosylated in their native hosts (9–13), and also in bioconversion experiments in which a modified aglycone is fed to a PKS-blocked mutant strain (14). These experiments indicate that glycosyltransferases are able to accept polyketide substrates with some amount of structural alteration. However, neither of these approaches is well-suited for the production and biological screening of large numbers of compounds, because most polyketide host organisms are difficult to manipulate genetically and the bioconversion of aglycones requires a tedious initial purification step.

A more practical approach is the heterologous expression of deoxysugar biosynthetic pathways in hosts that have been developed for library expression. Although the effort to clone entire deoxysugar biosynthetic pathways in a heterologous organism can be a significant initial investment (most deoxysugars require six or more enzymatic steps whose genes are typically scattered within a polyketide gene cluster), these expression vectors, once made, can be easily combined with those containing PKSs to engineer glycosylated libraries rapidly. Olano et al. recently utilized a two-plasmid system to produce L-daunosamine, the deoxyaminosugar of daunorubicin and doxorubicin, in *Streptomyces lividans* (15).

Here we report the development of a single expression vector for the production of desosaminylated macrolides in *Streptomyces*. Desosamine was selected as the sugar constituent, because it was believed that addition of this single deoxysugar would be sufficient to confer antibacterial activity upon macrolactones to which it was attached. The expression vector was combined with a library of existing PKS expression plasmids to produce several novel glycosylated macrolide compounds in *S. lividans*, providing the first examples in which both polyketide and deoxysugar pathways have been placed in a single heterologous host.

A. Material and Methods (i) Strains, culture conditions, and DNA manipulation

DNA manipulation was performed in *Escherichia coli* XL1-Blue (Stratagene) using standard protocols (16). *Bacillus subtilis* was grown in LB at 37° C. PCR was performed with Pfu polymerase (Stratagene) under conditions recommended by the manufacturer. *S. lividans* K4-114 (17) was used as the host for expression of engineered PKS and desosamine genes. *S. lividans* strains were maintained on R2YE agar plates (18) with appropriate antibiotic selection. *S. lividans* protoplasts were transformed by the standard procedure (18) and transformants were selected using 1 ml of a 1 mg/ml thiostrepton and/or 1 ml of a 2 mg/ml apramycin overlay on R2YE regeneration plates.

(ii) Construction of expression plasmids

Expression plasmid pKOS39-104 was constructed as follows. The 6.0 kb Bgl II-Pst I fragment containing the picromycin des VIII, des VII, desVI and desR (partial) genes from cosmid pKOS23-26 (19) was subcloned into the Bgl II-Pst I sites of pKOS39-98, a pUC19 derivative with a redesigned multiple cloning site. The resulting plasmid, pKOS39-100, contains a Pac I site upstream of the Bgl II site which is used in a later cloning step. The 6 kb Sph I-Psi I fragment containing the desI (partial), desII, desIII, desIV and desV genes from pKOS23-26 was subcloned into the Sph I-Pst I of pUC19 to make pKOS39-102. The remaining 3'-end of the desR gene and 5'-end of the desI gene were PCR amplified from cosmid pKOS23-26 with the following oligonucleotides (restriction sites shown in italics):

```
desR gene:
                                    (SEQ ID NO: 35)
   forward 5'-AGATGCATTTCTGGGATGCCGCCACGGA; and
                                    (SEQ ID NO: 36)
   reverse 5'-CGTCTAGACGTCACCAGACGTTGACCGTG;

desI gene:
                                    (SEQ ID NO: 37)
   forward 5'-TTTCTAGACGGTGGCCCGGAGGGAACATC; and
                                    (SEQ ID NO: 38)
   reverse 5'-CGGAATTCCGCAGCTGGTCGGCGGCGCA.
```

The two PCR fragments were digested with Nsi I-Xba I and Xba I-EcoR I, respectively, and ligated with Nsi I-EcoR I digested Litmus 28 (New England Biolabs) to obtain pKOS39-101B. The 6 kb Sph I-EcoR I fragment of pKOS039-102 was inserted into pKOS39-101B to make pKOS39-103. The 6.4 kb Nsi I-EcoR I fragment of pKOS39-103 and the 6 kb Pac I-Pst I fragment of pKOS39-100 were then ligated together with the 8.5 kb Pac I-EcoR I fragment of pKOS39-44 (20), yielding the final expression plasmid pKOS39-104. A restriction site and function map of this plasmid is shown below.

PATENT
Attorney Docket 300622002121

The two PCR fragments were digested with Nsi I-Xba I and Xba I-EcoR I, respectively, and ligated with Nsi I-EcoR I digested Litmus 28 (New England Biolabs) to obtain pKOS39-101B. The 6 kb Sph I-EcoR I fragment of pKOS39-102 was inserted into pKOS39-101B to make pKOS39-103. The 6.4 kb Nsi I-EcoR I fragment of pKOS39-103 and the 6 kb Pac I-Pst I fragment of pKOS39-100 were then ligated together with the 8.5 kb Pac I-EcoR I fragment of pKOS39-44 (20), yielding the final expression plasmid pKOS39-104. A restriction site and function map of this plasmid is shown below.

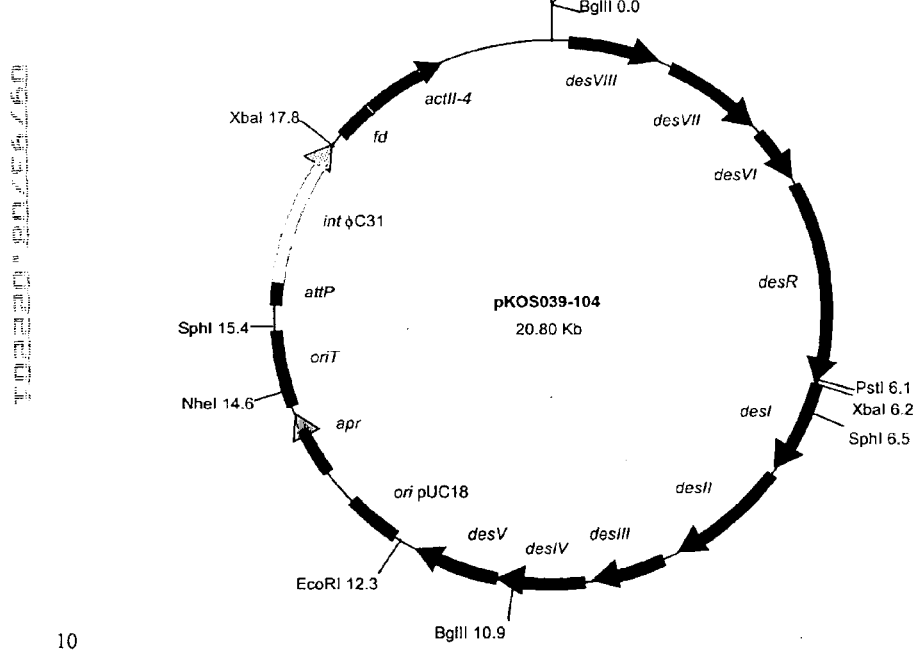

(iii) Production and analysis of compounds

All strains were grown in 5 ml liquid R2YE medium at 30 °C and analyzed following 5 days growth. For bioconversion experiments, aglycones (iii) Production and analysis of compounds All strains were grown in 5 ml liquid R2YE medium at 30° C. and analyzed following 5 days growth. For bioconversion experiments, aglycones (~10 mg/liter) were fed at the start of fermentation. Fermentation broth was analyzed directly by liquid chromatography/mass spectrometry (LC/MS) and evaporative light scattering detection (ELSD) as previously described (20). An authentic sample of narbomycin prepared from *Streptomyces narbonensis* (19) was used to validate production of this compound. For LC/MS analysis of strains containing PKS expression plasmids the cultures were extracted twice with 5 ml of ethyl acetate/triethylamine (99:1), concentrated to dryness and resuspended in 0.5 ml of acetonitrile.

(iv) Antibacterial assays

Extracts prepared from the culture broths as above were assayed for biological activity against *B. subtilis* using an agar plate diffusion method (see Example 9). Samples (5 µl) from each of the extracts were pipetted to sterile filter disks, dried, and placed on an LB plate spread with 20 µl of an overnight culture of *B. subtilis*. The plates were incubated overnight at 37° C. to visualize zones of growth inhibition.

B. Results (i) Construction and validation of a desosamine expression system

The picromycin/methymycin (pik) gene cluster from *Streptomyces venezuelae* (21) was chosen as the source of desosamine biosynthetic genes rather than other available clusters (i.e. erythromycin, oleandomycin, or megalomicin) for several reasons. First, all of the genes required for biosynthesis of TDP-desosamine from glucose-1-phosphate, a primary metabolite, as well as the desosaminyl transferase are present in the pik cluster whereas one or more of the genes are missing or not yet identified in each of the other clusters. Second, the genes from the pik cluster are comprised in a single contiguous segment of DNA (the des cluster), compared to those in other clusters which are dispersed among other genes, facilitating cloning and plasmid construction. The organization of these genes in the picromycin biosynthetic gene cluster is shown below, followed by the depiction of the biosynthetic pathway.

the other cases, desosamine is attached subsequent to addition of at least one other sugar. Furthermore, the difference in macrolactone ring sizes between narbonolide and 10-deoxymethynolide (14 and 12 atoms, respectively) suggests that the desosaminyl transferase from this cluster is somewhat forgiving towards its polyketide substrate.

Seven genes in the des cluster, desI, desII, desIII, desIV, desV, desVI, and desVIII, are presumed to be responsible for the biosynthesis of TDP-D-desosamine (22). Also present is the des VII gene encoding the glycosyltransferase. In addition to catalyzing the transfer of desosamine to both 12- and 14-membered macrolactones, it has been shown that DesVII is able to incorporate non-natural deoxysugar substrates (22, 23). The desR gene encodes a β-glucosidase that removes a glucose residue attached to the C-2' hydroxyl of desosamine (24). It is believed that the glucosylation of desosamine containing macrolides like methymycin, picromycin, and oleandomycin, causes inactivation and provides self-resistance to these compounds which are reactivated by a β-glucosidase upon export (24, 25). *S. lividans* is known to possess at least two such glucosyltransferases which inactivate erythromycin and picromycin by the same mechanism (26). Therefore, it was important to include this gene for expression in *S. lividans* to produce desosaminylated compounds without the glucose modification.

The expression system used here was adopted from the multi-vector system developed for separate expression of erythromycin PKS, or 6-deoxyerythronolide B synthase (DEBS), subunits in *Streptomyces* (4, 27; see also U.S. Pat. No. 6,033,883). Plasmid pKOS39-104 contains the des genes cloned in a single orientation under control of the actI promoter and actII-44 activator. Since pKOS39-104 is a derivative of pSET152 (28), it contains the phiC31-int-attP loci for chromosomal integration in *Streptomyces* and can be used in conjunction with the pRM5-based PKS expression plasmid library (3; see also U.S. Pat. No. 5,672,491). *S. lividans* K4-114 was transformed with pKOS39-104 and designated K39-22. Confirmation that this strain produced TDP-D-desosamine was performed by feeding aglycones to the strain and looking for the presence of desosaminylated compounds by LC/MS analysis.

Four aglycones (~10 mg/liter each) were fed to liquid fermentations of *S. lividans* K39-22: narbonolide and

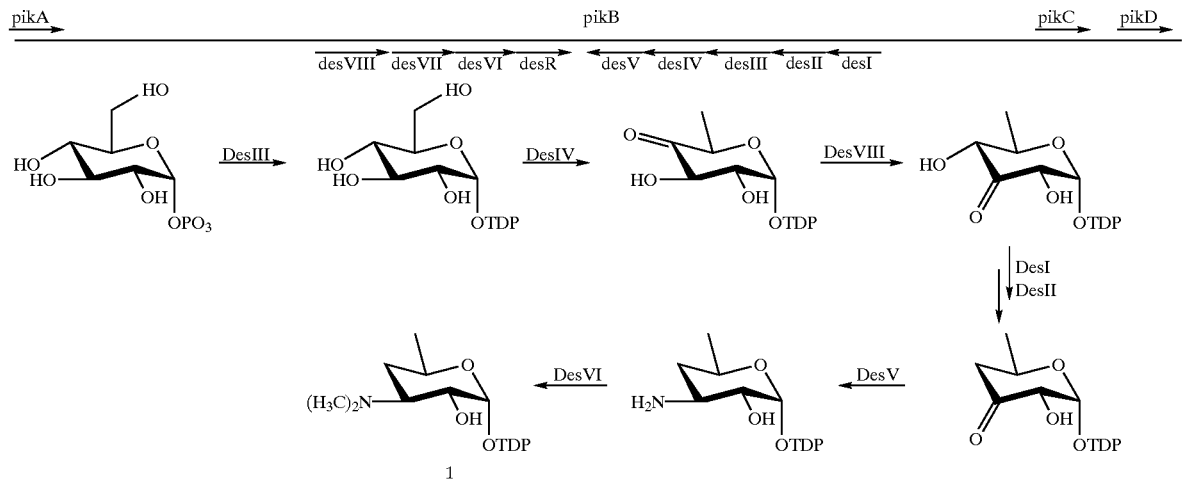

Third, the natural substrates for the desosaminyl transferase from the pik gene cluster, narbonolide and 10-deoxymethynolide, are themselves aglycones; in each of 10-deoxymethynolide, the natural substrates for DesVII, 3-keto-6-deoxyerythronolide B (-6-dEB), and 6-dEB. Fermentation broth from all four aglycone fed strains displayed antibacterial activity against *B. subtilis* whereas *S. lividans* K39-22 alone produced no detectable activity. LC/MS analysis demonstrated that each of the corresponding desosaminylated compounds narbomycin, 10-deoxymethymycin (YC17), 3-keto-5-O-desosaminyl-6-dEB, and 5-O-desosaminyl-6-dEB were produced. In each case, the parent ion (M+H$^+$) of the expected compound was detected in addition to a characteristic ion at 158 amu produced by the desosamine fragment. Production of narbomycin in the narbonolide fed strain was further confirmed by comparison to authentic narbomycin obtained from *S. narbonensis*. LC/MS also revealed that a significant amount (~50–90%) of the aglycone remained unconverted in each of the samples.

These results established that the des expression vector was functional and that the DesVII glycosyltransferase was able to glycosylate non-natural macrolactone substrates. The bioassay results also confirmed that desosamine is sufficient to confer antibacterial activity to these macrolactones. There were no 2'-O-glucosyl derivatives detected, which indicates that the DesR glucosidase included in pKOS39-104 was also operational, although minor glucosylated products were putatively found in subsequent experiments with the strain (see below).

(ii) Co-expression of desosamine and aglycone pathways in *S. lividans*.

Although expression of both a modular polyketide pathway and a deoxysugar pathway together in a heterologous host has not been reported, the bioconversion results suggested that transformation of *S. lividans* K39-22 with plasmids encoding macrolide PKSs would lead to production of desosaminylated compounds. Plasmids encoding the PKSs that, in *S. lividans*, produce the same four aglycones used in the bioconversion studies were therefore transformed into *S. lividans* K39-22. Plasmid pKOS39-86contains the picromycin/methymycin PKS and produces both narbonolide and 10-deoxymethynolide (20). Plasmid pKAO127 contains DEBS and produces 6-dEB (17). Plasmid pKOS39-18 contains DEBS with a modified terminal module that produces 3-keto-6-dEB (20).

Culture broth from each of the transformed strains displayed activity against *B. subtilis*. LC/MS analysis as above confirmed the presence of each of the expected desosaminylated compounds as well as their aglycone precursors and minor amounts of the corresponding 2'-O-glucosyl derivatives. The total yield of narbomycin and 10-deoxymethymycin in *S. lividans* K39-22/pKOS39-86 was approximately 1 mg/liter each and represents about a 20% conversion of the total aglycone produced. Thus, although both PKS and deoxysugar pathways function as expected, complete glycosylation of even the natural substrates for DesVII did not occur under these conditions. *S. lividans* K39-22 contains a copy of the ermE macrolide resistance gene, and no obvious growth defects were observed with production of the biologically active compounds. These results suggest that a limiting amount of TDP-desosamine is being produced by the strain under these conditions.

(iii) Production and biological screening of a glycosylated macrolide library

Over 50 PKS expression plasmids have been constructed and tested in using DEBS and other macrolide PKS genes (3, 8, 20). These PKSs produce a variety of 14-membered macrolactones in which single or multiple carbon centers have been altered. Each plasmid contains the same pRM5-based vector as above, providing a convenient opportunity to expand and diversify any existing aglycone library by routine transformation of *S. lividans* K39-22. Because a C-5 hydroxyl would be necessary for glycosylation, a subset of 19 additional plasmids encoding PKSs that produce compounds containing this functional group was selected and tested. The desired desosaminylated polyketides would theoretically possess antibiotic activity, and the transformed strains can therefore be readily analyzed in a simple bioassay for production of glycosylated macrolides.

All of the strains transformed and tested displayed antimicrobial activity against *B. subtilis*. The presumed structures of the desosamine containing compounds, based on the structures of the aglycones produced by the PKS on each plasmid, are shown below.

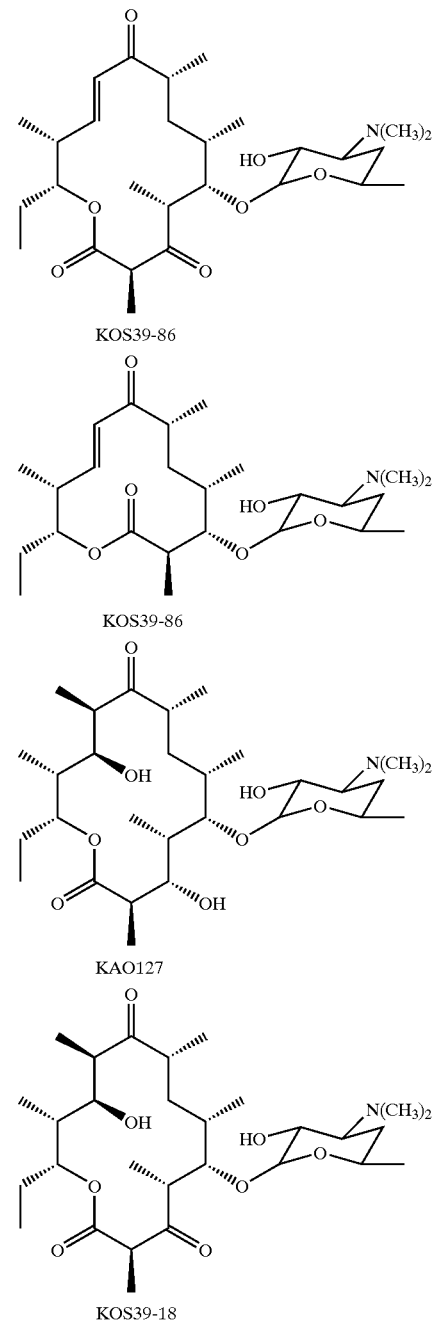

-continued
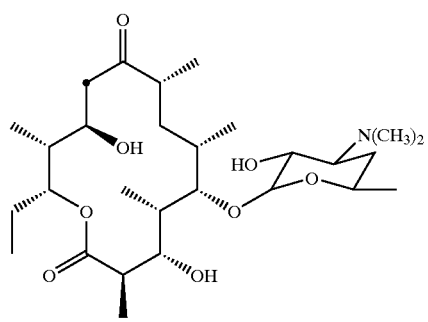
KOS11-62
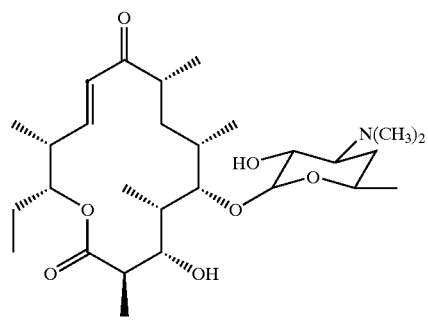
KOS11-62
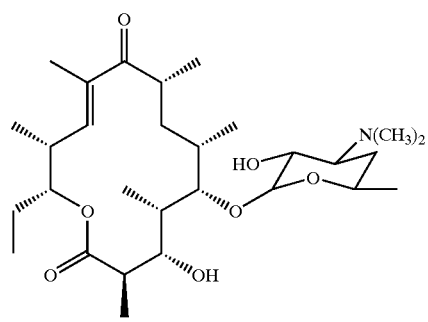
KOS11-64
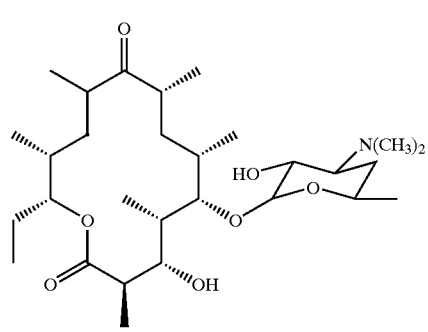
KOS11-66
-continued
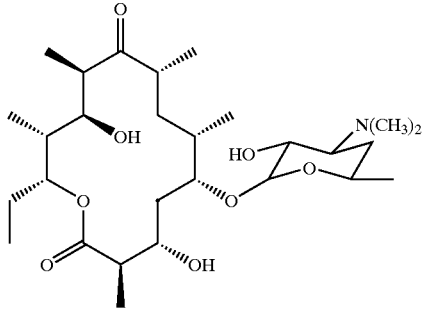
KOS16-47
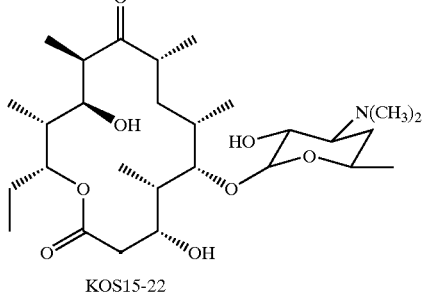
KOS15-22
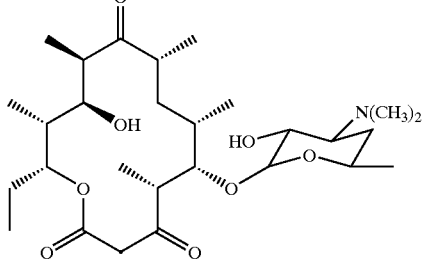
KOS15-106
KOS15-109
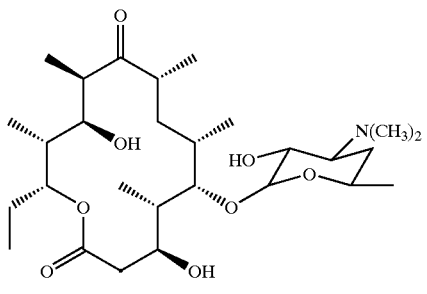
KOS15-106
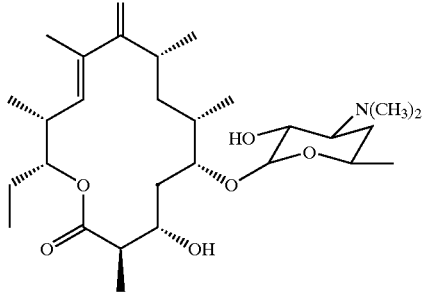
KOS11-82

-continued
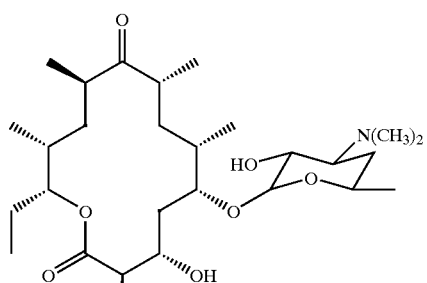
KOS11-83
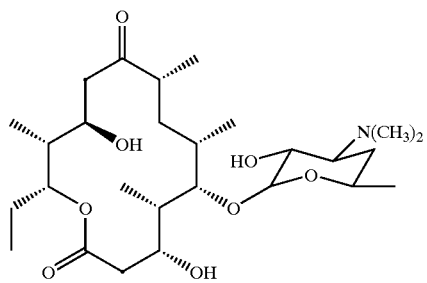
KOS15-116
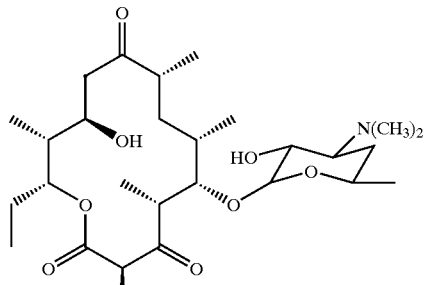
KOS15-87
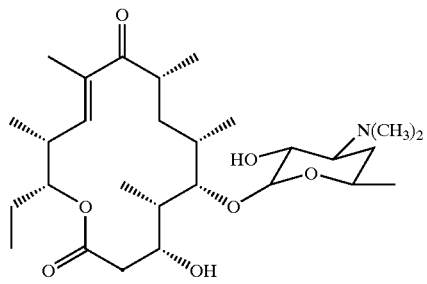
KOS15-42
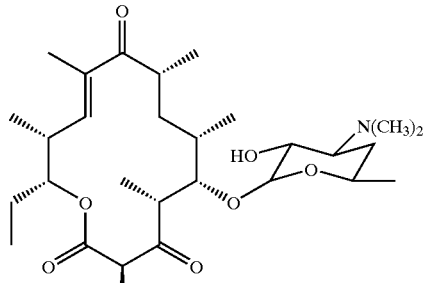
KOS39-20
-continued
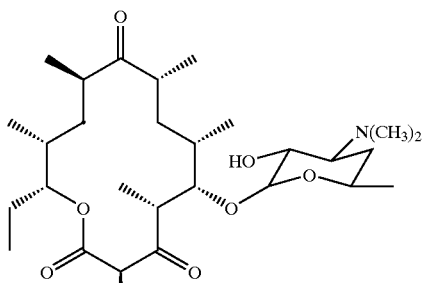
KOS15-46
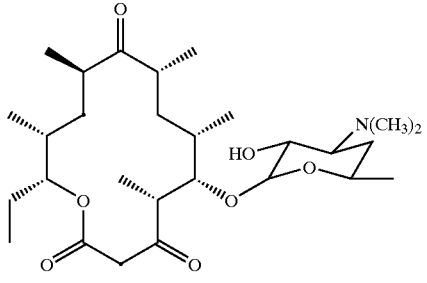
KOS15-125
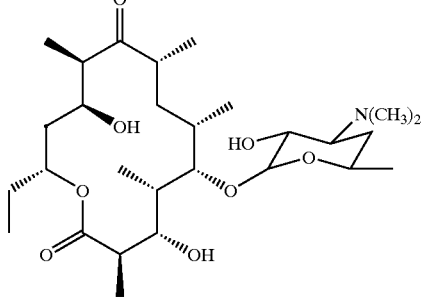
KOS24-15
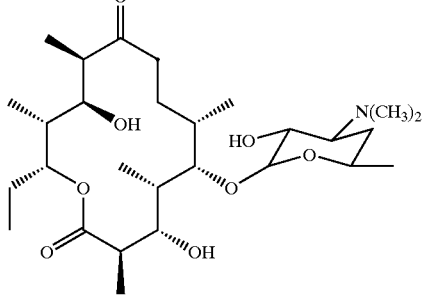
KOS15-30
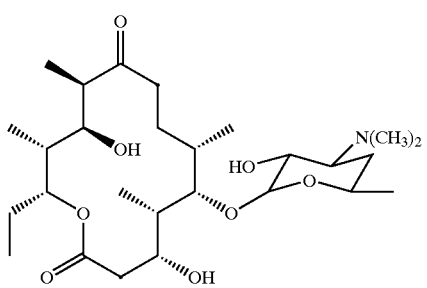
KOS15-34

Culture extracts from six of these stains (those containing plasmids pKOS15-22, pKOS15-106, pKOS39-20, pKOS11-62, pKOS15-30, and pKOS24-15) were examined by LC/MS and, in each case, the expected parent ion was found along with the 158 amu desosamine fragment. Two compounds were detected in the strain containing pKOS15-106 with molecular weights corresponding to 3-hydroxy and 3-keto derivatives. This is consistent with both aglycones being produced by plasmid pKOS15-109 in S. lividans. Two compounds were also detected in the strain with pKOS11-62, the predicted molecule, 5-O-desosaminyl-10-desmethyl-6-dEB, and a putative dehydrated derivative at carbons C-10 and C-11. Both aglycones were also produced when the plasmid was originally analyzed in S. lividans K4-114 (3), although only the former was reported at that time. As with the first set of plasmids tested, small amounts of 2'-O-glucosylated derivatives could also be detected in some of the culture extracts. The yields of the desosamine containing compounds were too low to determine absolute titers (<1 mg/L) and, therefore, the relative antibacterial activity of the compounds could not be determined from these assays.

C. Discussion

This example demonstrates that a minimal set of seven genes (desI, II, III, IV, V, VI, VIII) is sufficient for biosynthesis of TDP-desosamine from glucose-1-phosphate in S. lividans. The apparent low abundance of TDP-desosamine in the engineered host could be due either to the availability of glucose-1-phosphate in this host or to poor expression of the sugar biosynthesis and/or transferase genes. Alternatively, it is interesting to note that narbonolide and 10-deoxymethynolide are present in the natural picromycin/methymycin producing organism, S. venezuelae, and could therefore reflect that one or more of the enzymes from the des cluster is relatively inefficient. One can increase the amount of TDP-desosamine either by increasing expression levels of these genes and/or by complementing one or more of the enzymes in the pathway with homologs from other clusters such as erythromycin or oleandomycin.

Expression of the minimal desosamine biosynthesis genes together with the DesVII desosaminyltransferase in S. lividans has enabled the production of more than 20 glycosylated macrolides with detectable antibacterial activity. The structures of the macrolides that were glycosylated highlight both the remarkable substrate tolerance of the DesVII glycosyltransferase as well as the ability of desosamine to impart biological activity to structurally diverse macrolactones. In addition to their antibacterial properties the desosamine containing compounds presented here may possess additional biological properties that are associated with erythromycin and other macrolides, including motilin antagonism and anti-inflammatory activities. Furthermore, the demonstration by others that DesVII and other glycosyltransferases can also tolerate modifications of the sugar substituent (22, 23, 29) opens the door to manipulation of both polyketide and deoxysugar pathways for the production of 'unnatural' natural product libraries.

References

1. O'Hagan, D. (1991) *The polyketide metabolites* (Ellis Horwood, Chichester, UK).
2. Hutchinson, C. R. (1998) *Curr. Opin. Microbiol.* 1, 319–329.
3. McDaniel, R., Thamchaipenet, A., Gustafsson, C., Fu, H., Betlach, M., Betlach, M. & Ashley, G. (1999) *Proc. Natl. Acad. Sci. USA* 96, 1846–1851.
4. Xue, Q., Ashley, G., Hutchinson, C. R. & Santi, D. V. (1999) *Proc. Natl. Acad. Sci. USA* 96, 11740–11745.
5. Asaka, T., Misawa, Y., Kashimura, M., Morimoto, S. & Hatayama, K. (1997) U.S. Pat. No. 5,631,354.
6. Elliot, R. L., Or, Y. S., Pireh, D. & Chu, D. T. (1998) U.S. Pat. No. 5,747,466.
7. Agouridas, C., Denis, A., Auger, J.-M., Benedetti, Y., Bonnefoy, A., Bretin, F., Chantot, J.-F., Dussarat, A., Fromentin, C., D'Ambrieres, S. G., et al. (1998) *J. Med. Chem.* 41, 4080–4100.
8. Tang, L., Fu, H. & McDaniel, R. (2000) *Chem. & Biol.* 7, 77–84.
9. Donadio, S., Staver, M. J., McAlpine, J. B., Swanson, S. J. & Katz, L. (1991) *Science* 252, 675–679.
10. Donadio, S., McAlpine, J. B., Sheldon, P. J., Jackson, M. & Katz, L. (1993) *Proc. Natl. Acad. Sci. USA* 90, 7119–7123.
11. Ruan, X. R., Pereda, A., Stassi, D. L., Zeidner, D., Summers, R. G., Jackson, M., Shivakumar, A., Kakavas, S., Staver, M. J., Donadio, S., et al. (1997) *J. Bacteriol.* 179, 6416–6425.
12. Stassi, D. L., Kakavas, S. J., Reynolds, K. A., Gunawardana, G., Swanson, S., Zeidner, D., Jackson, M., Liu, H., Buko, A. & Katz, L. (1998) *Proc. Natl. Acad. Sci. USA* 95, 7305–7309.
13. Marsden, A. F. A., Wilkinson, B., Cortés, J., Dunster, N. J., Staunton, J. & Leadlay, P. F. (1998) *Science* 279, 199–202.
14. Jacobsen, J. R., Hutchinson, C. R., Cane, D. E. & Khosla, C. (1997) *Science* 277, 367–369.
15. Olano, C., Lomovskaya, N., Fonstein, L., Roll, J. T. & Hutchinson, C. R. (1999) *Chem. & Biol.* 6, 845–855.
16. Sambrook, J., Fritsch, E. F. & Maniatis, T. (1989) *Molecular Cloning: A Laboratory Manual* (Cold Spring Harbor Laboratory Press, Plainview, N.Y.).
17. Ziermann, R. & Betlach, M. C. (1999) *Biotechniques* 26, 106–110.
18. Hopwood, D. A., Bibb, M. J., Chater, K. F., Kieser, T., Bruton, C. J., Kieser, H. M., Lydiate, D. J., Smith, C. P., Ward, J. M. & Schrempf, H. (1985) *Genetic Manipulation of Streptomyces: A Laboratory Manual* (The John Innes Foundation, Norwich, UK).
19. Betlach, M. C., Kealey, J. T., Betlach, M. C., Ashley, G. A. & McDaniel, R. (1998) *Biochemistry* 37, 14937–14942.
20. Tang, L., Fu, H., Betlach, M. C. & McDaniel, R. (1999) *Chem. & Biol.* 6, 553–558.
21. Xue, Y., Zhao, L., Liu, H.-w. & Sherman, D. H. (1998) *Proc. Natl. Acad. Sci. USA* 95, 12111–12116.
22. Zhao, L., Sherman, D. H. & Liu, H.-w. (1998) *J. Am. Chem. Soc.* 120, 10256–10257.
23. Zhao, L., Ahlert, J., Xue, Y., Thorson, J. S., Sherman, D. H. & Liu, H.-w. (1999) *J. Am. Chem. Soc.* 121, 9881–9882.
24. Zhao, L., Sherman, D. H. & Liu, H.-w. (1998) *J. Am. Chem. Soc.* 120, 9374–9375.
25. Quiros, L. M., Aguirrezabalaga, I., Olano, C., Mendez, C. & Salas, J. A. (1998) *Mol. Microbiol.* 28, 1177–1185.
26. Jenkins, G. & Cundliffe, E. (1991) *Gene* 108, 55–62.
27. Ziermann, R. & Betlach, M. (2000) *J. Ind. Microbiol. Biotech.* 24, 46–50.
28. Bierman, M., Logan, R., O'Brien, K., Seno, E. T., Nagaraja, R. & Schoner, B. E. (1992) *Gene* 116, 43–49.
29. Gaisser, S., Reather, J., Wirtz, G., Kellenberger, L., Staunton, J. & Leadlay, P. F. (2000) *Mol. Microbiol.* 36, 391–401.

The invention having now been described by way of written description and example, those of skill in the art will recognize that the invention can be practiced in a variety of embodiments and that the foregoing description and examples are for purposes of illustration and not limitation of the following claims.

What is claimed is:

1. An isolated recombinant DNA compound that comprises a beta-glucosidase gene (desR) of *Streptomyces venezuelae* comprising a sequence encoding SEQ ID NO:12 and a control sequence positioned to express said gene.

2. The DNA compound of claim 1 that is an expression vector comprising the desI (SEQ ID NO:9), desII (SEQ ID NO:10), desIII (SEQ ID NO:14), desIV (SEQ ID NO:15), desV (SEQ ID NO:6) desVI (SEQ ID NO:11), desVII (SEQ ID NO:8) and desVIII (SEQ ID NO:7) genes and one or more control sequence(s) positioned to express said genes.

3. The DNA compound of claim 2 wherein said genes are in the order desVIII, desVII, desVI, desR, desI, desII, desIII, desIV, desV.

4. The DNA compound of claim 2 wherein said desVIII, desVII, desVI, desR, desI, desII, desIII, desIV, and desV genes are in the same orientation in the vector.

5. A recombinant host cell that is transformed with the DNA compound of claim 2, or progeny of said cell.

6. The recombinant host cell of claim 5 that is other than a *Streptomyces venezuelae* host cell.

7. The recombinant host cell of claim 6 that is of genus *Streptomyces*.

8. The DNA compound of claim 2, wherein said host cell produces desosamine and wherein said host cell, in its naturally occurring non-recombinant state cannot produce desosamine.

9. The recombinant host cell of claim 8 that produces a desosaminylated polyketide.

10. The recombinant host cell of claim 9 wherein the polyketide that is desosaminylated is a product of expression of a recombinant, modified or chimeric polyketide synthase that is not expressed by the host cell in its naturally occurring non-recombinant state.

11. The recombinant host cell of claim 9 wherein the polyketide that is desosaminylated is a product of expression of a recombinant expression vector expressing a protein encoding at least one module of a polyketide synthase.

12. A method of producing a desosaminylated polyketide comprising the steps a) feeding one or more aglycones to a cell culture comprising recombinant host cells according to claim 8, and b) fermenting said culture under conditions in which a desosaminylated polyketide is produced.

13. A method of producing a desosaminylated polyketide comprising the steps a) fermenting a cell culture comprising recombinant host cells according to claim 8, and b) fermenting said culture under conditions in which a desosaminylated polyketide is produced.

14. A method for increasing the yield of a desosaminylated polyketide in a cell, which method comprises transforming the cell with a recombinant expression vector that encodes a functional beta-glucosidase gene, wherein the cell produces a polyketide or is modified to produce a polyketide.

15. The method of claim 14 wherein the cell is a recombinant host cell.

16. The method of claim 15 wherein the recombinant host cell is *Streptomyces lividans, S. coelicolor*, or *E. coli*.

17. The method of claim 15 wherein the functional beta-glucosidase gene is from *S. venzuelae*.

18. The method of claim 17 wherein the functional beta-glucosidase protein is encoded by desR gene found on a 6.0 kb Bgl II-Pst I fragment of cosmid pKOS23-26 (ATCC accession no.: 203141).

* * * * *

UNITED STATES PATENT AND TRADEMARK OFFICE
CERTIFICATE OF CORRECTION

PATENT NO. : 6,902,913 B2
DATED : June 7, 2005
INVENTOR(S) : Melanie C. Betlach et al.

It is certified that error appears in the above-identified patent and that said Letters Patent is hereby corrected as shown below:

Column 125,
Line 7, please add -- further -- after "vector".
Lines 26 and 33-34, please replace "naturally occurring non-recombinant" with -- wild-type --.
Lines 31 and 36, please replace "a product" with -- produced as a result --.

Column 126,
Line 2, please replace "encoding" with -- comprising --.
Lines 20-21, please replace "that encodes a functional" with -- encoding --.
Line 21, please replace "gene" with -- having SEQ ID NO:12 --.
Line 25, please replace "a recombinant host cell" with -- modified to produce a polyketide --.
Line 27, please delete "recombinant".
Line 29, please replace "functional" with -- recombinant expression vector comprises --.
Line 30, please delete "gene is".

Signed and Sealed this

Sixteenth Day of August, 2005

JON W. DUDAS
*Director of the United States Patent and Trademark Office*